US005763437A

United States Patent [19]

Sato et al.

[11] Patent Number: 5,763,437

[45] Date of Patent: Jun. 9, 1998

[54] BENZODIAZEPINE DERIVATIVES

[75] Inventors: Yoshinari Sato, Takaishi; Kazuo Sakane, Kawanishi; Seiichiro Tabuchi, Nishinomiya; Hitoshi Mitsui, Kitakatsuragi-gun; Ikuyo Katsumi, Osaka; Yuichi Satoh, Suita, all of Japan

[73] Assignees: Fujisawa Pharmaceutical Co., Ltd.; Nippon Shokubai Co., Ltd., both of Osaka, Japan

[21] Appl. No.: 776,196

[22] PCT Filed: Jul. 27, 1995

[86] PCT No.: PCT/JP95/01497

§ 371 Date: Jan. 29, 1997

§ 102(e) Date: Jan. 29, 1997

[87] PCT Pub. No.: WO96/04254

PCT Pub. Date: Feb. 15, 1996

[30] Foreign Application Priority Data

| | | | |
|---|---|---|---|
| Jul. 29, 1994 | [GB] | United Kingdom | 9415311 |
| Jan. 30, 1995 | [GB] | United Kingdom | 9501726 |

[51] Int. Cl.$^6$ ........................ A61K 31/55; C07D 243/14; C07D 243/24; C07D 243/26

[52] U.S. Cl. ........................ 514/221; 540/509; 540/504

[58] Field of Search ........................ 540/509, 504; 514/211, 221

[56] References Cited

U.S. PATENT DOCUMENTS

| | | | |
|---|---|---|---|
| 4,628,084 | 12/1986 | Bock et al. | 540/509 |
| 4,820,834 | 4/1989 | Evans et al. | 540/504 |
| 4,970,207 | 11/1990 | Sato et al. | 514/211 |
| 4,981,847 | 1/1991 | Sato et al. . | |
| 5,155,101 | 10/1992 | Sato et al. . | |
| 5,248,679 | 9/1993 | Sato et al. . | |
| 5,264,433 | 11/1993 | Sato et al. | 514/221 |
| 5,382,664 | 1/1995 | Sato et al. . | |

*Primary Examiner*—Johann Richter
*Assistant Examiner*—Sabiha N. Qazi
*Attorney, Agent, or Firm*—Oblon, Spivak, McClelland, Maier & Neustadt, P.C.

[57] ABSTRACT

Benzodiazepine derivatives of formula (I) wherein $R^1$ is aryl which may have one or more suitable substituent(s), $R^2$ is $C_3$–$C_8$ cycloalkyl which may have one or more suitable substituent(s), A is lower alkylene, $R^3$ is a heterocyclic group selected from the group consisting of tetrahydrofuryl, dioxolanyl, filryl, thienyl, isoxazolyl, pyridyl, benzimidazolyl, benzotiazolyl, benzoxazolyl, benzopyrany, quinolyl, isoquinolyl, tetrahydroisoquinolyl, benzothienyl and benzofuryl, each of which may have one or more suitable substituent(s), or a pharmaceutically acceptable salt thereof, which are useful as a medicament.

8 Claims, No Drawings

BENZODIAZEPINE DERIVATIVES

TECHNICAL FIELD

This application is a 371 of PCT/JP95/01497

This invention relates to new benzodiazepine derivatives or a pharmaceutically acceptable salts thereof which are useful as a medicament.

BACKGROUND ART

Some benzodiazepine derivatives have been known as described, for example, in European Patent Application Publication No. 349949.

DISCLOSURE OF INVENTION

This invention relates to new benzodiazepine derivatives or pharmaceutically acceptable salts thereof.

More particularly, it relates to new benzodiazepine derivatives and pharmaceutically acceptable salts thereof which are selective cholecystokinin-B (CCK-B) antagonists or cholecystokinin-A and B (CCK-A/B) antagonists and therefore useful as therapeutical and/or preventive agents for disorders of appetite regulatory systems (e.g., anorexia, etc.), disorders associated with intestinal smooth muscle hyperactivity (e.g., irritable bowel syndrome, sphincter spasm, etc.), panic disorder, psychosis (e.g., schizophrenia, etc.), pancreatitis, etc. and also useful as analgesics.

The benzodiazepine derivatives of this invention can be represented by the following formula (I):

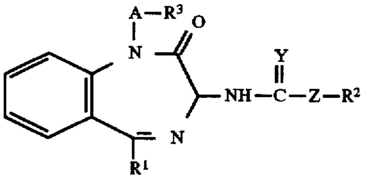

(I)

wherein $R^1$ is aryl or $C_3$–$C_8$ cycloalkyl, each of which may have one or more suitable substituent(s), $R^2$ is $C_3$–$C_8$ cycloalkyl, aryl, indanyl or a heterobicyclic group, each of which may have one or more suitable substituent(s), A is lower alkylene, $R^3$ is a heterocyclic group selected from the group consisting of tetrahydrofuryl, dioxolanyl, furyl, thienyl, isoxazolyl, pyridyl, benz imidazolyl, benzothiazolyl, benzoxazolyl, benzopyranyl, quinolyl, isoquinolyl, tetrahydroisoquinolyl, benzothienyl and benzofuryl, each of which may have one or more suitable substituent(s); or a group of the formula: —X—$R^4$

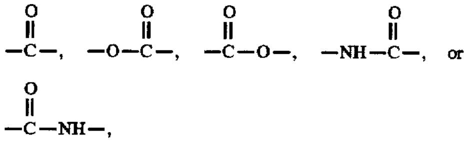

and $R^4$ is thiomorpholinyl; pyridyl; a bridged heterocyclic group containing at least one nitrogen atom, which may have one or more suitable substituent(s); or a bridged cyclic-hydrocarbon group), Y is O or S, and —Z— is direct single bond between carbon and $R^2$,

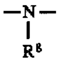

(in which $R^8$ is hydrogen or lower alkyl), or a pharmaceutically acceptable salt thereof. According to the present invention, the new benzodiazepine derivatives (I) may be prepared by the processes which are illustrated in the following scheme.

Process 1

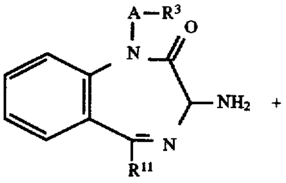

(II)

or its reactive derivative at the amino group or a salt thereof

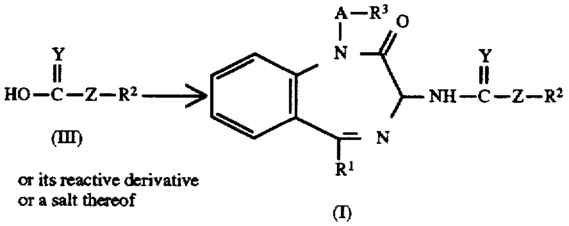

(III)

or its reactive derivative or a salt thereof (I)

or a salt thereof

Process 2

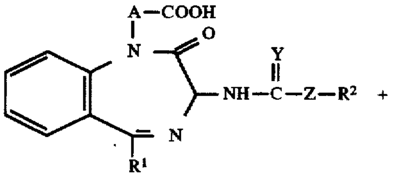

(IV)

or its reactive derivative at the carboxy group or a salt thereof

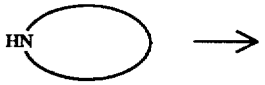

(V)

ot its reactive derivative at the imino group or a salt thereof

-continued

Process 2

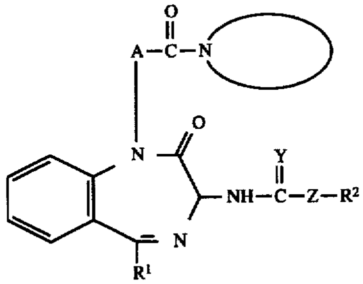

(Ia)

or a salt thereof

Process 3

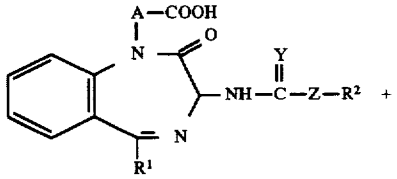

(IV)

or its reactive derivative at the carboxy group or a salt thereof

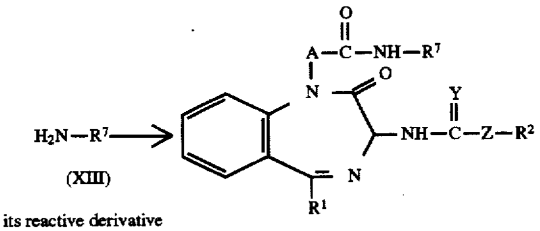

(XIII)

or its reactive derivative at the amino group or a salt thereof (Ib)

wherein $R^1$, $R^2$, $R^3$, A, Y and Z are each as defined above,

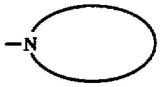

is a bridged heterocyclic group containing at least one nitrogen atom, which may have one or more suitable substituent(s), and $R^7$ is a bridged cyclic-hydrocarbon group The starting compounds (II) and (IV) may be prepared by the following processes.

Process A

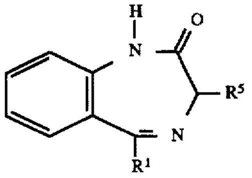

(VI)

or a salt thereof

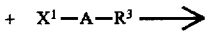

(VII)

or a salt thereof

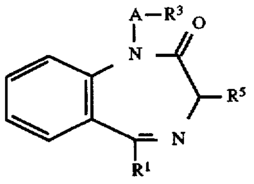

(VIII)

or a salt thereof

Process B

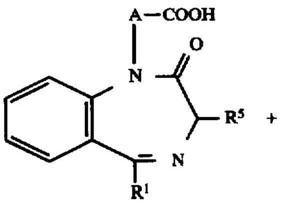

(IX)

or its reactive derivative at the carboxy group or a salt thereof

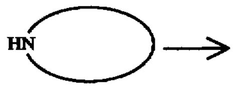

(V)

or its reactive derivative at the imino group or a salt thereof

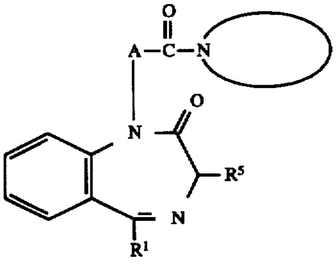

(VIIIa)

or a salt thereof

Process C

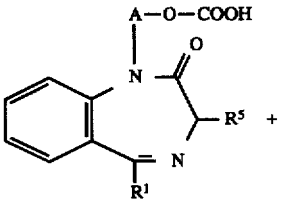

(X)

or its reactive derivative at the carboxy group or a salt thereof

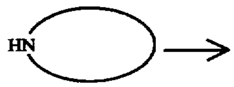

(V)

or its reactive derivative at the imino group or a salt thereof

-continued

Process C

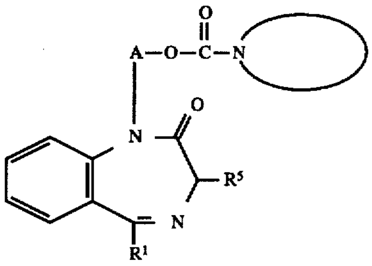

(VIIIb)
or a salt thereof

Process D

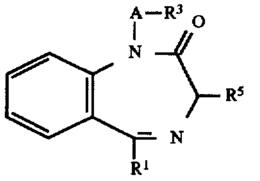

(VIII)
or a salt thereof

Elimination reaction of
the amino protective group

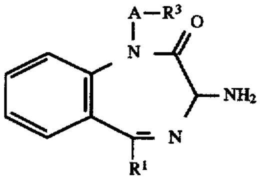

(II)
or a salt thereof

Process E

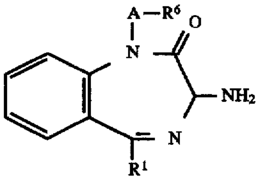

(XI)
or its reactive derivative at the amino group or a salt thereof

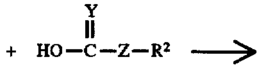

(III)
or its reactive derivative
or a salt thereof

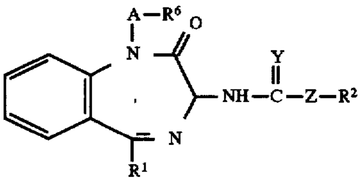

(XII)
or a salt thereof

Process F

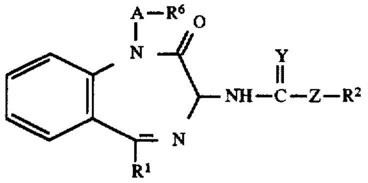

(XII)
or a salt thereof

Elimination reaction of the
carboxy protective group

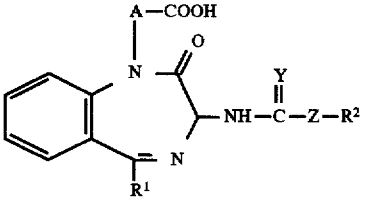

(IV)
or a salt thereof wherein $R^1$, $R^2$, $R^3$,

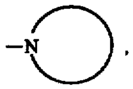

,

A, Y and Z are each as defined above, $R^5$ is protected amino, $R^6$ is protected carboxy, and $X^1$ is halogen.

With regard to the object compound (I), in case that the compound (I) has the group of the formula:

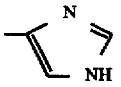

in $R^2$ said group can also exist in the tautomeric form and such tautomeric equilibrium can be represented by the following scheme.

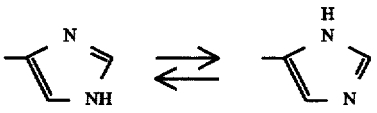

(A) (B)

Both of the above tautomeric isomers are included within the scope of the present invention. In the present specification and claim, the compounds including the group of such tautomeric isomers are represented for the convenient sake by one expression of the group of the formula (A).

Further, in case that the compound (I) has the group of the formula:

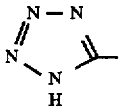

in R2, said group can also exist in the tautomeric from and such tautomeric equilibrium can be represented by the following scheme.

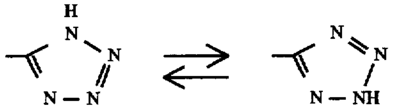

(C) (D)

Both of the above tautomeric isomers are included within the scope of the present invention. In the present specification and claim, the compounds including the group of such tautomeric isomers are represented for the convenient sake by one expression of the group of the formula (C).

BEST MODE FOR CARRYING OUT THE INVENTION

Suitable pharmaceutically acceptable salts of the object compound (I) are conventional non-toxic salts and include a metal salts such as an alkali metal salt (e.g., sodium salt, potassium salt, etc.) and an alkaline earth metal salt (e.g., calcium salt, magnesium salt, etc.), an ammonium salt, an organic base salt (e.g., trimethylamine salt, triethylamine salt, pyridine salt, picoline salt, dicyclohexylamine salt, N,N'-dibenzylethylene diamine salt, etc.), an organic acid salt (e.g., acetate, maleate, tartrate, methanesulfonate, benzenesulfonate, formate, toluenesulfonate, trifluoroacetate, etc.), an inorganic acid salt (e.g., hydrochloride, hydrobromide, sulfate, phosphate, etc.), a salt with an amino acid (e.g., arginine, aspartic acid, glutamic acid, etc.), and the like.

In the above and subsequent descriptions of the present specification, suitable examples and illustrations of the various definitions which the present invention include within the scope thereof are explained in detail as follows.

The term "lower" is intended to mean 1 to 6 carbon atom(s), unless otherwise indicated.

Suitable "aryl" may include phenyl, naphthyl, and the like.

Suitable "substituent" for aryl, $C_3$–$C_8$ cycloalkyl, indanyl or a heterobicyclic group may include acyl (which is exemplified as below), hydroxy, protected hydroxy (e.g., acyloxy, etc., which is exemplified as below), nitro, cyano, lower alkoxy (e.g., methoxy, ethoxy, propoxy, isopropoxy, butoxy, t-butoxy, pentyloxy, t-pentyloxy, hexyloxy, etc.), amino, protected amino (e.g., acylamino, etc., which is exemplified as below), carboxy, protected carboxy (which is exemplified as below), carboxy(lower)alkyl, protected carboxy(lower) alkyl, carboxy(lower)alkoxy, protected carboxy(lower) alkoxy, lower alkyl (e.g., methyl, ethyl, propyl, isopropyl, butyl, isobutyl, sec-butyl, t-butyl, pentyl, t-pentyl, hexyl, etc.), halogen (e.g., chlorine, bromine, fluorine and iodine), lower alkylthio (e.g., methylthio, ethylthio, propylthio, butylthio, pentylthio, etc.), trihalo(lower)alkyl (e.g., trifluoromethyl, trifluoroethyl, trifluoropropyl, trifluorobutyl, trichloromethyl, trichloroethyl, trichloropropyl, trichlorobutyl, etc.), cyclo(lower)alkyl (lower)alkoxy (e.g., cyclopropylmethoxy, 2-cyclopropylethoxy, 3-cyclopropylpropoxy, 4-cyclopropylbutoxy, 5-cyclopropylpentyloxy, etc.), lower alkylthio(lower)alkoxy (e.g., methylthiomethoxy, 2-methylthioethoxy, 3-methylthiopropoxy, 4-methylthiobutoxy, ethylthiomethoxy, 2-ethylthioethoxy, 3-ethylthiopropoxy, 4-ethylthiobutoxy, etc.), lower alkoxy (lower)alkyl (e.g., methoxymethyl, 2-methoxyethyl, 3-methoxypropyl, 4-methoxybutyl, ethoxymethyl, 2-ethoxyethyl, 3-ethoxypropyl, 4-ethoxybutyl, etc.), lower alkanoyl (e.g. formyl, acetyl, etc., which is exemplified as below), lower alkylthio(lower)alkoxycarbonyl (e.g., methylthiomethoxycarbonyl, 2-methylthioethoxycarbonyl, 3-methylthiopropoxycarbonyl, 4-methylthiobutoxycarbonyl, ethylthiomethoxycarbonyl, 2-ethylthioethoxy carbonyl, 3- ethylthiopropoxycarbonyl, 4-ethylthiobutoxyyarbonyl, etc.), lower alkoxyimino(lower) alkyl (e.g., methoxyiminomethyl, ethoxyiminomethyl, propoxyiminomethyl, butoxyiminomethyl, 2-methoxyiminoethyl, 2-ethoxyiminoethyl, propoxyiminoethyl, butoxyiminoethyl, etc.), lower alkoxycarbonyl(lower)alkyl (e.g., methoxycarbonylmethyl, ethoxycarbonylmethyl, etc.), lower alkoxycarbonyl(lower) alkenyl (e.g., 2-methoxycarbonylvinyl, 2-ethoxycarbonylvinyl, 2-propoxycarbonylvinyl, 2-butoxycarbonylvinyl, 3-methoxycarbonyl-1-propenyl, etc.), oxo, hydroxy(lower)alkyl (e.g., hydroxymethyl, hydroxyethyl, etc.), trihalo(lower)alkoxy (e.g., trifluoromethoxy, trichloromethoxyy etc.), carbamoyl, mono or di substituted carbamoyl (which is exemplified as below), dihydroxyboryl, sulfo, sulfo(lower)alkyl (e.g., sulfomethyl, sulfoethyl, etc.), sulfamoyl which may have one or more suitable substituent(s) [such as acyl (exemplified as below), lower alkanesulfonyl (e.g., methanesulfonyl, ethanesulfonyl, etc.), aryl, lower alkyl, etc.], heterocyclic group (which is exemplified as below), heterocyclic(lower) alkyl, wherein "heterocyclic group" in the above terms "heterocyclic group" and "heterocyclic(lower)alkyl" may have one or more suitable substiuent(s) (which is exemplified as below), hydroxyimino(lower)alkyl (e.g., hydroxyiminomethyl, etc.), 1-amino-1-(hydroxy-imino) methyl, lower alkoxy carbonyl(lower)alkoxy, and the like.

Suitable "acyl" in the above terms "acyl", "acyloxy" and "acylamino" may include aliphatic acyl group and acyl group containing an aromatic or heterocyclic ring.

And, suitable examples of the said acyl may be lower alkanoyl (e.g., formyl, acetyl, propionyl, butyryl, isobutyryl, valeryl, isovaleryl, oxalyl, succinyl, pivaloyl, etc.); lower alkoxycarbonyl (e.g., methoxycarbonyl, ethoxycarbonyl, propoxycarbonyl, isopropoxycarbonyl, butoxycarbonyl, tert-butoxycarbonyl, pentyloxycarbonyl, hexyloxycarbonyl, etc.); lower alkanesulfonyl (e.g., mesyl, ethanesulfonyl, propanesulfonyl, isopropanesulfonyl, butanesulfonyl, etc.); arenesulfonyl (e.g., benzenesulfonyl, tosyl, etc.); aroyl (e.g., benzoyl, toluoyl, xyloyl, naphthoyl, phthaloyl, indancarbonyl, etc.); ar(lower)alkanoyl (e.g., phenylacetyl, phenylpropionyl, etc.); ar(lower)alkoxycarbonyl (e.g., benzyloxycarbonyl, phenethyloxycarbonyl, etc.), and the like.

Suitable examples of the said "heterocyclic group" may include saturated or unsaturated, monocyclic or polycyclic heterocyclic group containing at least one hetero-atom such as an oxygen, sulfur, nitrogen atom and the like. And especially preferable heterocyclic group may be heterocyclic group such as unsaturated 3 to 8-membered heteromonocyclic group containing 1 to 4 nitrogen atom(s), for example, pyrrolyl, pyrrolinyl, imidazolyl, pyrazolyl, pyridyl and its N-oxide, pyrimidyl, pyrazinyl, dihydropyridazinyl, tetrahydropyridazinyl, triazolyl (e.g., 1H-1,2,4-triazolyl, 1H-1,2,3-triazolyl, 2H-1,2,3-triazolyl, etc.), tetrazolyl (e.g., 1H-tetrazolyl, 211-tetrazolyl, etc.), dihydrotriazinyl (e.g., 4,5-dihydro-1,2,4-triazinyl, 2,5-dihyclro-1,2,4-triazinyl, etc.), etc., ;

saturated 3 to 8-membered heteromonocyclic group containing 1 to 4 nitrogen atom(s), for example, pyrrolidinyl, imidazolidinyl, piperidino, piperazinyl, etc., ;

unsaturated condensed heterocyclic group containing 1 to 5 nitrogen atom(s), for example, indolyl, isoindolyl, indolinyl, isoindolinyl, indolizynyl, benzimidazolyl, quinolyl, isoquinolyl, indazolyl, benzotriazolyl, tetrazolopyridyl, tetrazolopyridazinyl (e.g., tetrazolo[1,5-b]pyridazinyl, etc.), dihydrotriazolopyridazinyl, etc., ;

unsaturated 3 to 8-membered heteromonocyclic group containing 1 to 2 oxygen atom(s) and 1 to 3 nitrogen atom(s), for example, oxazolyl, isoxazolyl, dihydroisoxazolyl, oxadiazolyl (e.g., 1,2,4-oxadiazolyl, 1,3,4-oxadiazolyl, 2,5-oxadiazolyl, etc.,), etc., ;

saturated 3 to 8-membered heteromonocyclic group containing 1 to 2 oxygen atom(s) and 1 to 3 nitrogen atom(s), for example, morpholinyl, etc., ;

unsaturated condensed heterocyclic group containing 1 to 2 oxgen atom(s) and 1 to 3 nitrogen atom(s), for example, benzoxazolyl, benzoxadiazolyl, etc., ;

unsaturated 3 to 8-membered heteromonocyclic group contaning 1 to 2 sulfur atom(s) and 1 to 3 nitrogen atom(s), for example, 1,3-thiazolyl, 1,2-thiazolyl, thiazolinyl, thiadiazolyl (e.g., 1,2,4--thiadiazolyl, 1,3,4-thiadiazolyl, 1,2,5-thiadiazolyl, 1,2,3-thiadiazolyl), etc.,;

saturated 3 to 8-membered heteromonocyclic group containing 1 to 2 sulfur atom(s) and 1 to 3 nitrogen atom(s), for example, thiazolidinyl, etc.,;

unsaturated 3 to 8-membered heteromonocyclic group containing an oxygen atom, for example furyl, etc., ;

unsaturated 3 to 8-membered heteromonocyclic group containing a sulfur atom, for example, thienyl, etc.,;

unsaturated condensed heteromonocyclic group containing 1 to 2 sulfur atom(s) and 1 to 3 nitrogen atom(s), for example, benzolthiazolyl, benzothiadiazolyl, etc., and the like.

Suitable examples of the said mono or di substituted carbamoyl may be mono or di (lower)alkylcarbamoyl (e.g., methylcarbamoyl, dimethylcarbamoyl, ethylcarbamoyl, diethylcarbamoyl, N-methyl-N-ethylcarbamoyl, propylcarbamoyl, dipropylcarbamoyl, isopropylcarbamoyl, butylcarbamoyl, pentylcarbamoyl, hexylcarbamoyl, etc.), heterocyclic carbamoyl (e.g., tetrazolylcarbamoyl, etc.,), mono or di (carboxy) (lower)alkylcarbamoyl (e.g., carboxymethylcarbamoyl, 1-carboxyethylcarbamoyl, 2-carboxyethylcarbamoyl, 1,3-dicarboxypropylcarbamoyl, etc.,), mono or di (lower alkoxycarbonyl) (lower) alkylcarbamoyl (e.g., 1,3-diethoxycarbonylpropylcarbamoyl, etc.), mono or di (protected carboxy) (lower)alkylcarbamoyl (wherein "protected carboxy" is exemplified as below), mono or di {(lower)alkyl}-amino(lower)alkylcarbamoyl (e.g., 2-dimethylaminoethylcarbamoyl, etc.), and the like.

Suitable "substituent" in the terms "heterocyclic group and heterocyclic(lower)alkyl may have one or more suitable sunstituent(s)" may include amino, protected amino as exemplified above, oxo, hydroxy, imino protective group as exemplified below, lower- alkyl (e.g., methyl, ethyl, propyl, isopropyl, butyl, isobutyl, sec-butyl, t-butyl, pentyl, t-pentyl, hexyl, etc.), and the like.

Suitable "$C_3$–$C_8$ cycloalkyl" may include cyclopropyl, cyclobutyl, cyclopentyl, cyclohexyl, cycloheptyl and cyclooctyl.

Suitable "heterobicyclic group" may include benzo- thiacliazolyl [e.g., 1,2,3-benzothiadiazolyl (e.g., 1,2,3-benzothiacliazol-4-yl, 1,2,3-benzothiadiazol-5-yl, etc.) or 2,1,3-benzcthiadiazolyl (e.g., 2,1,3-benzothiadiazol-4-yl, 2,1,3-benzothiadiazol-5-yl, etc.)], benzodioxanyl [e.g., 1,4-benzodioxanyl (e.g., 1,4-benzodioxan-5-yl, 1,4-benzodioxan-6-yl, etc.), 1,3-benzodioxanyl (e.g., 1,3-benzodioxan-5-yl, 1,3-benzodioxan-6-yl, etc.)], tetrahydroquinolyl [e.g., 1,2,3,4-tetrahydroquinolyl (e.g., 1,2,3,4-tetrahydroquinolin-5-yl, 1,2,3,4-tetrahydroquinolin-6-yl, etc.), etc.], methylenedioxyphenyl (e.g., 2,3-methylenedioxyphenyl, 3,4-methylenedioxyphenyl, etc.), indolyl (e.g., 4-indolyl, 5-indolyl, 6-indolyl, etc.), indazolyl (e.g., 4-indazolyl, 5-indazolyl, 6-indazolyl, etc.), and the like.

Suitable "substituent" in the terms "heterocyclic group selected from the group consisting of tetrahydrofuryl, dioxolanyl, furyl, thienyl, isoxazolyl, pyridyl, benzimidazolyl, benzothiazolyl, benzoxazolyl, benzopyranyl, quinolyl, isoquinolyl, tetrahydroisoquinolyl, benzothienyl and benzofuryl, each of which may have one or more suitable substituent(s)" and "a bridged heterocyclic group containing at least one nitrogen atom, which may have one or more suitable substituent(s)" may include amino, protected amino as exemplified above, oxo, hydroxy, imino protective group as exemplified below, lower alkyl (e.g., methyl, ethyl, propyl, isopropyl, butyl, isobutyl, sec-butyl, t-butyl, pentyl, t-pentyl, hexyl, etc.), oxy, halogen as exemplified above, lower alkoxy as exemplified above, lower alkanoyl as exemplified above, heterocyclic carbonyl (e.g., pyrrolidinyl-carbonyl, etc.), carboxy, protected carboxy as exemplified below, carbamoyl, mono or di(lower)alkyl substituted carbamoyl as exemplified above, acyl as exemplified above, bridged N-containing heterocyclic carbonyl (wherein the "bridged N-containing heterocyclic" can be referred to "bridged heterocyclic group containing at least one nitrogen atom" as exemplified below), ar(lower)alkyl (e.g., benzyl, phenetlhyl, etc.), and the like.

Suitable examples of the said "imino protective group" may include acyl as exemplified above, mono(or di or tri)phenyl(lower)alkyl (e.g., benzyl, trityl, etc.), tetrahydropyranyrl, and the like.

Suitable "bridged heterocyclic group containing at least one nitrogen atom" may include 2-azabicyclo[2.2.1]hept-2-yl, 2-azabiclo[2.2.2]oct-2-yl, 2-azabicyclo[2.2.1]hept-5-en-2-yl, 2-azabicyclo[2.2.2]oct-5-en-2-yl, 2,5-diazabicyclo[2.2.1]hept-2-yl, 2,5-diazabicyclo[2.2.2]oct-2-yl, 2,5-diazabicyclo[2.2.2]hept-5-en-2-yl, 2,5-diazabicyclo[2.2.2]oct-5-en-2-yl, 3-azabicyclo[3.2.1]oct-3-yl, 3-azabicyclo[3.2.2]non-3-yl, 6-azabicyclo[3.2.1]oct-6-yl, 6-azabicyclo[3.2.2]non-6-yl, 3,6-diazabicyclo[3.2.1]oct-3-yl, 3,8-diazabicyclo[[3.2.1]oct-3-yl, 3,6-diazabicyclo[3.2.2]non-3-yl, 3,6-dilazabicyclo[3.2.1]oct-6-yl, 3,6-diazabicyclo[3.2.2]non-6-yl, 3-azabi icyclo[3.2.1]oct-6-en-3-yl, 3-azabicyclo[3.2.2]non-6-en-3-yl, 6-azabicyclo[3.2.1]oct-2-en-6-yl, 6-azabicyclo[3.2.2]non-2-en-6-yl, 3,6-diazabicyclo[3.2.1]oct-6-en-3-yl, 3,6-diazabicyclo[3.2.2]non-6-en-3-yl, 3,6-diazabicyclo[3.2.1]oct-2-en-6-yl, 3,6-diazabicyclo[3.2.2]non-2-en-6-yl, 2-azatricyclo[4.3.1.$1^{4,8}$]undec-2-yl, 5-azatricyclo[4.3.1.$1^{4,8}$]undec-5-yl, 7-azatricyclo[4.3.1.$1^{4,8}$]undec-7-yl, 9-azatricyclo[4.3.1]$^{4,8}$]undec-9-yl, and the like.

Suitable "lower alkylene" may include straight or branched one having 1 to 6 carbon atom(s), such as methylene, ethylene, trimethylene, tetramethylene, pentamethylene, hexamethylene, or the like, preferably one having 1 to 4 carbon atom(s).

Suitable "bridged cyclic-hydrocarbon group" may include bicyclo[2.2.1]hept-2-yl, bicyclo[3.2.1]oct-2-yl, bicyclo

[3.2.2]non-2-yl, bicyclo[3.2.2]non-3-yl, bicyclo[4.3.2]undec-2-yl, bicyclo[4.3.2]undec-3-yl, bicyclo[2.2.2]oct-2-en-2-yl, bicyclo[3.2.2]non-3-en-3-yl, tricyclo[5.3.1.1]dodec-2-yl, tricyclo[5.3.11]dodec-3-yl, adamantyl, and the like.

Suitable "protected carboxy" may include esterified carboxy and the like.

Suitable example of the ester moiety of an esterified carboxy may be the ones such as lower alkyl ester (e.g. methyl ester, ethyl ester, propyl ester, isopropyl ester, butyl ester, isobutyl ester, tert-butyl ester, pentyl ester, hexyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, l(or 2 or 3)-acetoxypropyl ester, 1 (or 2 or 3 or 4)-acetoxybutyl ester, 1 (or 2)-propionyloxyethyl ester, l(or 2 or 3)-propionyloxypropyl ester, 1(or 2)-butyryloxyethyl ester, 1(or 2)-isobutyryloxymethyl ester, 1(or 2)-pivaloyloxyethyl ester, 1(or 2)-hexanoyloxyethyl ester, iso-butyryloxymethyl ester, 2-ethylbutyryloxymethyl ester, 3,3-dimethtylbutyryloxymethyl ester, 1(or 2)-pentanoyloxyethyl ester, etc.], lower alkanesulfonyl (lower)alkyl ester (e.g. 2-mesylethyl ester, etc.), mono(or di or tri)-halo(lower)alkyl ester (e.g. 2-iodoethly ester, 2,2,2-trichloroethyl ester, etc.), lower alkoxycarbonyloxy(lower) alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), lower alkylthio (lower)alkyl ester (e.g. methylthiomethyl ester, 1-(or 2-)methylthioethyl ester, 1-(or 2-or 3-)methylthiopropyl ester, 1-(or 2- or 3- or 4-)methylthiobutyl ester, 1-(or 2- or 3- or 4- or 5-)methylthiopentyl ester, 1-(or 2- or 3- or 4- or 5- or 6-)methylthiohexyl ester, ethylthionethyl ester, 1-(or 2-)ethylthioethyl ester, 1-(or 2- or 3-)ethylthiopropyl ester, propylthiomethyl ester, 1-(or 2-) propylthioethyl ester, 1-(or 2- or 3-)propylthiopropyl ester, etc.), phthalidylidene(lower) alkyl ester, or (5-lower alkyl 2-oxo-1,3-dioxol-4-yl)(lower) alkyl ester [e.g. (5-methyl-2-oxo-1,3-dioxol-4-yl)methyl ester, (5-ethyl-2-oxo-1,3-dioxol-4-yl)miethyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) such as mono(or di or tri)phenyl(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl) methyl ester, 3,4-dimethoxybenzyl ester, 4-hydroxy-3,5-di-tert-butylbenzyl ester, etc.); aryl ester which may have at least one suitable substituent(s) (e.g. phenyl ester, 4-chlorophenyl ester, tolyl ester, tert-butylphenyl ester, xylyl ester, mesityl ester, cumenyl ester, etc.); phthalidyl ester; and the like.

The preferred embodiments of the object compound (I) are as follows:

wherein $R^1$ is aryl which may have one or more halogen (s); cyclohexyl; cyclopentyl; or cycloheptyl;

$R^2$ is cyclohexyl; indanyl; or aryl or heterobicyclic group, each of which may have one or more substituent(s) selected from the group consisting of lower alkyl; lower alkylthio; halogen; trihalo(lower) alkyl; lower alkoxy; cyclo(lower)alkyl(lower) alkoxy; lower alkylthio(lower)alkoxy; lower alkoxy (lower)alkyl; hydroxy; lower alkanoyl; lower alkylthio(lower)alkoxycarbonyl lower alkoxyimino (lower)alkyl; lower alkoxycarbonyl(lower)alkenyl; oxo; amino; lower alkanoylamino; lower alkoxycarbonyl; lower alkoxycarbonyl(lower)alkyl; cyano; nitro; hydroxy(lower)alkyl; trihalo(lower)alkoxy; carbamoyl which may be substituted with one or two substituents selected from the group consisting of lower alkyl; tetrazolyl; mono or di carboxy(lower) alkyl; mono or di (lower alkoxycarbonyl)(lower) alkyl and phenyl(lower)alkoxycarbonyl(lower)alkyl; dihydroxyboryl; sulfo(lower)alkyl; sulfo; sulfamoyl whcih may have one or more substituent(s) selected from the group consisting of lower alkanoyl, lower alkanesulfonyl, phenyl and lower alkyl; oxodihydropyridazinyl; oxo-dihydrooxadiazolyl; tetrazolyl; tetrazolyl(lower)alkyl; carboxy; carboxy(lower) alkyl; carboxy(lower)alkoxy; hydroxyimino(lower) alkyl; 1-amino-1-(hydroxyimino)methyl; and lower alkoxycarbonyl(lower)alkoxy;

A is lower alkylene;

$R^3$ is a heterocyclic group selected from the group consisting of tetrahydrofuryl, dioxolanyl, furyl, thienyl, isoxazolyl, pyridyl, benzimidazolyl, benzothiazolyl, benzoxazolyl, benzopyranyl, quinolyl, isoquinolyl, tetrahydroisoquinolyl, benzothienyl and benzofuryl, each of which may have one or more substituent(s) selected from the group consisting of lower alkyl, oxo, lower alkoxy, lower alkanoyl, halogen, pyrrolidinylcarbonyl, oxy, lower alkoxycarbonyl, carboxy, carbamoyl, moro or di {(lower)alkyl}-amino(lower)alkylcarbamoyl and bridged N-containing heterocyclic carbonyl; or a group of the formula: —X—$R^4$

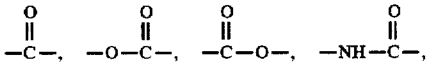

or

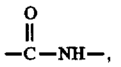

and $R^4$ is thiomorpholinyl; pyridyl; a bridged heterocyclic group containing at least one nitrogen atom, which may have one or more substituent(s) selected from the group consisting of lower alkyl and phenyl(lower)alkyl; or a bridged cyclic-hydrocarbon group);

Y is O or S, and

—Z— is direct single bond between carbon and $R^2$, or

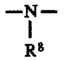

(in which $R^8$ is hydrogen or lower alkyl), or a pharmaceutically acceptable salt thereof.

The more preferred embodiment of the object compound (I) are as follows:

wherein $R^1$ is phenyl which may have one or more halogen(s); cyclohexyl; cyclopentyl; or cycloheptyl;

$R^2$ is cyclohexyl; indanyl; or phenyl, benzothiadiazolyl, benzodioxanyl, indazolyl, tetrahydroquinolyl, methylenedioxyphenyl or indolyl, each of which may have one or more substituent(s) selected from the group consisting of lower alkyl; lower alkylthio; halogen; trihalo(lower) alkyl; lower alkoxy; cyclo(lower)alkyl(lower) alkoxy; lower alkylthio(lower)alkoxy; lower alkoxy (lower)alkyl; hydroxy; lower alkanoyl; lower alkylthio(lower)alkoxycarbonyl; lower alkoxyimino (lower)alkyl; lower alkoxycarbonyl(lower)alkenyl; oxo; amino; lower alkanoylamino; lower alkoxycarbonyl; lower alkoxycarbonyl(lower)alkyl; cyano; nitro; hydroxy(lower)alkyl; trihalo(lower)alkoxy; carbamoyl which may be substituted with one or two substituent(s) selected from the group consisting of lower alkyl, tetrazolyl, mono or di carboxy(lower) alkyl, mono or di (loweralkoxycarbonyl)(lower) alkyl and phenyl(lower)alkoxycarbonyl(lower)alkyl; dihydroxyboryl; sulfo(lower)alkyl; sulfo; sulfamoyl which may have one or more substituent(s) selected from the group consisting of lower alkanoyl, lower alkanesulfonyl, phenyl and lower alkyl; oxo-dihydropyridazinyl; oxo-dihydrooxadiazolyl; tetrazolyl; tetrazolyl(lower)alkyl; carboxy; carboxy (lower)alkyl; carboxy(lower)alkoxy; hydroxyimino (lower)alkyl; 1-amino-1-(hydroxyimino)methyl; and lower alkoxycarbonyl(lower)alkoxy;

A is methylene or ethylene;

$R^3$ is a heterocyclic group selected from the group consisting of tetrahydrofuryl, dioxolanyl, furyl, thienyl, isoxazolyl, pyridyl, benzimidazolyl, benzothiazolyl, benzoxazolyl, benzopyranyl, quinolyl, isoquinolyl, tetrahydroisoquinolyl, benzothienyl and benzofuryl, each of which may have one or more substituent(s) selected from the group consisting of lower alkyl, oxo, lower alkoxy, lower alkanoyl, halogen, pyrrolidinylcarbonyl, oxy, lower alkoxycarbonyl, carboxy, carbamoyl, moro or di {(lower)alkyl}-amino(lower)alkylcarbamoyl and bridged N-containing heterocyclic carbonyl; or a group of the formula : —X—$R^4$

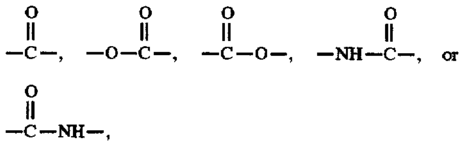

and $R^4$ is thiomorpholinyl; pyridyl; 3-azabicyclo [3.2.2]non-3-yl, 6-azabicyclo[3.2.1]oct-6-yl, 2-azabicyclo[2.2.1]hept-5-en-2-yl, 2-azabicyclo [2.2.1]hept-2-yl, 2,5-diazabicyclo[2.2.1]hept-2-yl, 3,8-diazabicyclo[3.2.1]oct-3-yl or 2-azatricyclo [$4.3.1.1^{4,8}$]undec-2-yl, each of which may have one or more substituent(s) selected from the group consisting of lower alkyl and phenyl(lower)alkyl; or adamantyl)

Y is O or S, and

—Z— is direct single bond between carbon and $R^2$, or

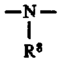

(in which $R^8$ is hydrogen or methyl), or a pharmaceutically acceptable salt thereof.

And more preferred embodiments of the object compound (I) are as follows:

wherein $R^1$ is phenyl which may have one or more fluorine(s); cyclohexyl; cyclopentyl; or cycloheptyl;

$R^2$ is cyclohexyl; indanyl; or phenyl, benzothiadiazolyl, benzodioxanyl, indazolyl, tetrahydroquinolyl, methylenedioxyphenyl or indolyl, each of which may have one or more substituent(s) selected from the group consisting of methyl, ethyl, methylthio, fluorine, chlorine, bromine, trifluoromethyl, methoxy, cyclopropylmethoxy, methylthioethoxy, methoxyethyl, hydroxy, acetyl, methylthioethoxycarbonyl, methoxyiminomethyl, methoxycarbonylvinyl, phenylsulfamoyl, dimethylsulfamoyl, trifluoromethoxy, ethoxy, formyl, hydroxymethyl, amino, acetylamino, carbamoyl, methylcarbamoyl, oxo-dihydropyridazinyl, dihydroxyboryl, sulfomethyl, sulfo, sulfoethyl, terazolylcarbamoyl, carboxyethyl, oxo-dihydrooxadiazolyl, acetylsulfamoyl, methanesulfonylsulfamoyl, hydroxyiminomethyl, carboxymethoxy, ethoxycarbonylmethoxy, 1-amino-1-(hydroxyimino)methyl, methoxycarbonyl, carboxy, methoxycarbonylmethyl, carboxymethyl, tetrazolyl, tetrazolylmethyl, benzyloxycarbonylmethylcarbamoyl, carboxymethylcarbamoyl, benzyloxycarbonylethylcarbamoyl, carboxyethylcarbamoyl, di(ethoxycarbonyl) propylcarbamoyl, di(carboxy)propylcarbamoyl, sulfamoyl, cyano, nitro, and t-butoxycarbonyl;

A is methylene or ethylene;

$R^3$ is a heterocyclic group selected from the group consisting of tetrahydrofuryl, dioxolanyl, furyl, thienyl, isoxazolyl, pyridyl, benzimidazolyl, benzothiazolyl, benzoxazolyl, benzopyranyl, quinolyl, isoquinolyl, tetrahydroisoquinolyl, benzothienyl and benzofuryl, each of which may have one or more substituent(s) selected from the group consisting of methyl, methoxy, chlorine, oxy, methoxycarbonyl, oxo, pyrrolidinylcarbonyl, carboxy, aminocarbonyl, acetyl, (3-azabicyclo[3.2.2] non-3-yl)carbonyl, dimethylaminoethylaminocarbonyl and t-butyl; or a group of the formula : —X—$R^4$

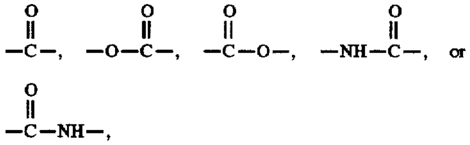

and $R^4$ is thiomorpholinyl; pyridyl; 3-azabicyclo [3.2.2]non-3-yl, 6-azabicyclo[3.2.1]oct-6-yl, 2-azabicyclo[2.2.1]hept-5-en-2-yl, 2-azabicyclo [2.2.1]hept-2-yl, 2,5-diazabicyclo[2.2.1]hept-2-yl, 3,8-diazabicyclo[3.2.1]oct-3-yl or 2-azatricyclo [$4.3.1.1^{4,8}$]undec-2-yl, each of which may have one or more substituent(s) selected from the group consisting of benzyl and methyl; or adamanty);

Y is O or S, and

—Z— is direct single bond between carbon and $R^2$, or

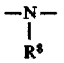

(in which $R^8$ is hydrogen or methyl), or a pharmaceutically acceptable salt thereof.

The processes for preparing the object compound (I) and the starting compounds of the present invention are explained in detail in the following.

Process 1:

The compound (I) or a salt thereof can be prepared by reacting the compound (II) or its reactive derivative at the amino group or a salt thereof with the compound (III) or its reactive derivative or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as N,N-bis(trimethylsilyl)acetamide, N-trimethylsilylacetamide or the like; a derivative formed by the reaction of the compound (II) with phosphorus trichloride or phosgene and the like.

Suitable reactive derivative of the compound (III) may include an acid halide, an acid anhydride, a thioacid anhydride, an activated amide, an activated thioamide, an activated ester, an activated thioester, isocyanate, isothiocyanate, and the like. The suitable example may be an acid chloride, a thioyl chloride, an acid azide; a mixed acid anhydride or mixed thioacid anhidride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfonic acid, (e.g., methanesulfonic acid, ethanesulfonic acid, etc.), sulfuric acid, alkylcarbonic acid, aliphatic carboxylic acid (e.g., pivalic acid, pentanoic acid, isopentanoic acid, 2-ethylbutyric acid, trichloroacetic acid, etc.) or aromatic carboxylic acid (e.g., benzoic acid, etc.); a symmetrical acid anhydride; an activated amide or an activated thioamide with imidazole, 4-substituted imidazole, dimethylpyrazole, triazole or tetrazole; an activated ester or an activated thioester (e.g., cyanomethyl ester, methoxymethyl ester, dimethyliminomethyl $[(CH_3)_2N^+{=}CH{-}]$ ester, vinyl ester, propargyl ester, phenyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thiogester, pyranyl ester, pyridyl ester, piperidyl ester, 8-quinolyl thioester, etc.); an ester with a N-hydroxy compound (e.g., N,N-dimethylhydroxylamine, 1-hydroxy-2-(1H)-pyridone, N-hydroxy-succinimide, N-hydroxybenzotriazole, N-hydroxyphtalimide, 1-hydroxy-6-chloro-1H1-benzotriazole, etc.); isocyanate or isothiocyanate of the formula : $R^2{-}N{=}C{=}Y$ (in which $R^2$ and Y are as defined above), and the like. These reactive derivatives can optionally be selected according to the kind of the compound (III) to be used.

Suitable salts of the compounds (II) and (III) can be referred to the ones as exemplified for the compound (I).

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely affect the reaction. These conventional solvents may also be used in a mixture with water.

When the compound (III) is used in free acid form or its salt form in the reaction, the reaction is preferably carried out in the presence of a conventional condensing agent such as N,N'-dicyclohexylcarbodiimide; N-cycloheyxl-N'-morpholinoethylcarbodiimide; N-cyclohexyl-N'-(4-diethylaminocyclohexyl) carbodiimide; N,N'-diethylcarobodiimide, N,N'-diisopropylcarbodiimide; N-ethyl-N'-(3-dimethylaminopropyl)carbodiimide; N,N'-carbonylbis-(2-methylimidazole); N,N'-carbonyldiimidazole, pentamethyleneketene-N-cyclohexylimine; diphenylketene-N-cyclohexylimine; ethoxyacetylene; 1-alkoxy-1-chloroethylene; trialkl phosphate; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower) aklylmorphorine, N,N-di(lower)alkylbenzylamine, or the like. The reaction temperature is not critical, and the reaction is usually carried out under cooling to heating.

The compound (III) or its reactive derivate, or a salt thereof can be prepared in accordance with the method disclosed in the Preparations described later or similar manners thereto.

Process 2

The compound (Ia) or a salt thereof can be prepared by reacting the compound (IV) or its reactive derivative at the carboxy group or a salt thereof with the compound (V) or its reactive derivative at the imino group or a salt thereof.

Suitable reactive derivative at the carboxy group of the compound (IV) may include the same one as illustrated in the explanation of the Process 1.

Suitable reactive derivative at the imino group of the compound (V) may be adequately selected from the reactive derivative at the amino group that is illustrated in the explanation for the Process 1.

Suitable salts of the compounds (IV) and (V) can be referred to the ones as exemplified for the compound (I).

The reaction is usually carried out in the presence of base.

Suitable base may include an inorganic base such as alkali metal hydride (e.g., sodium hydride, etc.), alkali metal hydroxide (e.g., sodium hydroxide, potassium hydroxide, etc.), alkaline earth metal hydroxide (e.g., magnesium hydroxide, calcium hydroxide, etc.), alkali metal carbonate (e.g., sodium carbonate, potassium carbonate, etc.), alkaline earth metal carbonate (e.g., magnesium carbonate, calcium carbonate, etc.), alkali metal bicarbonate (e.g., sodium bicarbonate, potassium bicarbonate, etc.), alkali metal acetate (e.g., sodium acetate, potassium acetate, etc.), alkaline earth metal phosphate (e.g., magnesium phosphate, calcium phosphate, etc.), alkali metal hydrogen phosphate (e.g., disodium hydrogen phosphate, dipotassium hydrogen phosphate, etc.), or the like, and an organic base such as trialkylamine (e.g., trimethylamine, triethylamine etc.), picoline, N-methylpyrrolidine, N-methylmorpholine, or the like.

The reaction is usually carried out in a solvent such as alcohol (e.g., methanol, ethanol, etc.), benzene, N,N-dimethylformalmide, tetrahydrofuran, diethyl ether or any other solvent which does not adversely affect the reaction.

The reaction temperature is not critical and the reaction is usually carried out under cooling to heating.

Process 3

The compound (Ib) or a salt thereof can be prepared by reacting the compound (IV) or its reactive derivative at the carboxy group or a salt thereof with the compound (XIII) or its reactive derivative at the amino group or a salt thereof.

Suitable reactive derivative at the carboxy group of the compound (IV) and suitable reactive derivative at the amino group of the compound (XIII) may include the same one as illustrated in the explanation of the Process 1.

Suitable salts of the compounds (IV) and (XIII) can be referred to the ones as exemplified for the compound (I).

The reaction can be referred to that of the aforementioned Process 2.

Process A

The compound (VIII) or a salt thereof can be prepared by reacting the compound (VI) or a salt thereof with the compound (VII) or a salt thereof. This reaction can be referred to that of Preparations 1-1, 2-1, 3-1, and 4-1.

Process B

The compound (VIIIa) or a salt thereof can be prepared by reacting the compound (IX) or its reactive derivative at the carboxy group or a salt thereof with the compound (V) or its reactive derivative at the imino group or a salt thereof. This reaction can be referred to that of aforementioned Process 2.

Process C

The compound (VIIIb) or a salt thereof can be prepared by reacting the compound (X) or its reactive derivative at the carboxy group or a salt thereof with the compound (V) or its reactive derivative at the imino group or a salt thereof. This reaction can be referred to that of aforementioned Process 2.

Process D

The compound (II) or a salt thereof can be prepared by subjecting the compound (VIII) or a salt thereof to elimination reaction of the amino protective group. This elimination reaction can be referred to that of Preparations 1-2, 2-2 and 5-2.

Process E

The compound (XII) or a salt thereof can be prepared by reacting the compound (XI) or its reactive derivative at the amino group or a salt thereof with the compound (III) or its reactive derivative or a salt thereof. This reaction can be referred to that of aforementioned Process 1.

Process F

The compound (IV) or a salt thereof can be prepared by subjecting the compound (XII) or a salt thereof to elimination reaction of the carboxy protective group. This elimination reaction can be referred to that of Preparation 18-4.

The object compound (I) and pharmaceutically acceptable salts thereof are selective CCK-B antagonists or CCK-A/B antagonists.

Further, it is expected that the object compound (I) and pharmaceutically acceptable salts thereof have gastrin antagonism and are useful as therapeutical and/or preventive agents for ulcers, excess gastric secretion, zollinger-Ellison Syndrome, etc.

In order to show the utility of the object compound (I), pharmacological activity of the representative compound thereof is shown in the following.

[I] Test compound

N-[(3RS)-1-[3-azabicyclo[3.2.2]non-3-yl)carbonylmethyl]-2,3-dihydro-5-(2-fluorophenyl)-2-oxo-1H-1,4-benzodiazepin-3-yl]-N'-(3-methylphenyl)urea

[II] Test:

$[^{125}]$ CCK-8 binding to guinea-pig cerebral cortical membranes

Test method (i) Membrane preparation

Guinea-pings were killed by decapitation and bled to death. Cerebral cortex was removed, minced in a small quantity of 50 mM Tris-HCl buffer (pH 7.4), and homogenized in 20 vol. of the buffer by a glass-teflon homogenizer. The homogenate was centrifuged at 30000×g (16000 rpm) for 10 minutes. The pellet was then resuspended in the same buffer by a glass-teflon homogenizer and recentrifuged at 30000×g for 10 minutes. This procedure (washings) was repeated twice more. The final pellet (membrane) was suspended in incubation medium (see below) so as to obtain a final protein concentration of 4 mg/ml and frozen at −80° C. All manipulations were done at 0°–4° C.

(ii) Receptor binding assay

The composition of incubation medium was as follows: 10 mM HEPES (pH 6.5), 5 mM $MgCl_2$, 1 mM EGTA, 130 mM NaCl and 0.25 mg/ml bacitracin. Frozen membranes were thawed and aliquots (400 μg protein) were incubated for 60 minutes under shaking at 370° C. in plastic tubes in 500 μL of incubation medium with 50 pM $^{125}$I-CCK-8 in the presence or absence of test compound ($1\times10^8$ M). To determine the non-specific binding, CCK-8 at 1 μM was added. Each assay was performed in duplicate. Reaction mixture was filtered through a Whatman GF/B glass filter to stop the reaction. After washing the filter with 50 mM Tris-HCl (pH 7.4) buffer containing 0.1 % BSA, the radioactivity of the filter was countered. Non-specific binding was subtracted from total binding to yield specific binding. The effect of the test compound was expressed as % inhibition of specific $^{125}$I-CCK-8 binding.

Test Result

Inhibition (%): 98.0

The object compound (I) or pharmaceutically acceptable salts thereof can usually be administered to mammals including human being in the form of a conventional pharmaceutical composition such as capsule, micro-capsule, tablet, granule, powder, troche, syrup, aerosol, inhalation, solution, injection, suspension, emulsion, suppository or the like.

The pharmaceutical composition of this invention can contain various organic or inorganic carrier materials, which are conventionally used for pharmaceutical purpose, such as excipient (e.g., sucrose, starch, mannit, sorbit, lactose, glucose, cellulose, talc, calcium phosphate, calcium carbonate, etc.), binding agent (cellulose, methyl cellulose, hydroxypropyl cellulose, polypropylpyrrolidone, gelatin, gum arabic, polyethyleneglycol, sucrose, starch, etc.), disintegrator (e.g., starch, carboxy-methyl cellulose, calcium salt of carboxymethyl cellulose, hydroxypropylstarch, sodium glycole-starch, sodium bicarbonate, calcium phosphate, calcium citrate, etc.), lubricant (e.g., magnesium stearate, talc, sodium laurylsulfate, etc.), flavoring agent (e.g., citric acid, menthol, glycine, orange powders, etc.), preservative (e.g., sodium benzoate, sodium bisulfite, methylparaben, propylparaben, etc.), stabilizer (e.g., citric acid, sodium citrate, acetic acid, etc.), suspending agent (e.g., methyl cellulose, polyvinylpyrrolidone, aluminum stearate, etc.), dispersing agent, aqueous diluting agent (e.g., water), base wax (e.g., cacao butter, polyethyleneglycol, white petrolatum, etc.).

The effective ingredient may usually be administered with a unit dose of 0.01 mg/kg to 50 mg/kg, 1 to 4 times a day. However, the above dosage may be increased or decreased according to age, weight, conditions of the patient or the administering method.

The following Preparations and Examples are given only for the purpose of illustrating the present invention in more detail.

Preparation 1-1

To a suspension of sodium hydride (0.11 g of a 60% dispersion in mineral oil) in N,N-dimethylformamide (20 ml) was added gradually (3RS)-2,3-dihydro-5-(2-fluorophenyl)-3-phthalimido-1H-1,4-benzodiazepin-2-one (1.00 g) under nitrogen atmosphere at cooling in an ice-bath. The mixture was stirred under the same condition for 0.5 hour and at ambient temperature for 1 hour. The mixture was cooled in an ice-bath and a solution of 6-bromomethyl coumarin (0.66 g) in N,N-dimethylformamide (5 ml) was added dropwise thereto. The mixture was stirred for 1 hour at the same temperature and at ambient temperature overnight. To the reaction mixture was added acetic acid (0.5 g) under cooling in an ice-bath. The resultant mixture was poured into a mixture of ethyl acetate (100 ml) and water (50 ml) under stirring. The mixture was adjusted to pH 7.5 with sodium bicarbonate. The organic layer was separated. The aqueous layer was extracted with ethyl acetate (50 ml). The combined organic layer was washed with a brine (30 ml), dried over magnesium sulfate, filtered and concentrated in vacuo to afford a crude product. The crude product was purified by column chromatography on silica gel (eluent : $CHCL_3$) to afford (3RS)-2,3-dihydro-5-(2-fluorophenyl)-1-(2-oxo-2H-1-benzopyran-6-yl)methyl-3-phthalimido-1H-1,4-benzodiazepin-2-one as a colorless crystalline solid (1.30 g).

$^1$-NMR (DMSO-$d_6$,δ): 5.17 (1H, d, J=15.6 Hz), 5.71 (1H, d, J=15.6 Hz), 5.85 (1H, s), 6.46 (2H, d, J=10.0 Hz), 7.00–8.00 (15H, m)

Preparation 1-2

To a suspension of (3RS)-2,3-dihydro-5-(2-flurophenyl)-1-(2-oxo-2H-1-benzopyran-6-yl)methyl-3-phthalimido-1H-1,4-benzodiazepin-2-one (1.30 g) in THF (50 ml) was added dropwise hydrazine monohydrate (0.12 g) under stirring at ambient temperature. The mixture was stirred for 2 hours at the same temperature and refluxed under stirring for 2 hours. The reaction mixture was cooled in an ice-bath. The resultant precipitates were filtered off and washed with THF. The filtrate and washing were combined and concentrated in vacuo to afford a residue. The residue was dissolved into chloroform (100 ml) and extracted with 1N-HCl aqueous solution (2×25 ml). The aqueous layer was alkalined with sodium bicarbonate, extracted with chloroform (2×100 ml), dried over magnesium sulfate and filtered. The filtrate was concentrated in vacuo to afford a crude product. The crude product was purified by column chromatography on silica gel with an eluent of a mixture of chloroform and ethyl acetate to afford (3RS)-3-amino-2,3-dihydro-5-(2-fluorophenyl)-1-(2-oxo-2H-1-benzopyran-6-yl)methyl-1H-1,4-benzodiazepin-2-one as a colorless crystalline solid (0.30 g).

$^1$H-NMR ($CDCl_3$,δ): 2.00 (2H, br), 4.63 (1H, s), 4.92 (1H, d, J=15.5 Hz), 5.68 (1H, d, J=15.5 Hz), 6.32(1H, d, J=8.1 Hz), 7.00 (1H, t, J=8.1 Hz), 7.11–7.62 (11 H, m)

Preparation 2-1

To a suspension of sodium hydride (0.11 g of a 60% dispersion in mineral oil) in N,N-dimethylformamide (20 ml) was added gradually (3RS)-2,3-dihydro-5-(2-fluorophenyl)-3-phthalimido-1H-1,4-benzodiazepin-2-one (1.00 g) under nitrogen atmosphere at cooling in an ice-bath. The mixture was stirred under the same condition for 0.5 hour and at ambient temperature for 1 hour. The mixture was cooled in an ice-bath and a solution of 2-bromomethylbenzothiazole (0.63 g) in N,N-dimethylformamide (5 ml) was added dropwise thereto. The mixture was stirred for 1 hour at the same temperature and at ambient temperature overnight. To the reaction mixture was added acetic acid (0.5 g) under cooling in an ice-bath. The resultant mixture was poured into a mixture of ethyl acetate (100 ml) and water (50 ml) under stirring. The mixture was adjusted to pH 7.5–8.0 with sodium bicarbonate. The organic layer was separated. The aqueous layer was extracted with ethyl acetate (50 ml). The combined organic layer was washed with a brine (50 ml), dried over magnesium sulfate, filtered and concentrated in vacuo to afford (3RS)-1-(benzothiazol-2 -yl)methyl-2,3-dihydro-5-(2-fluorophenyl)-3-phthalimido-1H-1,4-benzodiazepin-2-one. This product was allowed to use in a next reaction step without further purification.

$^1$H-NMR (DMSO-$d_6$,δ): 5.70 (2H, q) , 5.89 (1H, s), 7.22–8.10 (16H, m)

Preparation 2-2

To a suspension of (3RS)-1-(benzothiazol-2-yl)methyl-2,3-dihydro-5-(2-fluorophenyl)-3-phthalimido-1H-1,4-benzodiazepin-2-one (1.30 g) in THF (50 ml) was added dropwise hydrazine monohydrate (0.12 g) under stirring at ambient temperature. The mixture was stirred for 2 hours at the same temperature and refluxed under stirring for 2 hours. The reaction mixture was cooled in an ice-bath. The resultant precipitates were filtered off atad washed with THF (30 ml). The filtrate and washing were combined and concentrated in vacuo to afford a crude product. The product was dissolved into ethyl acetate (150 ml) and extracted with 1N-HCl aqueous solution (3×25 ml). The aqueous layer was alkalined with sodium bicarbonate and extracted with ethyl acetate (2×100 ml). The extracts were dried over magnesium sulfate and filtered off by filtration. The filtrate was concentrated in vacuo to afford (3RS)-3-amino-1-(benzo-thiazol-2-yl)methyl-2,3-dihydro-5-(2-fluorophenyl)-1H-1,4-benzodiazepin-2-one as a colorless crystalline solid (110 mg). The compound was allowed to use in a next reaction step without further purification.

$^1$H-NMR ($CDCl_3$, δ): 2.70 (2H, br), 4.64 (1H, s), 5.53 (2H, dd, J=24 Hz, J=15 Hz), 6.95–7.98 (12H, m)

Preparation 3-1

To a suspension of sodium hydride (0.073 g of a 60% dispersion in mineral oil) in dry N,N-dimethylformamide (15 ml) was added gradually (3RS)-2,3-dihydro-5-(2-fluorophenyl)-3-phthalimido-1 H-1,4-benzodiazepin-2-one (0.665 g) under nitrogen atmosphere at cooling in an ice-bath. The mixture was stirred under the same condition for 15 minutes and at ambient temperature for 2 hours. To the mixture was added dropwise a solution of 4-bromioacetylthiomorpholine (0.41 g) in dry N,N-dimethylformamide (5 ml) with cooling in an ice-bath. After completion of addition, the mixture was allowed to warm to ambient temperature and stirred over night. The reaction mixture was concentrated in vacuo. The residue was treated with acetic acid (3.5 ml) and stirred for 0.5 hour. The mixture was poured into a mixture of ethyl acetate (70 ml) and water (50 ml). The organic layer was separated. The aqueous layer was extracted with ethyl acetate. The organic layers were combined, washed with a saturated sodium bicarbonate aqueous solution and water, dried over sodium sulfate, filtered and concentrated in vacuo to afford a crude (3RS)-2,3-dihydro-5-(2-fluorophenyl)-3-phthalimido-1 -(thicmorpholin-4-yl)carbonylmethyl-1H-1,4-benzodiazepin-2-one (0.82 g) The crude product was used in a next reaction step without further purification.

$^1$H-NMR ($CDCl_3$, δ): 2.50–2.85 (4 H, m), 3.60–3.90 (4H,m) 4.29 (1H, d, J=15Hz), 5.00 (1H, d, J=15 Hz), 6.06 (1H, s), 6.97–7.98 (12H, m)

Preparation 3-2

The following compound was obtained in a similar manner to that of Preparation 2-2.

(3RS)-3-amino-2,3-dihydro-5-(2-fluorophenyl)-1-(thiomorphin-4-yl)carbonylmethyl-1H-1,4-benzodiazepin-2-one $^1$H-NMR ($CDCl_3$,δ): 2.50–2.90 (6H, m), 3.65–3.90 (4H, m), 4.38 (1H, d, J=15 Hz), 4.63 (1H, s), 4.93 (1H, d, J=15 Hz), 7.00–7.80 (8H, m)

Preparation 4-1

To a suspension of sodium hydride (0.32 g of a 60% dispersion in mineral oil) in N,N-dimethylformamide (30 ml) was added gradually (3RS)-2,3-dihydro-5-(2-fluorophenyl)-3-phthalimido-1 H-1,4-benzodiazepin-2-one (2.87 g) under nitrogen atmosphere at cooling in an ice-bath. The mixture was stirred under the same condition for 0.5 hour and at ambient temperature for 1 hour. The mixture was cooled in an ice-bath and a sodium iodide (1.18 g) was added thereto in one portion. To the mixture was added dropwise a solution of 3-chloromethylpyridine (1.00 g) and stirred for 0.5 hour at the same temperature. The mixture was stirred overnight at ambient temperature. To the resultant was added acetic acid (1.5 g) under cooling in an ice-bath. The resultant mixture was poured into water (100 ml) and extracted with ethyl acetate (100 ml). The aqueous layer was adjusted to pH 7.0–8.0 with sodium carbonate and extracted with ethyl acetate (2×50 ml). The combined organic layer was washed with brine and dried over sodium sulfate, filtered and concentrated in vacuo to give a crude compound. The crude compound was purified by flash chromatography on silica gel [eluent ($CHCl_3$:ethyl acetate =1:1)] to afford (3RS)-2,3-dihydro-5-(2-fluorophenyl)-3-phthalimido-1-(pyridin-3-yl)-methyl-1H -1,4-benzodiazepin-2-one as a colorless crystalline solid (0.67 g).

$^1$H-NMR (DMSO-$d_6$, δ): 5.14 (1H, d, J=17 Hz), 5.54 (1H, d, J=17 Hz), 5.87 (1H, s), 7.0–8.5 (16H, m)

Preparation 4-2

The following compound was obtained in a similar manner to that of Preparation 2-2.

(3RS)-3-amino-2,3-dihydro-5-(2-fluorophenyl)-1-(pyridin- 3-yl)methyl-1H-1,4-benzodiazepin-2-one $^1$H-NMR (DMSO-$d_6$,δ): 2.60 -3.00 (2H, br), 4.41 (1H, s), 5.06 (1H, d, J=16 Hz), 5.52 (1H, d, J=16 Hz), 7.00–8.50 (12H, m)

Preparation 5-1

The following compound was obtained in a similar manner to that of Preparation 3-1.

(3RS)-2,3-dihydro-1-(3,5-dimethylisoxazol-4-yl)methyl-5-(2-fluorophenyl)-3-phthalimido-1H-1,4-benzodiazepin-2-one $^1$H-NMR ($CDCl_3$,δ): 2.10 (3H, s), 2.24 (3H, s), 4.53(1H, d, J=16 Hz), 5.52 (1H, d, J=16 Hz), 5.39 (H, s), 7.00–8.00 (12H, m)

Preparation 5-2

A solution of hydrazine monohydrate (0.24 g) in THF (10 ml) was added dropwise to a solution of (3RS)-2,3-dihydro-1-(3,5-dimethylisoxazol-4-yl)methyl-5- (2-fluorophenyl)-3-phthalimido-1H-1,4-benzodiazepin-2-one (1.3 g) in THF (30 ml). After completion of addition, the mixture was stirred at ambient temperature for 2 hours and at refluxed temperature for 3 hours. The mixture was then cooled to ambient temperature. The resultant white precipitates were filtered off. The filtrate was concentrated in vacuo. The residue was treated with ethyl acetate and extracted with 1N-HCl aqueous solution three times. The aqueous layers were combined and alkalined by adding sodium bicarbonate and then extracted with ethyl acetate twice. The organic layers were combined, washed with water, dried over sodium sulfate, filtered and concentrated in vacuo to afford (3RS)-3-amino-2,3-dihydro-1-(3,5-dimethylisoxazol-4-yl)-methyl-5-(2-fluorophenyl)-1H-1,4-benzodiazepin-2-one (0.72 g). The crude product was used in a next reaction step without further purification.

$^1$-NMR ($CDCl_3$, δ): 1.8–2.4 (2H, b), 1.94 (3H, s), 2.20 (3H,s), 4.28 (1H, d, J=16 Hz), 4.44 (1H, s), 5.64 (1H, d, J=16 Hz), 7.00–7.60 (8H, m)

Preparation 6-1

The following compound was prepared in a similar manner to that of Preparation 3-1.

(3RS)-2,3-dihydro-5-(2-fluorophenyl)-3-phthalimido-1-(3-thienyl)methyl-1H-1,4-benzodiazepin-2-one $^1$H-NMR ($CDCl_3$,δ): 5.16 (1H, d, J=16 Hz), 5.24 (1H, d, J=16 Hz), 6.01 (1H, s), 6.95–8.00 (17H, m)

PreDaration 6-2

The following compound was obtained in a similar manner to that of Preparation 5-2.

(3RS)-3-amino-2,3-dihydro-5-(2-fluorophenyl)-1-(3-thienyl)methyl-1H-1,4-benzodiazepin-2-one $^1$H-NMR ($CDCl_3$,δ): 2.00–2.60 (2H, b), 4.58 (1H, s) 5.04 (1H, d, J=16 Hz), 5.48 (1H, d, J=16 Hz), 6.90–7.80 (11H, m)

Preparation 7-1

The following compound was prepared in a similar manner to that of Preparation 3-1.

(3RS)-2,3-dihydro-5-(2-fluorophenyl)-3-phthalimido-1-(quinolin-2-yl)methyl-1H-1,4-benzodiazepin-2-one $^1$H-NMR (DMSO-$d_6$,δ): 5.51 (1H, d, J=19 Hz), 5.54 (1H, d, J=19 Hz), 5.93 (1H, s), 7.2–8.1 (12H, m), 8.31 (1H, s)

Preparation 7-2

The following compound was obtained in a similar manner to that of Preparation 2-2.

(3RS)-3-amino-2,3-dihydro-5-(2-fluorophenyl)-1-(quinolin-2-yl)methyl-1H-1,4-benzodiazepin-2-one (crude 0.73 g)

$^1$H-NMR (DMSO-$d_6$, δ): 4.48 (1H, s), 5.36 (1H, d, J=16 Hz), 5.54 (1H, d, J=16 Hz), 7.0–8.4 (14H, m)

Preparation 8-1

The following compound was prepared in a similar manner to that of Preparation 4-1.

(3RS)-2,3-dihydro-5-(2-fluorophenyl)-1-(2-furyl)methyl-3-phthalimido-1H-1,4-benzodiazepin-2-one $^1$H-NMR ($CDCl_3$, δ): 5.00 (1H, d, J=16 Hz), 5.20 (1H, d, J=16 Hz), 5.97 (1H, s), 6.30 (1H, m), 6.35 (1H, m), 6.97 (13H, m)

Preparation 8-2

The following compound was obtained in a similar manner to that of Preparation 2-2.

(3RS)-3-amino-2,3-dihydro-5-(2-fluorophenyl)-1-(2-furyl)methyl-1H-1,4-benzodiazepin-2-one $^1$H-NMR ($CDCl_3$, δ): 1.70–2.60 (2H, b), 4.55 (1H, s), 5.09 (1H, d, J=16 Hz), 5.16 (1H, d, J=16 Hz), 6.22–6.32 (2H, m), 7.00–7.88 (9H, m)

Preparation 9-1

The following compound was prepared in a similar manner to that of Preparation 4-1.

(3RS)-2,3-dihydro-1-[2-(1,3-dioxolan-2-yl)ethyl]-5-(2-fluorophenyl)-3-phthalimido-1H-1,4-benzodiazepin-2-one $^1$H-NMR ($CDCl_3$,δ): 1.87–1.98 (1H, m), 1.99–2.11 (1H, m), 3.72–3.96 (5H, m), 4.48–4.59 (1H, m), 4.85–4.89 (1H, m), 5.93 (1H, s) 6.98–7.96 (12H, m)

Preparation 9-2

The following compound was obtained in a similar manner to that of Preparation 2-2.

(3RS)-3-amino-2,3-dihydro-1-[2-(1,3-dioxolan-2-yl) ethyl]-5-(2-fluorophenyl)-1H-1,4-benzodiazepin-2-one $^1$H-NMR ($CDCl_3$, δ): 1.77–2.00 (2H, m), 2.05 (2H, s), 3.71–4.00 (5H, m), 4.49 (1H, s), 4.50–4.62 (1H, m), 4.80–4.88 (1H, m), 6.99-7.79 (8H, m)

Preparation 10-1

The following compound was prepared in a similar manner to that of Preparation 4-1.

(3RS)-2,3-dihydro-5-(2-fluorophenyl)-3-phthalimido-1-(pyridin-2-yl)methyl-1H-1,4-benzodiazepin-2-one $^1$H-NMR (DMSO-$d_6$,δ): 5.24 (1H, d, J=15 Hz), 5.42 (1H, d, J=15Hz), 5.85 (1H, s), 7.0–8.6 (16H, m)

Preparation 10-2

The following compound was obtained in a similar manner to that of Preparation 2-2.

(3RS)-3-amino-2,3-dihydro-5-(2-fluorophenyl)-1-(pyridin-2-yl)methyl-1H-1,4-benzodiazepin-2-one Preparation 11-1

The following compound was prepared in a similar manner to that of Preparation 4-1.

(3RS)-2,3-dihydro-5-(2-fluorophenyl)-3-phthalimido-1-(pyridin-4-yl)methyl-1H-1,4-benzodiazepin-2-one The crude product was purified by flash chromatography on silica gel [eluent ($CHCl_3$:ethyl acetate=1:1)] to afford the above compound as a colorless crystal.

Preparation 11-2

The following compound was obtained in a similar manner to that of Preparation 2-2.

(3RS)-3-amino-2,3-dihydro-5-(2-fluorophenyl)-1-(pyridin-4-yl)methyl-1H-1,4-benzodiazepin-2-one The crude product, which was checked by preparative TLC, was pure enough to be used without further purification.

Preparation 12

The following compound was prepared in a similar manner to that of Preparations 2-1 and 7-2.

(3RS)-3-amino-1-(benzoxazol-2-yl)methyl-2,3-dihydro-5-(2-fluorophenyl)-1H-1,4-benzodiazepin-2-one $^1$H-NMR ($CDCl_3$,δ) 2.70 (2H, br), 4.50 (1H, s), 5.42 (1H, d, J=15 Hz), 5.60 (1H, d, J=15 Hz), 7.10–7.85 (m, 12H)

Preparation 13-1

The following compound was obtained in a similar manner to that of Preparation 1-2.

(3RS)-3-amino-2,3-dihydro-5-(2-fluorophenyl)-1H-1,4-benzodiazepin-2-one $^1$H-NMR ($CDCl_3$, δ): 1.8–2.4 (2H, br), 4.52 (1H, s), 6.9–7.8 (8H, m), 9.00 (1H, s)

Preparation 13-2

To a mixture of (3RS)-3-amino-2,3-dihydro-5-(2-fluorophenyl)-1 H-1,4-benzodiazepin-2-one (2.43 g) and triethylamine (1.00 g) in dichloromethane (20 ml) was added dropwise a solution of benzyloxycarbonyl chloride (1.69 g) in dichloromethane (10 ml) under cooling in an ice-bath. The mixture was stirred at ambient temperature overnight.

The resultant mixture was dissolved in a mixture of ethyl acetate (200 ml) and water (100 ml). The organic layer was separated and washed with 1N HCl aqueous solution (100 ml), water (100 ml) and brine (100 ml).

The organic layer was dried over sodium sulfate, filtered and concentrated in vacuo to afford (3RS)-3-benzyloxycarbonylamino-2,3-dihydro-5-(2-fluorophenyl)-1H-1,4-benzodiazepin-2-one (2.71 g).

The product was allowed to use in a next reaction step without further purification.

$^1$H-NMR (DMSO-$d_6$, δ): 5.06 (2H, s) 5.21 (1H, d, J=9 Hz), 7.10–7.80 (13H, m), 8.50 (1H, d, J=9 Hz), 10.97 (1H, s)

Preparation 13-3

To a suspension of sodium hydride (0.294g of a 60 % dispersion in mineral oil (7.36 mmol) in N,N-dimethylformamide (20 ml) was added slowly (3RS)-3-benzyloxycarbonylamino-2,3-dihydro-5-(2-fluorophenyl)-1H-1,4-benzodiazepin-2-one (2.70 g) under cooling in an ice-bath. The mixture was stirred at the same temperature for 0.5 hour and at ambient temperature for 1 hour. To the mixture was added dropwise a solution of methyl bromoacetate (1.13 g) in N,N-dimethylformamido (5 ml) under cooling in an ice-bath. The mixture was stirred at ambient temperature overnight. To the reaction mixture was added acetic acid (1 ml) and stirred for 0.5 hour. The resultant was poured into water (100 ml) and extracted with ethyl acetate. The organic layer was dried over sodium sulfate, filtered and concentrated in vacuo to afford (3RS)-3-benzyloxycarbonylamino-2,3-dihydro-5-(2-fluoro-phenyl)-1-(methoxycarbonylmethyl)-1H-1,4-benzodiazepin-2-one (3.4 g).

The product was allowed to use in a next reaction step without further purification.

$^1$H-NMR (DMSO-$d_6$, δ) 3.61 (3H, s) , 4.70 (1H, d, J=16 Hz) 4.78 (1H, d, J=16 Hz), 5.06 (2H, s), 5.21 (1H, d, J=9 Hz), 7.0–7.8(13H, m), 8.62 (1H, s)

Preparation 13-4

To a solution of (3RS)-3-benzyloxycarbonylamino-2,3-dihydro-5-(2-fluorophenyl)-1-(methoxycarbonylmethyl)-1H-1,4-benzodiazepin-2-one (3.45 g) in 1,4-dioxane (100 ml) was treated with 0.1 N lithium hydroxide aqueous solution (50 ml) at ambient temperature and the mixture was stirred overnight.

The mixture was concentrated in vacuo and to the residue was added IN HCl aqueous solution until the pH of the solution reached below 7.The aqueous layer was extracted with ethyl acetate (2×100 ml) and the organic layer was dried over sodium sulfate, filtered and concentrated in vacuo. The residue was triturated with isopropyl ether. The resultant crystalline solids were collected by suction to afford (3RS)-3-benzyloxycarbonylamino-2,3-dihydro-5-(2-fluorophenyl)-1-(hydroxycarbonylmethyl)-1H-1,4-benzodiazepin-2-one as a colorless solid.

This compound was allowed to use in a next reaction step without further purification.

Preparation 13-5

To a solution of (3RS)-3-benzyloxycarbonylamino-2,3-dihydro-5-(2-fluorophenyl)-1-(hydroxycarbonylmethyl)-1H-1,4-benzodiazepin-2-one (0.50 g) in dry dichloromethane (10 ml) was treated with N,N-bis(2-oxo-3-oxazolidinyl)phosphinic chloride (0.367 g) and triethylamine (0.115 g) under cooling in an ice-bath. The mixture was stirred for 0.5 hour at the same condition. To the mixture was added dropwise a solution of 3-azabicyclo [3.2.2]nonane in dry dichloromethane (5 ml) at the same temperature. The mixture was stirred at ambient temperature overnight.

The reaction mixture was concentrated in vacuo and the residue was dissolved in a mixture of ethyl acetate (50 ml) and water (50 ml). The organic layer was separated and washed with 10% citric acid aqueous solution. The organic solution was dried over sodium sulfate, filtered and concentrated in vacuo to afford a crude compound.

This crude compound was purified by flash chromatography with an eluent of chloroform to afford (3RS)-1-[(3-azabicyclo-[3.2.2] non-3-yl)carbonylmethyl]-3-benzyloxycarbonylamino-2,3-dihydro-5-(2-fluorophenyl)-1H-1,4-benzodiazepin-2-one as a white crystalline solid.

$^1$-NMR (DMSO-$d_6$,δ): 1.40–2.20 (10H, m), 3.40–3.80 (4H, m), 474 (1H, d, J=16 Hz), 494 (1H, d, J=16 Hz), 5.02 (2H, s), 5.20 (1H, d, J=10 Hz), 7.00–7.80 (13H, m), 8.56 (1H, d, J=9 Hz)

Preparation 13-6

To a solution of (3RS)-1-[(3-azabicyclo[3.2.2]non-3-yl) carbonylmethyl]-3-benzyloxycarbonylamino-2,3-dihydro-5-(2-fluorophenyl)-1H-benzodiazepin-2-one (0.24 g) in a mixture of ethanol (10 ml) and acetic acid (6 ml) was treated with Pearlmzan's catalyst (palladium hydroxide on carbon, 70 mg, 20 w/w %).

The mixture was stirred under hydrogen atmosphere at 25° C. overnight. The reaction mixture was filtered and concentrated in vacuo. The residue was dissolved in chloroform (50 ml) and washed with saturated sodium bicarbonate aqueous solution. The organic layer was dried over sodium sulfate, filtered and concentrated in vacuo to afford (3RS)-3-amino-1-[(3-azabicyclo[3.2.2]-non- 3-yl) carbonylmethyl]-2,3-dihydro-5-(2-fluorophenyl)-1H-1,4-benzodiazepin-2-one as a colorless crystalline solid.

The product was allowed to use in a next reaction step without further purification.

$^1$-NMR ($CDCl_3$,δ) 1.40–2.30 (12H, m), 3.20–3.80 (4H, m), 4.38 (1H, d, H=16 Hz), 4.62 (1H, s), 5.07 (1H, d, H=16 Hz), 6.90–8.00 (8H, m)

Preparation 14

The following compound was obtained in a similar manner to that of Preparations 1-1 and 2-2.

(3RS)-3-amino-2,3-dihydro-5-(2-fluorophenyl)-1-(tetrahydrofuran-2-yl)methyl-1H-1,4-benzodiazepin-2-one The crude product, which has one spot by a Preparative TLC, was pure enough to be used in a reaction step without further purification.

Preparation 15

The following compound was obtained in a similar manner to that of Preparations 9-1 and 2-2.

(3RS)-3-amino-1-(benzimidazol-2-yl)methyl-5-(2-fluorophenyl)-1H-1,4-benzodiazepin-2-one $^1$H-NMR (DMSO-$d_6$,δ) 3.36 (2H, br), 4.44 (1H, s), 5.23 (1H, d, J=15 Hz), 5.32 (1H, d, J=15Hz), 7.12–8.00 (12H, m)

Preparation 16-1

To a suspension of (3RS)-3-amino-5-(2-fluorophenyl)-2,3-dihydro-1H-1,4-benzodiazepin-2-one (7.66 g), triethylamine (9.31 g) and a catalytic amount of hydroxylamine hydrochloride in methylene chloride (200 ml) was added dropwise a solution of di-tert-butyl dicarbonate (9.31 g) in methylene chloride (5 ml) under stirring at ambient temperature. The mixture was stirred for 4.5 hours under the same condition. The solvent was removed from the reaction mixture to give a residue, which was dissolved in ethyl acetate and washed with water several times. After drying over magnesium sulfate, the solvent was removed in vacuo to give crystals, which were triturated in diethyl ether, collected by filtration, washed with ether and dried under reduced pressure to afford (3RS)-3-tert-butoxycarobonylamino-5-(2-fluorophenyl)-2,3-dihydro-1H-1,4-benzodiazepin-2-one (10.13 g) as a white crystalline powder.

mp: 205°–206° C.; IR (Nujol): 3330, 3180, 3060, 1700 (sh), 1670, 1605, 1510, 1481, 1450, 1397, 1365, 1330, 1270, 1250, 1220, 1170, 1060, 1010, 958, 891, 819, 772, 756, 677 $cm^{-1}$; $^1$H-NMR ($CDCl_3$, δ): 1.49 (9H, s), 5.33 (1H, d, 8.5Hz), 6.40 (1H, d, J=8.5 Hz), 6.95–7.75 (8H, m), 8.89 (1H, s)

Preparation 16-2

To a solution of (3RS)-3-tert-butoxycarobonylamino-5-(2-fluorophenyl)-2,3-dihydro-1H-1,4-benzodiazepin-2-one (1.107 g) in N,N-dimethylformamide (20 ml) was added portionwise sodium hydride (60 % dispersion in mineral oil, 0.132 g) under stirring at 0°–5° C. in an ice-bath. The mixture was stirred for 0.5 hour under the same condition and for 1 hour at ambient temperature. To the reaction mixture which was cooled again in an ice-bath was added dropwise a solution of 2-acetoxyethyl bromide (0.37 ml) in N,N-dimethylformamide (5 ml) under stirring, which was continued for 23 hours at ambient temperature. The reaction mixture was poured into water (100 ml) and extracted with ethyl acetate twice. The extract was washed with water, dried over magnesium sulfate and evaporated in vacuo to give a crude oil, which was subjected to a column chromatography on silica gel eluting with a mixture of chloroform and methanol (100:1). The fractions containing the desired compound were combined and evaporated in vacuo to give an oil (1.11 g), which was crystallized by trituration with diisopropyl ether and collected by filtration to afford (3RS)-1-(2-acetoxyethyl)-3-tert-butoxycarobonylamino-5-(2-fluorophenyl)-2,3-dihydro-1H-1,4-benzodiazepin-2-one (0.95 g) as a white crystalline powder.

mp: 121°–122.5° C. IR (Nujol): 3300, 1735, 1710 (sh), 1680, 1604, 1483, 1373, 1230, 1161, 1049, 758 $cm^{-1}$; $^1$H-NMR ($CDCl_3$,δ) : 1.47 (9H, s), 1.79 (3H, s), 3.89–4.23 (3H, m), 4.6–4.75 (1H, m), 5.33(1H, d, J=8.7 Hz), 6.46(1H, d, J=8.7 Hz), 6.95–7.82 (8H, m)

Preparation 16-3

To a solution of (3RS)-1-(2-acetoxyethyl)-3-tert-butoxycarbonylamino-5-(2-fluorophenyl)-2,3-dihydro-1H-1,4-benzodiazepin-2-one (0.83 g) in 85 % aqueous ethanol (20 ml) was added potassium carbonate (0.19 g). The mixture was warmed at 65°–70° C. under stirring for 3 hours. Ethanol was removed in vacuo from the reaction mixture and to the aqueous residue was added water (50 ml). The resultant precipitate was collected by filtration, washed with water and dried under reduced pressure to afford (3RS)-1-(2-hydroxylethyl)-3-tert-butoxycarbonylamino-5-(2-fluorophenyl)-2, 3-dihydro-1H-1,4-benzodiazepin-2-one (0.75 g) as a white crystalline powder, which was used in a following reaction step without further purification.

mp: 199.5°–200° C. IR (Nujol): 3430, 3260, 1696, 1662, 1609, 1528, 1445, 1366, 1260, 1164, 1150, 760 $cm^{-1}$; $^1$H-NMR ($CDCl_3$, δ): 1.47 (9H, s), 2.10 (1H, t, J=5.8 Hz), 3.6–4.0 (3H, m), 4.3–4.45 (1H, m), 5.33 (1H, d, J=8.7 Hz), 6.45 (1H, d, J=8.7 Hz), 6.9–7.8 (8H, m); Mass (m/z): 414 ($M^+$+1)

Preparation 16-4

To a suspension of (3RS)-1-(2-hydroxylethyl)-3-tert-butoxycarbonylamino-5-(2-fluorophenyl)-2,3-dihydro-111-1,4-benzodiazepin-2-one (731.9 mg) in methylene chloride (15 ml) was added phosgene (192.9 mg) under stirring at 0° C. To the resultant mixture was added dropwise a solution of pyridine (140.0 mg) in methylene chloride (7 ml) under the same condition. After the addition was completed, the mixture was stirred at ambient temperature for 2 hours.

The reaction mixture was cooled again in an ice-bath and to the cooled solution was added dropwise a solution of 3-azabicyclo[3. 2.2]nonane (222.0 mg) and triethylamine (180 mg) in methylene chloride (5 ml) under stirring. The mixture was stirred at ambient temperature for 5 hours and washed with water twice. The separated organic layer was dried over magnesium sulfate and evaporated in vacuo to afford (3RS)-1-{2-(3-azabicyclo[3.2.2]-non-3-yl) carbonyloxyethyl}-3-tert-butoxycarbonylamino-5-(2-fluorophenyl)-2,3-dihydro-1H-1,4-benzodiazepin-2-one (0.99 g) as an amorphous mass. This was used in a following reaction step without further purification.

IR (Film) : 3420, 1710(sh), 1680, 1604, 1490, 1448, 1390, 1367, 1267, 1215, 1161, 1122, 1067, 1010, 820, 760 (sh), 750, 665 $cm^{-1}$; $^1$H-NMR ($CDCl^3$, δ): 1.47 (9H, s), 1.35–1.6 (4H, m), 1.94 (1H, m), 2.94–4.3 (8H, m), 4.7–4.85 (1H, m), 5.34 (1H, d, J=8.7 Hz), 6.46 (1H, d, J=8.7 Hz), 6.9–7.7 (8H, m)

Preparation 16-5

To a solution of (3RS)-1-{2-(3-azabicyclo[3,2,2]non-3-yl)carbonyloxyethyl}-3-tert-butoxycarbonylamino-5-(2-fluorophenyl)-2,3-dihydro-1H-1,4-benzodiazepin-2-one (1.0 g) in ethyl acetate (22.1 ml) was added dropwise 4N-hydrochloric acid in ethyl acetate (22.1 ml) under stirring and ice-bath cooling. The mixture was stirred for 2 hours under the same condition. The reaction mixture was neutralized with an aqueous solution of sodium bicarbonate under stirring. The separated organic layer was washed with water twice and dried over magnesium sulfate. Removal of the solvent gave an amorphous mass (0.83 g), which was subjected to column chromatography on silica gel eluting with a mixture of chloroform and methanol (100:1). The fractions containing the desired compound were combined and evaporated in vacuo to afford (3RS)-1-{2-(3-azabicyclo [3.2.2]non-3-yl)-carbonyloxyethyl}-3-amino-5-(2-fluorophenyl)-2,3-dihydro-1H-1,4-benzodiazepin-2-one (0.75 g) as an amorphous mass which was used in a following reaction step without further purification.

IR (Film): 3350, 1685, 1675, 1605, 1575, 1484, 1328, 1265, 1215, 1120, 1100, 1004, 760, 745 $cm^{-1}$; NMR ($CDCl_3$,δ): 1.15–2.0 (10H, m), 2.35 (2H, br), 2.99–3.64 (4H, m), 3.89–4.29 (3H, m), 4.53 (1H, s), 4.68–4.79 (1H, m), 7.02–7.69 (8H, m) ; Mass (m/z) 465 ($M^+$+1)

Preparation 17-1

The following compound was obtained in a similar manner to that of Preparation 16-2.

(3RS)-1-(1-adamantyloxycarbonylmethyl)-3-tert-butoxycarbonylamino-5-(2-fluorophenyl)-2,3-dihydro-H-1, 4-benzodiazepin-2-one IR (Film): 3410, 1730 (sh), 1715 (sh), 1685, 1605, 1490, 1450, 1380, 1210, 1160, 1050, 930, 750 $cm^{-1}$; $^1$H-NMR ($CDCl_3$, δ): 1.47 (9H, s), 1.62 (7H, br s), 1.71 (1H, br s), 2.11 (8H, s) , 4.44 (2H, ABq.

J=17.1 Hz, 72.0 Hz), 5.38 (1H, d, 8.4 Hz), 6.47 (1H, d, J=8.4 Hz), 6.95–7.8 (8H, m) Mass (m/z): 562 ($M^+$+1)

Preparation 17-2

The following compound was obtained in a similar manner to that of Preparation 16-5.

(3RS)-1-(1-adamantyloxycarbonylmethyl)-3-amino-5-(2-fluorophenyl)-2,3-dihydro-1H-1,4-benzodiazepin-2-one IR (Film): 3370, 1735, 1690, 1602, 1474, 1449, 1370, 1354, 1240, 1204, 1046, 760 $cm^{-1}$; $^1$H-NMR ($CDCl_3$, δ): 1.65 (8H, br s), 2.13 (8H, br s), 2.35 (2H, br), 4.46 (2H, ABq, J=17.1 Hz, 83.4 Hz), 4.59 (1H, s), 7.03–7.77 (8H, m) Mass (m/z) 462 ($M^+$+1)

Preparation 18-1

To a solution of (3RS)-3-tert-butoxycarbonylamino-5-(2-fluorophenyl)-2,3-dihydro-1H-1,4-benzodiazepin-2-one (5.88 g) in N,N-(1imethylformamide (100 ml) was added portionwise sodium hydride (60% dispersion in mineral oil, 0.76 g) under stirring and cooling at 5° C. The mixture was stirred under the same condition for 0.5 hour and at ambient temperature for 1 hour. To the mixture was added dropwise a solution of ethyl bromoacetate (3.19 g) in N,N-dimethylformamide (10 ml) under cooling in an ice-bath. After the addition was completed, the mixture was stirred at ambient temperature for 3 hours. The reaction mixture was poured into water (300 ml) under vigorous stirring. The resultant precipitates were collected by filtration, washed with water and dried under reduced pressure over phosphorus pentoxide to afford (3RS)-1-ethoxycarbonylmethyl-3-tert-butoxycarbonylamino-5-(2-fluorophenyl)-2,3-dihydro-1H-1,4-benzodiazepin-2-one (7.25 g) as a crystalline powder, which was used in a following reaction step without further purification.

IR (Nujol): 1740, 1710, 1685, 1605, 1485, 1375, 1200, 1162, 1014, 938, 760 $cm^{-1}$; $^1$H-NMR ($CDCl_3$,δ): 1.23 (3H, t, J=7.0 Hz), 1.47 (9H, s) 4.15–4.30 (2H, m), 4.58 (2H, ABq, J=17.3 Hz, 36.0 Hz), 5.41 (1H, d, J=8.5 Hz), 6.44 (1H, d, J=8.5 Hz), 6.9–7.8 (8H, m) Mass (m/z) 456 ($M^+$+1)

Preparation 18-2

To a solution of (3RS)-1-ethoxycarbonylmethyl-3-tert-butoxycarbonylamino-5-(2-fluorophenyl)-2,3-dihydro-1H -1,4-benzo-diazepin-2-one (7.2 g) in methanol (100 ml) was added 4N solution of hydrogen chloride in ethyl acetate (55 ml) under stirring at ambient temperature. The mixture was stirred for 4 hours under the same condition and allowed to stand overnight. The solvent was removed in vacuo to give residue, to which was added water. The mixture was adjusted to pH 8 with an aqueous solution of sodium bicarbonate and extracted with ethyl acetate twice. The combined extract was washed with water and dried over magnesium sulfate. Removal of the solvent afford (3RS)-3-amino-1-ethoxycarbonylmethyl-5-(2-fluorophenyl)-2,3-dihydro-1H-1,4-benzodiazepin-2-one (5.46 g) as an amorphous mass, which was used in a following reaction step without further purification.

IR (Film): 3350, 2960, 1740, 1685, 1600, 1575, 1484, 1449, 1355, 1325, 1205, 1020, 1000, 750 $cm^{-1}$; $^1$H-NMR ($CDCl_3$,δ): 1.24, 1.25 (3H, each t, J=6.6 Hz each), 2.37 (2H, br s), 4.1–4.35 (2H, m), 4.59 (2H, ABq, J=17.2 Hz, 46.3 Hz), 4.59 (1H, s), 6.99–7.77 (8H, m); Mass (m/z): 356 ($M^+$+1)

Preparation 18-3

To a solution of (3RS)-3-amino-1-ethoxycarbonylmethyl-5-(2-fluorophenyl)-2,3-dihydro-1H-1,4-benzodiazepin-2-one (5.45 g) in THF (55 ml) was added 3-methylphenyl isocyanate (2.04 g) under stirring at ambient temperature. The mixture was stirred for 2 hours. To the reaction suspension was added diisopropyl ether (100 ml). After stirring for 0.5 hour, the resulting precipitates were collected by filtration, washed with diisopropyl ether and dried in vacuo to afford N-[(3RS)-1-ethoxycarbonyl-methyl-5-(2-fluorophenyl)-2,3-dihydro-2-oxo-1H-1,4-benzodiazepin-3-yl]-N'-(3-methylphenyl)urea (5.72 g) as a white crystalline powder, which was used in a following reaction step without further purification.

mp: 203°–204.5° C. IR (Nujol): 3300, 1735, 1688, 1641, 1610, 1560, 1483, 1375, 1324, 1208, 764, 745 $cm^{-1}$; $^1$H-NMR (DMSO-$d_6$,δ) 1.13 (3H, t, J=7.1 Hz), 2.24 (3H, s), 4.09 (2H, q, J=7.1 Hz), 4.75 (2H, br s), 5.34 (1H, d, J=8.5 Hz), 6.75 (1H, d, J=6.15 Hz) 7.05–7.75 (12H, m), 8.95 (1H, s); Mass (m/z): 489 ($M^+$+1)

Preparation 18-4

To a suspension of N-[(3RS)-1-ethoxycarbonylmethyl-5-(2-fluorophenyl)- 2,3-dihydro-2-oxo-1H-1,4-benzodiazepin-3-yl ]-N'-(3-methylphenyl)urea (5.71 g) in a mixture of ethanol (57 ml) and THF (43 ml) was added 1N aqueous sodium hydroxide solution (47 ml) under stirring at ambient temperature. The mixture was stirred under the same condition for 1 hour and the organic solvent was removed in vacuo. The residual aqueous solution was acidified with 6N aqueous hydrochloric acid and extracted with ethyl acetate twice. The combined extract was washed with water twice and dried over magnesium sulfate. Removal of the solvent gave an amorphous mass, which was triturated in a mixture of methanol and diisopropyl ether and collected by filtration to afford N-[(3RS)-1-carboxymethyl-5-(2-fluorophenyl)-2,3-dihydro-2-oxo-1H-1,4-benzodiazepin-3-yl]-N'-(3-methylphenyl)urea (5.21 g) as a white crystalline powder, which was used in a following reaction step without further purification.

mp: 167°–169° C. IR (Nujol):3280, 2800–2400, 1688, 1643, 1610, 1562, 1488, 1375, 1330, 1216, 778, 765 $cm^{-1}$; $^1$H-NMR (DMSO-$d_6$,δ): 2.24 (3H, S), 4.65 (2H, ABt, J=17.9 Hz), 5.33 (1H, d, J=8.5 Hz), 6.75 (1H, d, J=6.7 Hz), 7.0–7.75 (12H, m), 8.97 (1H, s), 13.0 (1H, br); Mass (m/z): 459 ($M^+$+1)

Preparation 19

To a solution of N-tert-butoxycarbonyl-L-alanine (3.11 g) in acetonitrile (150 ml) was added dropwise a solution of (3RS)-3-amino-1-{(3-azabicyclo[3.2.2]non-3-yl)

carbonylmethyl}-2,3-di-hydro-5-(2-fluorophenyl)-1H-1,4-benzodiazepin-2-one (7.14 g) in methylene chloride (40 ml) under stirring at ambient temperature. The mixture was stood overnight under cooling at around 4° C. The resultant precipitate was collected by filtration.

The filtrate was concentrated in vacuo and partitioned between chloroform and 0.5N NaOH. The organic layer was dried over sodium sulfate, filtered and evaporated to recover a racemic amine (4.0 g). The amine was taken up in acetonitrile and to the resultant solution was added N-butoxycarbonyl-L-alanine (1.74 g) under stirring. The mixture was stirred for 30 minutes, and then 3,5-dichlorosalicylaldehyde (10 mg) was added. The mixture was stood overnight under cooling at around 4° C. The resultant precipitate was collected by filtration.

The combined precipitate was partitioned between methylene chloride and 0.5N NaOH, and the organic layer was dried over sodium sulfate, filtered and evaporated to afford (3R)-3-amino-1-{(3-azabicyclo[3.2.2]non-3-yl) carbonylmethyl}-2,3-dihydro-5-(2-fluorophenyl)-1H-1,4-benzodiazepin-2-one (5.55 g) as s colorless crystal.

$^1$H-NMR ($CDCl_3$,δ): 1.40–2.30 (12H, m), 3.20–3.80 (4H, m) 4.38 (1H, d, J=16 Hz), 4.62 (1H, s), 5.07 (1H, d, J=16 Hz), 6.90–8.00 (8H, m)

Preparation 20

To a solution of N-tert-butoxycarbonyl-L-tryptophan (0.70 g) in acetonitrile (20 ml) was added dropwise a solution of (3RS)-3-amino-1-{(3-azabicyclo[3.2.2]non-3-yl)carbonylmethyl}-2,3-dihydro-5-(2-fluorophenyl)-1H-1,4-benzodiazepin-2-one (1.00 g) in methylene chloride (5 ml) under stirring at ambient temperature. The mixture was stirred overnight. The precipitate was collected by filtration and the colorless solid was partitioned between methylene chloride and 0.5N NaOH. The organic layer was dried over sodium sulfate, filtered and concentrated in vacuo to afford (3S)-3-amino-1-{(3-azabicyclo[3.2.2]non-3-yl) carbonylmethyl}-2,3-dihydro-5-(2-fluorophenyl)-1H-1,4-benzodiazepin-2-one (0.46 g) as s colorless crystal.

$^1$H-NMR ($CDCl_3$,δ): 1.40–2.30 (12H, m), 3.20–3.80 (4H, m), 4.38 (1H, d, J=16 Hz), 4.62 (1H, s), 5.07 (1H, d, J=16 Hz), 6.90–8.00 (8H, m)

Preparation 21-1

The following compound was obtained in a slimilar manner to that of Preparation 16-1.

3RS)-3-tert-butoxycarobonylamino-5-phenyl-2,3-dihydro-1H-1,4-benzodiazepin-2-one IR (Nujol, $cm^{-1}$): 3340, 3210, 1718, 1698, 1602, 1520, 1460, 1370, 1361, 1322, 1170, 1060, 1025, 788, 775, 736, 700; $^1$H-NMR ($CDCl_3$,δ): 1.49 (9H, s), 5.32 (1H, d, 8.6 Hz), 6.37 (1H, d, J=8.6 Hz), 7.13–7.55 (9H, m); LC/MS (m/z): 352 ($M^{+1}$)

Preparation 21-2

The following compound was obtained in a slimilar manner to that of Preparation 18-1.

(3RS)-1-ethoxycarbonylmethyl-3-tert-butoxycarobonylamino-5-phenyl-2,3-dihydro-1H-1,4-benzodiazepin-2-one IR (Nujol, $cm^{-1}$): 3400, 3300, 1740, 1715, 1685, 1600, 1488, 1455, 1373, 1322, 1245, 1200, 1160, 1070, 1012, 694; NMR ($CDCl_3$,δ): 1.20 (3H, t, J=10.9 Hz), 1.47 (9H, s) 4.05–4.23 (2H, m), 4.60 (2H, ABq, J=17.4 Hz, 22.1 Hz), 5.40 (1H, d, J=8.6 Hz), 6.42 (1H, d, J=8.6 Hz), 7.2–7.9 (9H, m); LC/MS (m/z): 438 ($M^{+1}$)

Preparation 21-3

The following compound was obtained in a slimilar manner to that of Preparation 18-2.

(3RS)-3-amino-1-ethoxycarbonylmethyl-5-phenyl-2,3-dihydro-1H-1,4-benzodiazepin-2-one IR (Nujol, $cm^{-1}$): 3370, 3300(sh), 1740, 1686, 1602, 1568, 1485, 1446, 1370, 1356, 1322, 1213, 1118, 1020, 925, 854, 750, 695, 663; $^1$H-NMR ($CDCl_3$,δ): 1.19 (3H, t, J=7.2 Hz), 2.32 (2H, br s) 4.05–4.3 (2H, m), 4.59 (2H, ABq, J=18.9 Hz, 20.8 Hz), 4.61 (1H, d, J=7.4 Hz), 7.2–7.9 (9H, m); LC/MS (m/z): 338 ($M^{+1}$)

Preparation 21-4

The following compound was obtained in a slimilar manner to that of Preparation 18-3.

N-[(3RS)-1-ethoxycarbonylmethyl-5-phenyl-2,3-dihydro-2-oxo-1H-1,4-benzodiazepin-3-yl]-N'-(3-methylphenyl)urea IR (Nujol, $cm^{-1}$) 3300, 1746, 1680, 1645, 1612, 1560, 1518, 1490, 1455, 1445, 1372, 1320, 1217, 1192, 1015, 940, 773, 691

$^1$-H-NMR (DMSO-$d_6$, δ) 1.06 (3H, t, J=7.7 Hz), 2.24 (3H, s), 4.03 (2H, m), 4.75 (2H, ABq, J=17.5 Hz, 27.2 Hz), 5.34 (1H, d, J=8.5 Hz), 6.75 (1H, d, J=6.8 Hz), 7.05–7.75 (13H, m), 8.95 (1H, s);

LC/MS (m/z): 471 ($M^{+1}$)

Preparation 21-5

The following compound was obtained in a slimilar manner to that of Preparation 18-4.

N-[(3RS)-1-carboxymethyl-5-phenyl-2,3-dihydro-2-oxo-1H-1,4-benzodiazepin-3-yl]-N'-(3-methylphenyl)urea IR (Nujol, $cm^1$): 3300, 2800–2300 (br), 1715, 1685, 1638, 1605, 1557, 1490, 1455, 1448, 1375, 1324, 1200, 775, 691;

$^1$H-NMR (DMSO-$d_6$, δ): 2.24 (3H, s), 4.67 (2H, ABq, J=17.7 Hz, 31.0 Hz), 5.33 (1H, d, J=8.5 Hz), 6.76 (1H, d, J=6.7 Hz), 7.05–7.76 (13H, m), 8.99 (1H, s) 12.99 (1H, br s)

LC/MS (m/z): 443 ($M^{+1}$)

Preparation 22-1

To a solution of 2-adamantanone (2.00 g) in formic acid (10 ml) was added dropwise a suspension of hydroxyamine-O-sulfonic acid (2.26 g) in formic acid (7 ml) under stirring at ambient temperature. The mixture was heated at reflux temperature for 3.5 hours. The reaction mixture was allowed to cool to room temperature, alkalined with 1N sodium hydroxide aqueous solution and extracted with chloroform twice. The combined extracts were washed with water and dried over sodium sulfate. Removal of the solvent gave 2-azatricyclo[$4.3.1.1^{4,8}$]undecan-3-one (2.14 g), which was used in a following reaction step without further purification.

$^1$H NMR ($CDCl_3$, δ): 1.70–2.14 (12H, m), 2.70 (1H, m), 3.32 (1H, m), 6.58 (1H, br)

Preparation 22-2

To a solution of diborane in tetrahydrofuran (1M, 20 ml) was added dropwise a solution of 2-azatricyclo[$4.3.1.1^{4,8}$]-undecan-3-one (1.01 g) in dry tetrahydrofuran (20 ml) under stirring at cooling in an ice-bath. The mixture was stirred under the same condition for 2 hours and then at room temperature overnight. To the reaction mixture was added dropwise IN hydrochloric acid aqueous solution (20 ml). After removal of the solvent under reduced pressure, the residue was washed with ethyl acetate. The aqueous layer was alkalined with IN sodium hydroxide aqueous solution, extracted with ethyl acetate three times and dried over sodium sulfate. Removal of the solvent gave 2-azatricyclo [$4.3.1.1^{4,8}$]undecane (0.48 g), which was used in a following reaction step without further purification.

$^1$H NMR ($CDCl_3$, δ): 1.40–2.00 (13H, m), 2.20 (1H, br), 3.02 (2H, s), 3.35 (1H, s)

Preparation 22-3

To a solution of 2-azatricyclo[$4.3.1.1^{4,8}$]undecane (0.30 g) in dichloromethane (4 ml) and water (0.4 ml) was added dropwise a solution of chloroacetyl chloride (0.26 g) in dichloromethane (2 ml) under stirring at cooling in an ice-bath. The mixture was stirred 2 hours under the same condition and then at ambient temperature overnight. The reaction mixture was washed with IN hydrochloric acid aqueous solution and saturated sodium bicarbonate aqueous solution, and dried over sodium sulfate. Removal of the solvent gave N-chloromethylcarbonyl-2-azatricyclo-[4.3.1.$1^{4,8}$]undecane (0.33 g), which was used in a following reaction step without further purification.

$^1$H NMR ($CDCl_3$, δ): 1.50–2.00 (13H, m), 3.63 (2H, m), 4.10 (2H, s), 4.24 (1H, m)

Preparation 22-4

To a suspension of sodium hydride (0.035 g of a 60% dispersion in mineral oil) in dry N,N-dimethylformamide (5 ml) was added dropwise a solution of (3RS)-3-tert-butoxycarbonylamino-2,3-dihydro-5-(2-fluorophenyl)-1H-1,4-benzodiazepin-2-one (0.293 g) in dry N,N-dimethylformamide (2 ml) under stirring at cooling in an ice-bath. After completion of the addition, the mixture was allowed to stand to room temperature and stirred for 2 hours. To the the mixture was added sodium iodide (0.129 g) and followed dropwise a solution of N-chloromethylcarbonyl-2-azatricyclo-[4.3.1.$1^{4,8}$]undecane (0.215 g) in dry N,N-dimethylformamide (2 ml) under stirring at cooing in an ice-bath for 1 hour and then at room temperature overnight. The reaction mixture was concentrated in vacuo. The residue was treated with ethyl acetate and water. The organic layer was washed with water and dried over sodium sulfate. Removal of the solvent gave (3RS)-1-[(2-azatricyclo[4.3.1.$1^{4,8}$]undec-2-yl)carbonylmethyl]-3-tert-butoxycarbonylamino-2,3-dihydro-5-(2-fluorophenyl)-1H-1,4-benzodiazepin-2-one (0.537 g), which was used in a following reaction step without further purification.

$^1$H NMR ($CDCl_3$, δ) 1.45 (9H, s), 1.50–2.08 (13H, m), 3.48–3.72 (2H, m), 4.14 (1H, m), 4.97 (1H, d, H=18 Hz), 5.03 (1H, d, J=18 Hz), 5.42 (2H, m), 6.55 (1H, d, J=8 Hz), 7.00–7.80 (8H, m)

Preparation 22-5

To a solution of (3RS)-1-[(2-azatricyclo[4.3.1.$1^{4,8}$]-undec-2-yl) carbonylmethyl]-3-tert-butoxycarbonylamino-2,3-di-hydro-5-(2-fluorophenyl)-1H-1,4-benzodiazepin-2-one (0.445 g) in nitromethane was treated with hydrogen chloride under stirring at cooling in an ice-bath. The mixture was concentrated in vacuo. The residue was dissolved with ethyl acetate and extracted with 1N hydrochloric acid aqueous solution three times. The combined aqueous layers were alkalined with sodium bicarbonate, extracted with ethyl acetate twice. The extracts were dried over sodium sulfate. Removal of the solvent gave (3RS)-3-amino-1-[(2-azatricyclo[4.3.1.$1^{4,8}$]undec-2-yl)carbonylmethyl]-2,3-dihydro-5-(2-fluorophenyl)-1H-1,4-benzodiazepin-2-one (0.265 g), which was used in a following reaction step without further purification.

$^1$H NMR ($CDCl_3$, δ): 1.49–2.08 (13H, m), 2.56 (2H1, br), 3.52–3.86 (2H, m), 4.15 (1H, m), 5.04 (1H, d, J=18 Hz), 5.08 (1H, d, J=18 Hz), 5.16 (1H, m), 7.00–7.56 (7H, m), 7.70–7.80 (1H, m)

Preparation 23-1

The following compound was prepared in a similar manner to that of Preparation 22-4.

(3RS)-3-tert-butoxycarbonylamino-2,3-dihydro-1-ethoxycarbonylmethyl-5-(2-fluorophenyl)-1H-1,4-benzodiazepin-2-one $^1$H NMR ($CDCl_3$, δ): 1.26 (3H, t, J=6.0 Hz), 1.48 (9H, s), 4.22 (2H, m), 4.45 (1H, d, J=18 Hz), 4.66 (1H, d, J=18 Hz), 5.43 (1H, d, J=10 Hz), 6.42 (1H, d, J=lOHz), 7.00–7.80 (8H, m)

Preparation 23-2

The following compound was prepared in a similar manner to that of Preparation 22-5.

(3RS)-3-amino-2,3-dihydro-1-ethoxycarbonylmethyl-5-(2-fluorophenyl)-1H-1,4-benzodiazepin-2-one $^1$H NMR ($CDCl_3$, δ)1.26 (3H, t, J=6 Hz), 2.50 (2H, br), 4.24 (2H, m), 4.48 (1H, d, J=18 Hz), 4.60 (1H, s), 4.70 (1H, d, J=18 Hz), 7.04–7.76 (8H, m)

Preparation 23-3

To a solution of (3RS)-3-amino-2,3-dihydro-1-ethoxycarbonylmethyl-5-(2-fluorophenyl)-1H-1,4-benzodiazepin-2-one (1.972 g) in dichloromethane (15 ml) was added dropwise a solution of m-tolyl isocyanate (0.884 g) in dichlromethane (5 ml) under stirring. After completion of the addition, the mixture was stirred for 4 hours at ambient temperature. The resultant white precipitates were collected by suction to give N-[(3RS)-2,3-dihydro-1-ethoxycarbonylmethyl-5-(2-fluorophenyl)-2-oxo-1H-1,4-benzodiazepin-3-yl]-N'-(3-methylphenyl)urea as a colorless crystalline solid (1.533 g). The filtrate was concentrated in vacuo. The residue was treated with chloroform and isopropyl ether to recover the desired compound (0.897 g).

$^1$H NMR ($CDCl_3$, δ): 1.14 (3H, t, J=7.0 Hz), 2.32 (3H, s) 4.20 (2H, q, J=7 Hz), 4.52 (1H, d, J=17 Hz), 4.66 (1H, d, J=17 Hz), 5.67 (1H, d, J=8 Hz), 6.85–7.80 (14H, m)

Preparation 23-4

To a solution of N-[(3RS)-2,3-dihydro-1-ethoxycarbonylmethyl-5-(2-fluorophenyl)-2-oxo-1H-1,4-benzodiazepin-3-yl]-N'-(3-methylphenyl)urea (2.444 g) in tetrahydrofuran (18 ml) and ethanol (24 ml) was added a solution of 1N aqueous sodium hydroxide (20 ml) under stirring. The mixture was stirred for 1 hour. After removal of the organic solvent, the residue was washed with ethyl acetate twice. The aqueous layer was acidified with IN aqueous hydrochloric acid and extracted with ethyl acetate twice. The extracts were washed with water and dried over sodium sulfate. Removal of the solvent gave a crude product. The crude product was washed with methanol to give N-[(3RSl-2,3-dihydro-5-(2-fluorophenyl)-1-hydroxycarbonylmethyl-2-oxo-1H-1,4-benzodiazepin-3-yl]-N'-(3-methylphenyl)urea (1.764 g) as a colorless crystalline solid. The washing was concentrated in vacuo, and the residue was washed with isopropyl ether to recover the desired compound (0.404 g) as an yellow crystalline solid.

$^1$H NMR (DMSO-$d_6$, δ) 2.26 (3H, s), 4.64 (2H, m), 5.33 (1H, d, J=9 Hz), 6.74 (1H, d, J=9 Hz), 7.09–7.72 (13H, m), 8.98 (1H, s)

Preparation 24-1

To a suspension of sodium hydride (0.11 g of a 64% dispersion in mineral oil) in dry N,N-dimethylformamide (10 ml) was added (3RS)-2,3-dihydro-5-(2-fluorophenyl)-3-phthalimido-1H-1,4-benzodiazepin-2-one (1.00 g) under stirring for 2 hours at ambient temperature. To the mixture was added sodium iodide (0.42 g) and followed dropwise a solution of 2-chloromethyl-3-methyl-pyridine (0.389 g) in dry N,N-dimethylformamide (3 ml) at ambient temperature. The mixture was stirred overnight at room temperature. The mixture was concentrated in vacuo, and the residue was taken up with ethyl acetate. The organic layer was washed with saturated sodium carbonate aqueous solution, dried over sodium sulfate, filtered and concentrated in vacuo to give (3RS)-2,3-dihydro-5-(2-fluorophenyl)-1-(3-methylpyridin-2-yl)methyl-3-phtalimido-1H-1,4-benzodiazepin-2-one (1.24 g). The product was used in a following reaction step without further purification.

$^1$H NMR ($CDCl_3$, δ): 2.30 (3H, s), 5.26 (1H, d, H=16 Hz), 5.32 (1H, d, J=16 Hz), 6.18 (1H, s), 6.9–8.40 (15H, m)

Preparation 24-2

A solution of (3RS)-2,3-dihydro-5-(2-fluorophenyl)-1-(3-methylpyridin-2-yl)methyl-3-phtalimido-1H-1,4-benzodiazepin-2-one (1.24 g) in tetrahydrofuran (30 ml) was treated with a solution of hydrazine monohydrate (0.129 g) in tetrahydrofuran (5 ml) under stirring for 3 hours at room temperature and followed at 70° C. for 1 hour. The reaction mixture was allowed to cool to room temperature. The resultant precipitates were filtered off by suction and the filtrate was concentrated in vacuo. The residue was taken up with ethyl acetate and extracted with 1N aqueous hydrochloric acid. The aqueous layer was alkalined with sodium bicarbonate and extracted with chloroform twice. The extracts were dried over sodium sulfate, filtered and concentrated in vacuo to give (3RS)-3-amino-2,3-dihydro-5-(2-fluorophenyl)-1-(3-methylpyridin-2-yl)methyl-1H-1,4-benzodiazepin-2-one (0.87 g), which was used in a following reaction step without further purification.

$^1$H NMR ($CDCl_3$, δ): 2.23 (3H, s), 4.65 (1H, s), 5.18 (1H, d, J=16 Hz), 5.42 (1H, d, J=16 Hz), 6.90–8.40 (11H, m)

Preparation 25-1

The following compound was prepared in a similar manner to that of Preparation 24-1.

(3RS)-1-(benzothiophen-3-yl)methyl-2,3-dihydro-5-(2-fluorophenyl)-3-phtalimido-1H-1,4-benzodiazepin-2-one $^1$H NMR ($CDCl_3$, δ): 5.28 (1H, d, J=16 Hz), 5.66 (1H, d, J=16 Hz), 6.06 (1H, s), 6.90–8.01 (17H, m)

Preparation 25-2

To a solution of (3RS)-1-(benzothiophen-3-yl)methyl-2,3-dihydro-5-(2-fluorophenyl)-3-phtalimido-1H-1,4-benzodiazepin-2-one (0.980 g) in tetrahydrofuran (10 ml) was added dropwise hydrazine monohydrate (0.109 g) under stirring at ambient temperature. The mixture was stirred for 1 hour at the same temperature and refluxed under stirring for 2 hours. The reaction mixture was allowed to stand to ambient temperature. The resultant precipitates were filtered off and washed with tetrahydrofuran. The filtrate and washing were combined and concentrated in vacuo to afford a crude product. The crude product was purified by column chromatography on silica gel with an eluent of chloroform and methanol to afford (3RS)-3-amino-1-(benzothiophen-3-yl)methyl-2,3-dihydro-5-(2-fluorophenyl)-1H-1,4-benzodiazepin-2-one.

$^1$H NMR ($CDCl_3$, δ): 2.55 (2H, br), 4.61 (1H, s), 5.10 (1H, d, J=16 Hz), 5.87 (1H, d, J=16 Hz), 6.86–7.80 (13H, m)

Preparation 26-1

98% sulfuric acid (17.5 ml) was added dropwise to 2-picoline-1-oxide (5.22 g) under stirring at cooling in an ice-bath. To the mixture was added dropwise nitric acid (fuming, 15 ml) under the same condition. After completion of the additieon, the mixture was heated at 80°–90° C. for 2 hours. The reaction mixture was allowed to cool to room temperature, poured into water (100 ml) and alkalined with aN aqueous sodium hydroxide. The resultant mixture was extracted with chloroform four times. The combined extracts were dried over sodium sulfate. Removal of the solvent gave 4-nitro-2-picoline-1-oxide (6.52 g).

$^1$H NMR ($CDCl_3$, δ) 2.58 (3H, s), 8.00 (1H, m), 8.14 (1H, s), 8.32 (1H, m)

Preparation 26-2

To a suspension of 4-nitro-2-picoline-1-oxide (0.952 g) in dry methanol (20 ml) was added dropwise a solution of sodium methox-ide prepared from sodium (0.60 g) and methanol (10 ml) under stirring at cooling in an ice-bath. The mixture was stirred for 3 hours under the same condition. The resultant mixture was concentrated in vacuo. The residue was treated with chloroform and water. The organic layer was washed with water and a brine, and dried over sodium sulfate. Removal of the solvent gave 4-methoxy-2-picoline-1-oxide (0.958 g).

$^1$H NMR ($CDCl_3$, δ): 2.57 (3H, s), 3.86 (3H, s), 6.72 (1H, m), 6.80 (1H, m), 8.17 (1H, m)

Preparation 26-3

To a suspension of 4-methoxy-2-picoline-1-oxide (0.859 g) in benzene, dried over molecular sieves 4A (Trademark, WAKO PURE CHEMICAL INDUSTRIES, LTD.) was added gradually p-toluenesulfonyl chloride (1.301 g) and then stirred at room temperature for 2 hours. The mixture was concentrated in vacuo. The residue was heated at 90° C. for 3.5 hours. The resultant mixture was treated with water and washed with ethyl acetate. The aqueous layer was alkalined with sodium bicarbonate and extracted with chloroform three times. The combined extracts were dried over sodium sulfate. Removal of the solvent gave 2-chloromethyl-4-methoxypyridine (0.275 g).

$^1$H NMR ($CDCl_3$, δ) 3.90 (3H, s), 4.64 (2H, s), 6.72 (1H, m), 6.76 (1H, m), 7.04 (1H, m)

Preparation 26-4

The following compound was prepared in a similar manner to that of Preparation 24-1.

(3RS)-2,3-dihydro-5-(2-fluorophenyl)-1-(4-methoxypyridin-2-yl)methyl-3-phtalimido-1H-1,4-benzodiazepin-2-one $^1$H NMR ($CDCl_3$, δ): 3.79 (3H, s), 5.26 (2H, dd, J=24 Hz, J=16 Hz), 6.08 (1H, s), 6.60–8.34 (15H, m)

Preparation 26-5

The following compound was prepared in a similar manner to that of Preparation 25-2.

(3RS)-3-amino-2,3-dihydro-5-(2-fluorophenyl)-1-(4-methoxy-pyridin-2-yl)methyl-1H-1,4-benzodiazepin-2-one $^1$H NMR ($CDCl_3$, δ) 2.37 (2H, br), 3.64 (3H, s), 4.63 (1H, s), 5.16 (1H, d, J=16 Hz), 5.37 (1H, d, J=16 Hz), 6.64–7.70 (10H, m), 8.30 (1H, m)

Preparation 27-1

Acetyl chloride (4.5 ml) was added dropwise to 4-nitro-2-picoline-i-oxide (1.526 g) under stirring at cooling in an ice-bath. The mixture was stirred under the same condition for 2 hours. The reaction mixture was treated with water and alkalined with sodium bicarbonate. The resultant mixture was extracted with chloroform. The organic layer was washed with saturated aqueous sodium carbonate and a brine, and dried over sodium sulfate. Removal of the solvent gave a crude product. The crude product was purified by column chromatography on silica gel with chloroform, then a mixture of chloroform and methanol (10:1) as eluents to give 4-chloro-2-picoline-1-oxide (1.17 g).

$^1$H NMR ($CDCl_3$, δ): 2.51 (3H, s), 7.13 (1H, m), 7.28 (1H, s), 8.20 (1H, m)

Preparation 27-2

The following compound was prepared in a similar manner to that of Preparation 26-3.

4-chloro-2-chloromethylpyridine $^1$H NMR ($CDCl_3$, δ): 3.69 (3H, s), 4.68 (2H, s), 7.27 (1H, s), 7.52 (1H, s), 8.48 (1H, d, J=4 Hz)

Preparation 27-3

The following compound was prepared in a similar manner to that of Preparation 24-1.

(3RS)-1-(4-chloropyridin-2- yl)methyl-2,3-dihydro-5-(2-fluorophenyl)-3-phthalimido-1H--,1,4-benzodiazepin-2-one $^1$H NMR (DMSO-$d_6$, δ): 5.29 (2H, dd, J=6 Hz, J=24 Hz), 6.07 (1H, s), 7.00–7.92 (14H, m), 8.43 (1H, d, J=5 Hz)

Preparation 27-4

The following compound was prepared in a similar manner to that of Preparation 25-2.

(3RS)-3-amino-1-(4-chloropyridin-2-yl)methyl-2,3-dihydro-5-(2-fluorophenyl)- 1H-1,4-benzodiazepin-2-one $^1$H NMR ($CDCl_3$, δ): 2.36 (2H, br), 4.64 (1H, ), 5.17 (1H, d, J=6 Hz), 5.44 (1H, d, J=16 Hz), 7.04–7.74 (10H, m), 8.37 (1H, d, J=3 Hz)

Preparation 28-1

A suspension of 2-methylbenzofuran (0.708 g) and N-bromosuccinimide (0.963 g) in carbon tetrachloride (10 ml) was heated at reflux temperature for 2.5 hours. To the mixture was added 2,2'-azobis(isobutyronitrile) (0.1 g) and heated at the same temperature for additional 1 hour. The reaction mixture was allowed to cool to room temperature. The resultant precipitates were filtered off by suction. The filtrate was concentrated in vacuo to give 2-bromomethylbenzofuran (1.16 g), which was used in a following reaction step without further purification.

$^1$H NMR ($CDCl_3$, δ): 4.60 (2H, s), 6.74 (1H, s), 7.23 (1H, t, J=7 Hz), 7.33 (1H, t, J=7 Hz), 7.49 (1H, d, J=7 Hz), 7.55 (1H, d, J=7 Hz)

Preparation 28-2

To a suspension of sodium hydride (0.185 g of a 60% dispersion in mineral oil) in dry N,N-dimethylformamide (5 ml) was added (3RS)-2,3-dihydro-5-(2-fluorophenyl)-3-phtalimido-1H-1,4-benzodiazepin-2-one (1.700 g) under stirring at cooling in an ice-bath. The mixture was stirred under the same condition for 1 hour and then at room temperature for 1.5 hours. To the mixture was added dropwise a solution of 2-bromomethylbenzofuran (1.076 g) in N,N-dimethylformamide (5 ml) under cooling in an ice-bath. After completion of the addition, the mixture was allowed to stand to room temperature overnight. The reaction mixture was concentrated in vacuo. The residue was treated with ethyl acetate and water. The organic layer was washed with water and a brine, and dried over magnesium sulfate. Removal of the solvent gave (3RS)-1-(benzofuran-2-yl)methyl-2,3-dihydro-5-(2-fluorophenyl)-3-phthalimido-1H-1,4-benzodiazepin-2-one (1.018 g) which was used in a following reaction step without further purification.

$^1$H NMR ($CDCl_3$, δ): 5.20 (1H, d, J=46 Hz), 5.32 (1H, d, J=16 Hz), 6.04 (1H, s), 6.70 (1H, s), 7.00–7.74 (16H, m)

Preparation 28-3

The following compound was prepared in a similar manner to that of Prepaiation 25-2.

(3RS)-3-amino-1-(benzofuran-2-yl)methyl-2,3-dihydro-5-(2-fluorophenyl) -1H-1,4-benzodiazepin-2-one $^1$H NMR ($CDCl_3$, δ): 1.88 (2H, br), 4.60 (5H, s), 5.22 (1H, d, J=16 Hz) , 5.36 (1H, d, J=16 Hz), 6.67 (1H, s), 6.96–7.58 (12H, m)

Preparation 29-1

The following compound was prepared in a similar manner to that of Preparation 28-1.

2-acetyl-3-bromomethylthiophene $^1$H NMR ($CDCl_3$, δ): 2.60 (3H, s), 4.96 (2H, s), 7.22 (1H, d, J=3.5 Hz), 7.47 (1H, d, J=3.5 Hz)

Preparation 29-2

To a suspension of sodium hydride (0.119 g of a 60% dispersion in mineral oil) in dry N,N-dimethylformamide (8 ml) was added dropwise a solution of (3RS)-3-tert-butoxycarbonylamino-2,3-dihydro-5- (2-fluorophenyl)-1H-1,4-benzodiazepin-2-one (1.005 g) in dry N,N-dimethylformamide (5 ml) under stirring at cooling in an ice-bath. The mixture was stirred at the same temperature for 30 minutes and then at room temperature for 1.5 hours. To the mixture was added a solution of 2-acetyl-3-bromomethylthiophen (0.82 g) in N,N-dimethylformamide (3 ml) under cooling in an ice-bath. The mixture was stirred under the same condition for 30 minutes and then at ambient temperature overnignt. The reaction mixture was concentrated in vacuo. The residue was treated with ethyl acetate and water. The organic layer seas washed with water and a brine, and dried over sodium sulfate. Removal of the solvent at reduced pressure gave a crude product. The crude product was purified by column chromatography on silica gel with chloroform as an eluent to give (3RS)-1-(2-acetylthiophen-3-yl)methyl-3-tert-butoxycarbonylamino-2,3-dihydro-5-(2-fluorophenyl)-1H-1,4-benzodiazepin-2-one (0.80 g).

$^1$H NMR ($CDCl_3$, δ): 1.47 (9H, s), 2.52 (3H, s), 5.42 (1H, d, J=8 Hz), 5.56 (1H, d, J=17 Hz), 5.70 (1H, d, J=17 Hz), 6.49 (1H, d, J=8 Hz), 6.84–7.74 (9H, m)

Preparation 29-3

The following compound was prepared in a similar manner to that of Preparation 22-5.

(3RS)-1-(2-acetylthiophen-3-yl)methyl-3-amino-2,3-dihydro-5-(2-fluorophenyl)-1H-1,4-benzodiazepin-2-one $^1$H NMR ($CDCl_3$, δ) 2.20 (2H, br), 2.52 (3H, s), 4.60 (1H, s), 5.62 (1H, d, J=16 Hz), 5.71 (1H, d, J=16 Hz), 6.84–7.68 (10H, m)

Preparation 30-1

The following compound was prepared in a similar manner to that of Preparation 22-4.

(3RS)-3-tert-butoxycarbonylamino-2,3-dihydro-5-(2-fluorophenyl)-1-(1-oxypyridin-2-yl)methyl-1H-1,4-benzodiazepin-2-one The product was purified by column chromatography on silica gel with a mixture of chloroform and methanol (100:1) as an eluent.

$^1$H NMR ($CDCl_3$, δ): 1.50 (9H, s), 5.49 (3H, s), 6.49 (1H, d, J=8 Hz), 7.02–7.53 (10H, m), 7.78 (1H, t, J=8 Hz), 8.24 (1H, d, J=6 Hz)

Preparation 30-2

The following compound was prepared in a similar manner to that of Preparation 22-5.

(3RS)-3-amino-2,3-dihydro-5-(2-fluorophenyl)-1-(1-oxypyridin-2-yl) methyl-1H-1,4-benzodiazepin-2-one $^1$H NMR ($CDCl_3$, δ): 2.56 (2H, br), 4.67 (1H, s), 5.53 (2H, dd, J=11 Hz, 28 Hz), 5.03–7.78 (11H, m), 8.23 (1H, m)

Preparation 31-1

To a suspension of 2-methylnicotinic acid-1-oxide (0.701 g) and N,N-bis(2-oxo-3-oxazolidinyl)phosphinic chloride (1.243 g) in dichloromethane (30 ml) was added dropwise a solution of triethylamine (0.570 g) in dichloromethane (5 ml) and followed a solution of pyrrolidine (0.407 g) in dichloromethane (5 ml) under stirring at cooling in an ice-bath. After completion of the addition, the mixture was allowed to stand to room temperature overnight. The reaction mixture was washed with water and dried over sodium sulfate. Removal of the solvent gave a crude product. The crude product was purified by column chromatography on silica gel with a mixture of chloroform and methanol (50:1) as an elunet to give 3-(1-pyrrolidinylcarbonyl)-2-methylpyridine-1-oxide (0.530 g).

$^1$H NMR ($CDCl_3$, δ): 1.82–1.96 (4H, m), 2.42 (3H, s), 3.09 (2H, t, J=7 Hz), 3.59 (2H, t, J=7 Hz), 7.05 (1H, d, J=5 Hz), 7.13 (1H, t, J=5 Hz), 8.22 (1H, d, J=5 Hz)

Preparation 31-2

The following compound was prepared in a similar manner to that of Preparation 26-3.

2-chloromethyl-3-(1-pyrrolidinylcarbonyl)-pyridine $^1$H NMR ($CDCl_3$, δ): 1.82–2.00 (4H, m), 3.20 (2H, m), 3.60 (2H, m), 4.75 (2H, s), 7.25 (1H, m), 7.58 (1H, m), 8.56 (1H, m)

Preparation 31-3

The following compound was prepared in a similar manner to that of Preparation 22-4.

(3RS)-3-tert-butoxycarbonylamino-2,3-dihydro-5-(2-fluorophenyl)-1-[3-(1-pyrrolidinylcarbonyl) pyridin-2-yl) methyl-1H-1,4-benzodiazepin-2-one $^1$H NMR ($CDCl_3$, δ): 1.42 (9H, s), 1.84–2.00 (4H, m), 3.20–3.40 (2H, m), 3.63 (2H, t, J=8 Hz), 5.13 (2H, dd, J=8 Hz, J=22 Hz), 5.40 (1H, d, J=8 Hz), 6.34 (1H, d, J=8 Hz), 6.95–7.74 (10H, m), 8.42 (1H, m)

Preparation 31-4

The following compound was prepared in a similar manner to that of Preparation 22-5.

(3RS)-3-amino-2,3-dihydro-5-(2-fluorophenyl)-1-[3-(1-pyrrolidinylcarbonyl)pyridin-2-yl]methyl-1H-1,4-benzodiazepin-2-one $^1$H NMR ($CDCl_3$, δ): 1.84–2.00 (4H, m), 2.62 (2H, br), 3.20–3.46 (2H, m), 3.64 (2H, t, J=8 Hz), 4.46 (1H, s), 5.09 (1H, d, J=16 Hz), 5.20 (1H, d, J=16 Hz), 7.00–7.72 (11H, m), 8.43 (1H, m)

Preparation 32-1

The following compound was prepared in a similar manner to that of Preparation 24-1.

(3RS)-2,3-dihydro-1-(4-methylpyridin-2-yl)methyl-5-phenyl-3-phthalimido-1H-1,4-benzodiazepin-2-one $^1$H NMR (DMSO-$d_6$, δ) 2.14 (3H, s), 5.14 (1H, d, J=16 Hz) 5.42 (1H, d, J=16 Hz), 5.88 (1H, s), 6.8–8.3 (15H, m)

Preparation 32-2

The following compound was prepared in a similar manner to that of Preparation 24-2.

(3RS)-3-amino-2,3-dihydro-1-(4-methylpyridin-2-yl) methyl-5-phenyl-1H-1,4-benzodiazepin-2-one $^1$H NMR ($CDCl_3$, δ): 2.00 (3H, s), 4.62 (1H, s), 5.05 (1H, d, J=16 Hz), 5.49 (1H, d, J=16 Hz), 6.7–8.4 (11H, m)

Preparation 33-1

To a suspension of sodium hydride (0.11 g in a 64% dispersion of mineral oil) in dry N,N-dimethylformamide (20 ml) was added slowly (3RS)-2,3-dihydro-5-phenyl-3-phthalimido-1H-1,4-benzodiazepin-2-one (1.00 g) at ambient temperature, and stirred for 2 hours. To the mixture was added sodium iodide (0.413 g) and followed dropwise a solution of 1-chloromethylisoquinoline (0.695 g) in dry N,N-dimethylformamide (5 ml) at ambient temperature and stirred overnight. The mixture was concentrated in vacuo and the residue was taken up with ethyl acetate. The organic layer was washed with saturated sodium carbonate aqueous solution, and dried over sodium sulfate, filtered and concentrated in vacuo to give a crude product. The crude product was purified by column chromatography with chloroform as an eluent to give (3RS)-2,3-dihydro-1-(isoquinolin-1-yl)methyl-5-phenyl-3-phthalimido-1H-1,4-benzodiazepin-2-one (0.54 g) as a colorless form.

$^1$H NMR ($CDCl_3$, δ): 5.54 (1H, d, J=16 Hz)z 6.10 (1H, s), 6.14 (1H, d, J=16 Hz), 7.00–8.40 (19H, m),

Preparation 33-2

The following compound was prepared in a similar manner to that of Preparation 24-2.

(3RS)-3-amino-2,3-dihydro-1-(isoquinolin-1-yl)methyl-5-phenyl-1H-1,4-benzodiazepin-2-one $^1$H NMR ($CDCl_3$, δ): 4.60 (1H, s), 5.37 (1H, d, J=16 Hz), 6.30 (1H, d, J=16 Hz), 6.9–8.4 (15H, m)

Preparation 34-1

All the reaction was carried out under $N_2$ atmosphere. To a stirred cold (ca. 5° C. ) mixture of boron trichloride in p-xylene (1.0M solution, 137.7 ml) and dry toluene (31 ml) was added dropwise a mixture of aniline (10.7 g) and cyclohexylcarbonitrile (25.0 g) in dry toluene (56 ml) at ca. 5° C. in an ice-water bath. The mixture was stirred for 1 hour under the same condition and to the mixture was added slowly anhydrous aluminum chloride (16.9 g) for 30 minutes. The mixture was stirred for 30 minutes under the same condition and for 30 minutes at room temperature, then finally for 16 hours at reflux temperature. To the mixture was added dropwise 1.7N aqueous hydrochloric acid (116 nil) under stirring at cooling in an ice-bath. The mixture was heated under stirring at reflux temperature for 2.5 hours.

After cooling at room temperature, the resultant mixture was taken up with ethyl acetate and water. The organic layer was separated, and the aqueous layer was extracted with ethyl acetate. The combined organic layers were washed with water and a brine, and dried over magnesium sulfate, then the solvent was evaporated to give 2-cyclohexylcarbonylaniline (22.8 g) as an yellow oil. The product was used in a following reaction step without further purification.

$^1$H NMR ($CDCl_3$, δ): 1.00–2.00 (10H, m), 3.24 (1H, m), 6.00–6.50 (2H, br), 6.62 (2H, m), 7.20 (1H, m), 7.78 (1H, m)

Preparation 34-2

To a stirred solution of 2-cyclohexylcarbonylaniline (22.8 g) in dichloromethane (150 ml) and water (11.3 ml) was added dropwise a solution of bromoacetyl bromide (25.0 g) in dichloromethane (30 ml) under stirring at cooling in an ice-bath. The mixture was stirred for 1 hour under the same condition. The organic layer was separated and concentrated in vacuo to give a crude product. The crude product was purified by flash column chromatography on silica gel with a mixture of n-hexane and ethyl acetate as an eluent to give N-bromomethylcarbonyl-2-cyclohexylcarboinylaniline (27.4 g) as an yellow oil.

$^1$H NMR ($CDCl_3$, δ) 1.00–2.00 (10H, m), 3.40 (1H, m), 4.00 (2H, s), 7.20 (1H, m), 7.58 (1H, m), 7.98 (1H, d, J=3 Hz), 8.70 (1H, d, J=3 Hz), 12.34 (1H, s)

Preparation 34-3

To a stirred 2.63N aqueous sodium hydroxide (40 ml) was added hydroxyamine hydrochloride (8.70 g) and ethanol (40 ml), and the mixture was heated at 40° C. To the heated mixture was added dropwise a solution of N-bromomethylcarbonyl-2-cyclohexylcarbonylaniline (5.25 g) in ethanol (30 ml) at the same temperature, and stirred for 20 hours under the same condition. To the mixture was dropwise conc. HCl (7.3 ml) at the same temperature and stirred for 1 hour. After cooling to the room temperature, the mixture was concentrated in vacuo. The residue was taken up with ethyl acetate and water. The organic layer was separated and dried over sodium sulfate. The organic layer was concentrated to give a crude product. The crude product was purified by column chromatography on silica gel with a mixture of ethyl acetate and chloroform. The desired fractions were combined and concentrated in vacuo to give 5-cyclohexy-2,3-dihydro-1H-1,4-benzodiazepin-2-one-4-oxide.

$^1$H NMR (DMSO-$d_6$, δ): 1.0–2.0 (10H, m), 3.12 (1H, m), 4.10 (1H, d, J=10 Hz), 4.50 (1H, d, J=10 Hz), 7.0–7.7 (4H, m), 4.80 (1H, s)

Preparation 34-4

To a suspension of 5-cyclohexy-2,3-dihydro-1H-1,4-benzodiazepin-2-one-4-oxide (0.70 g) in chloroform (10 ml) was added acetic anhydride (3.7 ml) at ambient temperature and the mixture was heated for 4 hours at 70° C. After cooling, the mixture was concentrated in vacuo. The residue was taken up with chloroform. The organic layer was washed with saturated aqueous sodium carbonate, dried over magnesium sulfate, filtered off and concentrated in vacuo to give a crude product. The crude product was purified by column chromatography on silica gel with chloroform to give (3RS)-3-acetoxy-5-cyclohexyl-2,3-dihydro-1H-1,4-benzodiazepin-2-one.

$^1$H NMR ($CDCl_3$, δ): 1.0–2.2 (10H, m), 2.30 (3H, s), 2.80 (1H, m), 5.81 (1H, s), 7.0–7.7 (4H, m) 8.65 (1H, s)

Preparation 34-5

To a solution of (3RS)-3-acetoxy-5-cyclohexyl-2,3-dihydro-1H-1,4-benzodiazepin-2-one (2.00 g) in N,N-dimethylformamide (15 ml) was added potassium phthalimide (1.85 g) under stirring and heated at 60° C. To the mixture was added sodium iodide (12.64 g) and stirred for 3 hours at 100° C. The hot resultant mixture was poured into ice-water to give a crude product. The precipitated crude product was collected by filtration. Dryness under the reduced pressure at 40° C. gave (3RS)-5-cyclohexyl-2,3-dihydro-3-phthalimido-1H-1,4-benzodiazepin-2-one (1.80 g) as an yellow powder, which was used in a following reaction step without further purification.

$^1$H NMR (DMSO-$d_6$, δ): 1.0–2.0 (10H, m), 2.92 (1H, m), 5.44 (1H, s), 7.1–8.0 (8H, m), 10.78 (1H, br)

Preparation 34-6

To a suspension of sodium hydride (54 mg of a 64% dispersion of mineral oil) in N,N-dimethylformamide (3 ml) was added slowly (3RS)-5-cyclohexyl-2,3-dihydro-3-phthalimido-1H-1,4-benzo-diazepin-2-one (0.50 g) at ambient temperature and the mixture was stirred for 2 hours under the same condition. To the mixture was added sodium iodide (0.213 g) and followed dropwise a solution of 2-chloromethylpyridine (0.213 g) at the same temperature. The mixture was stirred overnight at ambient temperature To the mixture was added acetic acid (0.4 ml) and stirred for 10 minutes. The resultant mixture was concentrated in vacuo and the residue was taken up with ethyl acetate and water. The aqueous layer was alkalined with sodium carbonate and extracted with ethyl acetate. The combined extracts were dried over sodium sulfate, filtered and concentrated in vacuo to give a crude compound. The crude compound was purified by column chromatography on silica gel with a mixture of chloroform and methanol to give (3RS)-5-cyclohexyl-2,3-dihydro-3-phthalimido-1-(pyridin-2-yl)methyl-1H-1,4-benzodiazepin-2-one.

$^1$H NMR ($CDCl_3$, δ): 0.80–2.00 (10H, m), 2.75 (1H, m), 5.12 (1H, d, J=16 Hz), 5.22 (1H, d, J=16 Hz), 5.41 (1H, s), 7.00–8.60 (12H, m)

Preparation 34-7

A stirred solution of (3RS)-5-cyclohexyl-2,3-dihydro-3-phthalimido-1-(pyridin-2-yl)methyl-1H-1,4-benzodiazepin-2-one (0.22 g) in tetrahydrofuran (10 ml) was treated with a solution of hydrazine monohydrate (23 mg) in tetrahydrofuran (1 ml) at ambient temperature, and the mixture was stirred for 2 hours at the same temperature, then heated at reflux temperature for 1 hour. After cooling, the resultant precipitates were filtered off. The filtrate was concentrated in vacuo. The residue was taken up with 1N aqueous hydrohloric acid and washed with isopropyl ether. The aqueous layer was alkalined with sodium carbonate and extracted with chloroform. The extract was dried over sodium sulfate, filtered and concentrated in vacuo to give (3RS)-3-amino-5-cyclohexyl-2,3-dihydro-1-(pyridin-2-yl)methyl-1H-1,4-benzodiazepin-2-one (0.12 g) as an yellow oil which was used in a following reaction step without further purification.

H NMR ($CDCl_3$, δ): 0.80–2.00 (10H, m), 2.70 (1H, m), 4.75 (1H, s), 5.10 (1H, d, J=16 Hz), 5.22 (1H, d, J=16 Hz), 7.00–8.70 (8H, m)

Preparation 35-1

The following compound was prepared in a similar manner to that of Preparation 33-1.

(3RS)-2,3-dihydro-5-(2-fluorophenyl)-1-(4-methylpyridin-2-yl) methyl-3-phthalimido-1H-1,4-benzodiazepin-2-one $^1$H NMR (DMSO-$d_6$, δ): 2.14 (3H, s), 5.14 (1H, d, J=16 Hz), 5.42 (1H, d, J=16 Hz), 5.86 (1H, s), 6.80–8.30 (15H, m)

Preparation 35-2

The following compound was prepared in a similar manner to that of Preparation 24-2.

(3RS)-3-amino-2,3-dihydro-5-(2-fluorophenyl)-1-(4-methyl-pyridin-2-yl) methyl-1H-1,4-benzodiazepin-2-one $^1$H NMR ($CDCl_3$, δ): 1.96 (3H, s), 2.50 (2H, br), 4.62 (1H, s), 5.02 (1H, d, J=16 Hz), 5.56 (1H, d, J=16 Hz), 6.70–8.40 (11H, m)

Preparation 36-1

To a suspension of sodium hydride (0.30 g of a 64% dispersion in mineral oil) in N,N-dimethylformamide (30 ml) was added slowly (3RS)-3-tert-butoxycarbonylamino-2,3-dihydro-5-(2-fluorophenyl)-1H-1,4-benzodiazepin-2-one (2.53 g) at ambient temperature and the mixture was stirred for 1 hour under the same condition. To the mixture was added sodium iodide (1.13 g) and followed dropwise a solution of 2-chloromethyl-3-methoxycarbonylpyridine (1.40 g) in N,N-dimethylformamide (10 ml) under stirring. The mixture was stirred overnight at ambient temperature. The resultant mixture was concentrated in vacuo and the residue was taken up with ethyl acetate and water. The aqueous layer was extracted with ethyl acetate. The combined organic layer was dried over sodium sulfate, filtered and concentrated in vacuo to give a crude compound.

The crude compound was purified by column chromatography on silica gel with a mixture of chloroform and methanol to give (3RS)--3-tert-butoxycarbonylamino-2,3-dihydro-5-(2-fluorophenyl)-1-(3-methoxycarbonylpyridin-2-yl) methyl-1H-1,4-benzodiazepin-2-one (2.76 g) as a colorless form.

$^1$H NMR ($CDCl_3$, δ) 1.48 (9H, s), 3.90 (3H, s), 5.49 (1H, d, J=9 Hz), 5.57 (1H, d, J=16 Hz), 5.70 (1H, d, J=16 Hz), 6.50 (1H, d, J=9 Hz), 6.90–7.60 (8H, m), 7.80 (1H, m), 8.26 (1H, d, J=9 Hz), 8.50 (1H, s)

Preparation 36-2

A solution of (3RS)-3-tert-butoxycarbonylamino-2,3-dihydro-5-(2-fluorophenyl)-1-(3-methoxycarbonylpyridin-2-yl) methyl-1H-1,4-benzodiazepin-2-one (0.80 g) in chloroform (10 ml) was treated with hydrogen chloride at room temperature and the mixture was stirred for 1 hour under the same condition. The mixture was concentrated in vacuo and the residue was taken up with chloroform. The organic layer was washed with a saturated sodium carbonate aqueous solution, dried over sodium sulfate, filtered and concentrated in vacuo to give (3RS)-3-amino-2,3-dihydro-5-(2-fluorophenyl)-1-(3-methoxycarbonylpyridin-2-yl) methyl-1H- 1,4-benzodiazepin-2-one (0.64 g) as a colorless form.

$^1$H NMR ($CDCl_3$, δ): 2.50 (2H, br), 3.90 (3H, s), 4.68 (1H, s), 5.55 (1H, d, J=16 Hz), 5.72 (1H, d, J=16 Hz), 7.0–8.6 11H, m)

Preparation 37-1

A solution of (3RS)-3-tert-butoxycarbonylamino-2,3-dihydro-5-(2-fluorophenyl)-1-(3-methoxycarbonylpyridin-2-yl) methyl-1H-1,4-benzodiazepin-2-one (1.00 g) in 1,4-dioxane (40 ml) was treated with an aqueous solution of potassium hydroxide (1.04 g in 15 ml of water) at ambient temperature and stirred overnight at room temperature.

The resultant mixture was concentrated in vacuo and the residue was taken up with 15 ml of water. The aqueous layer was washed with isopropyl ethyl and acidified with 10% citric acid aqueous solution. The resultant precipitate was extracted with chloroform and the organic layer was dried over sodium sulfate.

Filtration and concentration in vacuo gave (3RS)-3-tert-butoxycarbonylamino-2,3-dihydro-5-(2-fluorophenyl)-1-(3- hydroxycarbonylpyridin-2-yl) methyl-1H-1,4-benzodiazepin-2-one (0.71 g) as a brown oil.

$^1$H NMR (DMSO-$d_6$, δ): 1.40 (9H, s), 480–4.99 (2H, m), 5.23 (1H, d, J=8 Hz), 7.18–7.63 (11H, m), 7.78 (1H, d, J=8 Hz)

Preparation 37-2

A solution of (3RS)-3-tert-butoxycarbonylamino-2,3-dihydro-5-(2-fluorophenyl)-1-(3-hydroxycarbonylpyridin-2-yl) methyl-1H-1,4-benzodiazepin-2-one (0.71 g) in tetrahydrofuran (20 ml) was treated with dicyclohexylcalbodiimide (0.29 g) and 1-hydroxybenzotriazole monohydrate (0.215 g) at room temperature. The mixture was stirred for 2 hours at the same condition. To the mixture was added dropwise a solution of ammonium hydroxide (28% ammonia in water, 0.359 g) in tetrahydrofuran (1 ml) at ambient temperature under stirring. The mixture was stirred overnight at ambient temperature. The resultant mixture was concentrated in vacuo, and the residue was taken up with ethyl acetate. The organic layer was washed with a brine and dried over sodium sulfate. Filtration and evaporation gave a crude product. The crude product was purified by column chromatography on silica gel with a mixture of chloroform and methanol to afford (3RS)-1-(3-aminocarbonylpyridin-2-yl)methyl-3-tert-butoxycarbonyl-amino-2,3-dihydro-5-(2-fluorophenyl)-1H,-1,4-benzodiazepin-2-one (0.32 g) as a yellow form.

$^1$H NMR ($CDCl_3$, δ) 1.44 (9H, s), 5.17 (1H, d, J=16 Hz), 5.34 (1H, d, J=16 Hz), 5.42 (1H, d, J=9 Hz), 6.28 (1H, d, J=9 Hz), 7.0–8.6 (13H, m)

Preparation 37-3

The following compound was prepared in a similar manner to that of Preparation 36-2.

(3RS)-3-amino-1-(3-aminocarbonylpyridin-2-yl) methyl-2,3-dihydro-5-(2-fluorophenyl)-1H-1,4-benzodiazepin-2-one $^1$H NMR ($CDCl_3$, δ): 2.50 (2H, br), 4.60 (1H, s), 5.14 (1H, d, J=16 Hz), 5.36 (1H, d, J=16 Hz), 5.90 (1H, br, s), 7.0–8.6 (12H, m)

Preparation 38-1

The following compound was prepared in a similar manner to that of Preparation 37-2.

(3RS)-3-tert-butoxycabonylamino-2,3-dihydro-1-(3-dimethylaminoethylaminocarbonylpyridin-2-yl) methyl-5-(2-fluorophenyl)-1H-1,4-benzodiazepin-2-one $^1$H NMR ($CDCl_3$, δ): 1.43 (9H, s), 2.20 (6H, s), 2.52 (2H, m), 3.44 (1H, br, m), 3.62 (1H, br, m), 3.84 (1H, br, m), 5.12 (1H, d, J=16 Hz), 5.41 (1H, d, J=9 Hz), 5.58 (1H, d, J=16 Hz), 6.39 (1H, d, J=9 Hz), 7.0–8.1 (10H, m), 8.50 (1H, s)

Preparation 38-2

The following compound was prepared in a similar manner to that of Preparation 36-2.

(3RS)-3-amino-2,3-dihydro-1-(3-dimethylaminoethylaminocarbonylpyridin-2-yl)methyl-5-(2-fluorophenyl)-1H-1,4-benozodiazepin-2-one $^1$H NMR ($CDCl_3$, δ): 2.20 (6H, s), 2.52 (2H, br), 3.44 (2H, m), 3.64 (2H, m), 4.60 (1H, s), 5.06 (1H, d, J=16 Hz), 5.60 (1H, d, J=16 Hz), 7.0–8.2 (11H, m), 8.51 (1H, s)

Preparation 39-1

To a stirred solution of 4-tert-butylpyridine (19.0 g) in acetic acid (90 ml) was added dropwise 50% of hydrogen peroxide aqueous solution (20 ml) at room temperature and stirred for 30 minutes under the same condition. The mixture was stirred for 3 hours at ca.80° C. After cooling to room temperature, to the mixture was added dropwise another 20 ml of 50% hydrogen peroxide aqueous solution and stirred for 30 minutes. The mixture was stirred for 3 hours at ca. 80° C. After cooling to room temperature, the mixture was concentrated in vacuo. The residue was taken up with chloroform, and washed with water (50 ml), saturated sodium carbonate aqueous solution (50 ml) and water (50 ml). The organic layer was dried over sodium sulfate, filtered and concentrated in vacuo to give 4-tert-butyl-1-oxypyridine, which was crystallized by isopropyl ether as a colorless powder (19.1 g).

$^1$H NMR ($CDCl_3$, δ): 1.34 (9H, s), 7.27 (2H, d, J=8 Hz), 8.16 (2H, d, J=8 Hz)

Preparation 39-2

To stirred dimethyl sulfate (6.70 g) was added slowly 4-tert-butyl-1-oxypyridine (8.0 g) at ca. 10° C. in an ice-water bath and the mixture was stirred for 3 hours at 80° C. After cooling to room temperature, to the mixture was added a mixture of ethanol and water (1:1, 60 ml) under stirring. To the mixture was added dropwise an aqueous solution of potassium cyanate (6.9 g in 20 ml of water) below 10° C. and stirring for 1 hour under the same condition, and then overnight at room temperature. To the resultant mixture was added 150 ml of water and the resultant mixture was extracted with $CHCl_3$. The organic layer was dried over sodium sulfate, filtered and concentrated in vacuo. A crude compound was purified by column chromatography on silica gel with a mixture of ethyl acetate and n-hexane to give 4-tert-butyl-2-cyanopyridine (4.6 g) as a yellow oil.

$^1$H NMR ($CDCl_3$, δ) 1.28 (9H, s), 7.43 (1H, m), 7.62 (1H, s), 8.53 (1H, d, J=5 Hz)

Preparation 39-3

A solution of 4-tert-butyl-2-cyanopyridine (2.0 g) in ethanol (30 ml) was saturated with HCl gas at room temperature and the mixture was heated for 5 hours at reflux temperature. The resultant mixture was filtered to remove ammonium chloride. The filtrate was concentrated in vacuo. The residue was taken up with water and the aqueous solution was alkalized with sodium carbonate. The resultant organic layer was extracted with isopropyl ether, dried over magnesium sulfate, filtered and concentrated in vacuo to give 4-tert-butylpicolinic acid ethyl ester (2.2 g) as a yellow oil.

$^1$H NMR ($CDCl_3$, δ): 1.31 (9H, s), 1.40 (3H, t), 4.40 (2H, q), 7.40 (1H, m), 8.09 (1H, s), 8.60 (111, d, J=5Hz)

Preparation 39-4

To a suspension of lithium aluminium hydride (0.366 g) in dry tetrahydrofuran (10 ml) was added dropwise a solution of 4-tert-butylpicolinic acid ethyl ester (1.0 g) in dry tetrahydro furan (10 ml) at room temperature. The mixture was stirred for 1.5 hours at the same temperature and then for 1 hour at reflux temperature. After cooling to room temperature, to the mixture was added carefully water to decompose the excess hydride. The mixture was filtered and the filtrate was concentrated in vacuo. The residue was taken up with methanol, dried over magnesium sulfate, filtered and concentrated in vacuo. A crude compound was purified by column chromatography on silica gel with a mixture of chloroform and methanol to give 4-tert-butyl-2-hydproxymethyl-pyridine (0.36 g) as a yellow oil.

$^1$H NMR ($CDCl_3$, δ): 1.32 (9H, s), 4.74 (2H, s), 7.2 (1H, d, J=5 Hz), 7.22 (1H, s), 8.44 (1H, d, J=5 Hz)

Preparation 39-5

To a solution of 4-tert-butyl-2-hydroxymethylpyridine (0.36 g) in chloroform (10 ml) was added dropwise a solution of thionyl chloride (1 ml) in chloroform (5 ml) at room temperature and the mixture was stirred for 3 hours at ca. 50° C., After cooling to room temperature, the resultant mixture was concentrated in vacuo. The residue was taken up with chloroform and washed with saturated sodium carbonate aqueous solution, dried over magnesium sulfate, filtered and concentrated in vacuo to give 4-tert-butyl-2-chloromethylpyridine (0.37 g) as a brown oil.

$^1$H NMR ($CDCl_3$, δ): 1.32 (9H, s), 4.68 (2H, s), 7.24 (1H, d, J=5 Hz), 7.41 (1H, s), 8.48 (1H, d, J=5 Hz)

Preparation 39-6

The following compound was prepared in a similar manner to that of Preparation 33-1.

(3RS)-1-(4-tert-butylpyridin-2-yl)methyl-2,3-dihydro-5-(2-fluorophenyl)-3-phthalimido-1H-1,4-benzodiazepin-2-one $^1$H NMR (DMSO-$d_6$,δ): 1.16 (9H, s), 5.20 (1H, d, J=16 Hz), 5.39 (1H, d, J=16 Hz), 5.87 (1H, s), 7.1–8.4 (15H, m)

Preparation 39-7

The following compound was prepared in a similar manner to that of Preparation 24-2.

(3RS)-3-amino-1-(4-tert-butylpyridin-2-yl)methyl-2,3-dihydro-5-(2-fluorophenyl)-111-1,4-benzodiazepin-2-one $^1$H NMR ($CDCl_3$, δ): 1.17 (9H, s), 2.50 (2H, br), 5.00 (1H, s), 5.19 (1H, d, J=16 Hz), 5.39 (1H, d, J=16 Hz), 6.9–8.5 (11H, m)

Preparation 40-1

The following compound was prepared in a similar manner to that of Preparation 39-1.

1-methyl-2-oxyisoquinoline $^1$H NMR ($CDCl_3$, δ): 2.90 (3H, s), 7.4–8.3 (6H, m)

Preparation 40-2

To a solution of 1-methyl-2-oxyisoquinoline (0.55 g) in chloroform (30 ml) was added dropwise phosphoryl chloride (2.8 ml) at 5° C. in an ice-water bath and the mixture was heated for 14 hours at reflux temperature. The resultant mixture was poured into 50 ml of ice-water. The aqueous layer was alkalized with sodium carbonate and extracted with chloroform. The combined organic layer was dried over magnesium sulfate, filtered and concentrated in vacuo to give 1-chloromethylisoquinoline (0.46 g, 57% purity) as a brown oil.

$^1$H NMR ($CDCl_3$, δ): 5.15 (2H, s), 7.6–8.6 (6H, m)

Preparation 40-3

The following compound was prepared in a similar manner to that of Preparation 33-1.

(3RS)-2,3-dihydro-5-(2-fluorophenyl)-1-(isoquinolin-1-yl)methyl-3-phthalimido-1H-1,4-benzodiazepin-2-one $^1$H NMR (DMSO-$d_6$, δ): 5.80 (1H, d, J=16 Hz), 5.92 (1H, d, J=16 Hz), 5.92 (1H, s), 7.1–8.4 (18H, m)

Preparation 40-4

The following compound was prepared in a similar manner to that of Preparation 24-2.

(3RS)-3-amino-2,3-dihydro-5-(2-fluorophenyl)-1-(isoquinolin-1-yl)methyl-1H-1,4-benzodiazepin-2-one $^1$H NMR ($CDCl_3$, δ): 2.50 (2H, br), 5.53 (1H, d, J=16 Hz), 5.53 (1H, s), 6.20 (1H, d, J=16 Hz), 6.8–8.5 (14H, m)

Preparation 41-1

A solution of 1-methylisoquinoline (1.0 g) in methanol (30 ml) was saturated with gaseous hydrogen chloride at room temperature. The mixture was treated with platinum (IV) oxide (0.2 g). The mixture was vigorous stirred under hydrogen atmosphere at room temperature until hydrogen absorption was stopped. The reaction mixture was filtered off to remove the catalyst. The filtrate was concentrated in vacuo and the residue was taken up with water. The mixture was alkalized with sodium carbonate and the resultant precipitate was extracted with isopropyl ether. The extracts were dried over sodium sulfate, filtered and concentrated in vacuo to give 1-methyl-5,6,7,8-tetrahydroisoquinoline (1.03 g) as a brown oil. $^1$H NMR ($CDCl_3$, δ): 1.6–2.0 (4H, m), 2.42 (3H, s), 2.5–2.9 (4H, m), 6.82 (1H, m), 8.16 (1H, m)

Preparation 41-2

The following compound was prepared in a similar manner to that of Preparation 39-1.

1-methyl-2-oxy-5,6,7,8-tetrahydroisoquinoline $^1$H NMR ($CDCl_3$, δ): 1.6–2.0 (4H, m), 2.48 (3H, s), 2.5–2.8 (4H, m), 6.82 (1H, m), 8.06 (1H, m)

Preparation 41-3

A mixture of 1-methyl-$^2$-oxy-5,6,7,8-tetrahydroisoquinoline (1.1 g) in acetic anhydride (5 ml) was heated for 17 hours at 100° C., To the reaction mixture was added another acetic anhydride (5 ml) and stirred for 3 hours at the same temperature. After cooling to room temperature, the mixture was concentrated in vacuo. The residue was taken up with a mixture of isopropyl ether and 1N hydrochloric acid aqueous solution. The aqueous layer was separated, alkalized with sodium carbonate and extracted with chloroform. The extracts were dried over sodium sulfate, filtered and concentrated in vacuo. A crude compound was purified by column chromatography on silica gel with chloroform to give 1-acetoxymethyl-5,6,7,8-tetrahydroisoquinoline (0.44 g) as a brown oil.

$^1$H NMR ($CDCl_3$, δ): 1.6–2.0 (4H, m), 2.16 (3H, s), 2.6–2.9 (4H, m), 5.20 (2H, s), 6.97 (lH, d, J=5 Hz), 8.28 (1H, d, J=5 Hz)

Preparation 41-4

A solution of 1-acetoxymethyl-5,6,7,8-tetrahydroisoquinoline (0.44 g) in 6N hydrochloric acid (10 ml) aqueous solution was heated for 4 hours at ca. 100° C. After cooling, the mixture was concentrated in vacuo to give 1-hydroxymethyl-5,6,7,8-tetrahydroisoquinoline hydrochloride (0.42 g) as a brown solid.

$^1$H NMR (DMSO-$d_6$, δ): 1.6–1.9 (5H, m), 2.70 (3H, m), 2.98 (2H, m), 4.85 (2H, s), 7.76 (1H, d, J=5 Hz), 8.44 (1H, d, J=5 Hz)

Preparation 41-5

To a solution of 1-hydroxymethyl-5,6,7,8-tetrahydroisoquinoline hydrochloride (0.42 g) in chloroform (10 ml) was added dropwise a solution of thionyl chloride (1.1 ml) in chloroform (5 ml) at room temperature and heated for 2 hours at ca. 50° C. The reaction mixture was concentrated in vacuo and the residue was taken up with ethyl acetate. The organic layer was washed with saturated sodium carbonate aqueous solution, dried over sodium sulfate, filtered and concentrated in vacuo to give 1-chloromethyl-5,6,7,8-tetrahydroisoquinoline (0.22 g) as a brown oil.

$^1$H NMR ($CDCl_3$, δ): 1.7–2.0 (4H, m), 2.7–3.0 (4H, m), 4.68 (2H, s), 7.00 (lH, d, J=5 Hz), 8.26 (1H, d, J=5 Hz)

Preparation 41-6

The following compound was prepared in a similar manner to that of Preparation 33-1.

(3RS)-2,3-dihydro-5-(2-fluorophenyl)-3-phthalimido-1-(5,6,7,8-tetrahydroisoquinolin-1-yl)methyl-1H-1,4-benzodiazepin-2-one $^1$H NMR ($CDCl_3$, δ): 0.8–2.8(8H, m), 5.24(2H, m), 6.08(1H, s), 6.8–8.2(14H, m)

Preparation 41-7

The following compound was prepared in a similar manner to that of Preparation 24-2.

(3RS)-3-amino-2,3-dihydro-5-(2-fluorophenyl)- 1-(5,6,7,8-tetrahydroisoquinolin-1-yl)methyl-1H-1,4-benzodiazepin-2-one $^1$H NMR ($CDCl_3$, δ): 1.6–2.8 (10H, m), 4.90 (1H, s), 5.13 (1H, d, J=16 Hz), 5.37 (lH,d,J=16 Hz), 6.8–8.2 (10H, m)

Preparation 42-1

A solution of isoxazole (3.0 g) in dry methanol (30 ml) was treated with 5% palladium carbon (0.6 g) and the mixture was stirred under hydrogen atmosphere at room temperature until hydrogen absorption was stopped. The resultant mixture was filtered to remove the catalyst. The filtrate was concentrated in vacuo to give 3-aminoacrolein (2.96 g) as a brown solid.

$^1$H NMR (DMSO-$d_6$, δ): 5.10 (1H, q), 6.9–7.6 (3H, m), 8.88 (lH, d, J=9 Hz)

Preparation 42-2

To a mixture of 3-amino acrolein (4.52 g) and acetylacetone (7.64 g) was added catalytic amount of ammonium acetate. The mixture was heated for 19 hours at ca. 110° C., After cooling to room temperature, the mixture was poured into 100 ml of isopropyl ether and dried over magnesium sulfate. The resultant mixture was filtered off by suction in vacuo to remove an insoluble material and the filtrate was concentrated in vacuo. The crude compound was purified by column chromatography on silica gel with chloroform to give 3-acetyl-2-methylpyridine (3.58 g) as a yellow oil.

$^1$H NMR ($CDCl_3$, δ): 2.6 (3H, s), 2.76 (3H, s), 7.24 (1H, m), 7.97 (1H, m), 8.60 (1H, m)

Preparation 42-3

The following compound was prepared in a similar manner to that of Preparation 39--1.

3-acetyl-2-methyl-1-oxypyridine $^1$H NMR ($CDCl_3$, δ): 2.64 (3H, s), 2.68 (3H, s), 7.24 (1H, t), 7.47 (1H, d, J=7 Hz), 8.40 (1H, d, J=7 Hz)

Preparation 42-4

The following compound was prepared in a similar manner to that of Preparation 41-3.

2-acetoxymethyl-3-acetylpyridine $^1$H NMR ($CDCl_3$, δ): 2.18 (3H, s), 2.62 (3H, s), 5.48 (2H, s), 7.36 (1H, t, J=7.0 Hz), 8.06 (111, d, J=7 Hz), 8.71(1H, d, J=7 Hz)

Preparation 42-5

A mixture of 2-acetoxymethyl-3-acetylpyridine (1.03 g) and 6N aqueous hydrochloric acid (30 ml) was heated for 3 hours at ca. 100° C. After cooling to room temperature, the mixture was concentrated in vacuo. The residue was taken up with saturated sodium carbonate aqueous solution and extracted with chloroform. The extract was dried over sodium sulfate, filtered and concentrated in vacuo to give 3-acetyl-2-hydroxymethylpyridine (0.81 g) as a brown oil.

$^1$H NMR ($CDCl_3$, δ): 2.43 (3H, s), 5.00 (2H, s) 7.40 (1H, t), 8.18 (1H, d, J=9 Hz), 8.72 (1H, d, J=7 Hz)

Preparation 42-6

A mixture of 3-acetyl-2-hydroxymethylpyridine(0.2 g) in dichloromethane(10 ml) was treated with catalytic amount of N,N-dimethylformamide. To the mixture was added dropwise a solution of thionyl chloride (1 ml) in dichloromethane (2 ml) at ca. 5° C. in an ice-water bath. The mixture was stirred for 1 hour under the same condition, and then at room temperature for 40 minutes. To the mixture was added carefully dropwise saturated sodium carbonate aqueous solution under stirring in an ice-water bath. The mixture was taken up with chloroform and washed with water. The organic layer was dried over sodium sulfate, filtered and concentrated in vacuo to give 3-acetyl-2-chloromethylpyridine (0.11 g) as a black oil.

$^1$H NMR ($CDCl_3$, δ): 2.64 (3H, s), 5.00 (2H, s), 7.4 (1H, t), 8.02 (1H, d, J=7 Hz), 8.70 (1H, d, J=5 Hz)

Preparation 42-7

The following compound was prepared in a similar manner to that of Preparation 36-1.

(3RS)-3-tert-butoxycarbonylamino-2,3-dihydro-5-(2-fluorophenyl)-1-(3-methylcarbonylpyridin-2-yl) methyl-1H-1,4-benzodiazepin-2-one $^1$H NMR ($CDCl_3$, δ): 1.52 (9H, s), 2.64 (3H, s), 5.49 (1H, d, J=16 Hz), 5.51 (1H, d, J=9 Hz), 5.60 (1H, d, J=16 Hz), 6.47 (1H, d, J=9 Hz), 7.0–7.8 (8H, m), 8.08 (1H, d, J=9 Hz), 8.46 (1H, d, J=7 Hz), 8.88 (1H, s)

Preparation 42-8

The following compound was prepared in a similar manner to that of Preparation 36-2.

(3RS)-3-amino-2,3-dihydro-5-(2-fluorophenyl)-1-(3-methyl-carbonylpyridin-2-yl)methyl-1H-1,4-benzodiazepin-2-one $^1$H NMR ($CDCl_3$, δ): 2.50 (2H, br), 2.64 (3H, s), 4.65 (1H, s), 5.41 (1H, d, J=16 Hz), 5.56 (1H, d, J=16 Hz), 7.0–7.8 (8H, m), 8.04 (1H, d, J=9 Hz), 8.45 (1H, d, J=7 Hz), 8.60 (1H, s)

Preparation 43-1

The following compound was prepared in a similar manner to that of Preparation 29-2.

(3RS,)-3-tert-butoxycarbonylamino-2,3-dihydro-5-(2-fluorophenyl)-1-(2-phthalimido-2-yl)ethyl-1H-1,4-benzodiazepin-2-one The crude product was purified by flash chromatography on silica gel with chloroform to afford the product as a colorless crystal.

$^1$H NMR ($CDCl_3$, δ): 1.46 (9H, s), 3.84 (1H, m), 4.00–4.15(2H, m), 4.45 (1H, m), 5.32 (1H, d, J=8 Hz), 6.47 (1H, d, J=8 Hz), 6.81 (1H, t, J=10 Hz), 7.18–7.90 (11H, m)

Preparation 43-2

To a solution of (3RS)-3-tert-butoxycarbonylamino-2,3-dihydro-5-(2-fluorophenyl)-1-(2-phthalimido-2-yl)ethyl-1H-1,4-benzodiazepin-2-one (0.486 g) in tetrahydrofuran (5 ml) was added a solution of hydrazine monohydrate (0.121 g) in tetrahydrofuran (2 ml) under stirring. The mixture was stirred at ambient temperature for 1 hour, and then at reflux temperature for 2 hours.

The mixture was concentrated in vacuo. The residue was treated with chloroform and the resultant precipitate was filtered off. The filtrate was extracted with 10% citric acid aqueous solution three times. The extracts were combined, alkalized with sodium carbonate, extracted with chloroform twice and dried over sodium sulfate. Filtration and evaporation gave (3RS)-1-(2-aminoethyl)-3-tert-butoxycarbonylamino-2,3-dihydro-5-(2-fluorophenyl)-1H-1,4-benzodiazepin-2-one (Q.17 g).

$^1$H NMR ($CDCl_3$, δ): 1.20–1.60 (2H, br), 1.47 (9H, s), 2.75–2.86 (1H, m), 3.72–3.77 (1H, m), 4.47–4.52 (1H, m), 5.32 (1H, d, J=9 Hz), 6.48 (1H, d, J=8 Hz), 7.02 (1H, t, J=10 Hz), 7.18–7.80 (11H, m)

Preparation 43-3

A suspension of nicotinic acid (0.056 g), dicyclohexylcarbodiimide (0.102 g) and 1-hydroxy-1H-benzotriazole monohydrate (0.080 g) in chloroform (10 ml) was stirred at ambient temperature for 2 hours. To the mixture was added dropwise a solution of (3RS)-1-(2-aminoethyl)-3-tert-butoxycarbonylamino-2,3-dihydro-5-(2-fluorophenyl)-1H-1,4-benzodiazepin-2-one (0.166 g) in chloroform (10 ml). The mixture was stirred overnight.

The mixture was concentrated in vacuo. The residue was purified by column chromatography on silica gel to give (3RS)-3-tert-1)utoxycarbonylamino-2,3-dihydro-5-(2-fluorophenyl)-1-{2-(pyridin-3-yl ) carbonylaminoethyl}-1H-1,4-benzodiazepin-2-one (0.18 g).

$^1$H NMR ($CDCl_3$, δ): 1.47 (9H, s), 3.62–3.65 (2H, m), 4.08–4.15 (1H, m), 4.61–4.68 (1H, m), 5.35 (1H, d, J=8 Hz), 6.45 (1H, d, J=8 Hz), 6.64 (1H, br s), 6.97 (1H, t J=9 Hz), 7.18–7.52 (7H, m), 7.73–7.76 (1H, m), 7.83–7.86 (1H, m), 8.64–8.65 (1H, m), 8.72 (1H, d, J=1.6 Hz)

Preparation 43-4

The following compound was prepared in a similar manner to that of Preparation 36-2.

(3RS)-3-amino-2,3-dihydro-5-(2-fluorophenyl)-1-{2-(pyridin-3-yl)carbonylaminoethyl}-1H-1,4-benzodiazepin-2-one $^1H$ NMR ($CDCl_3$, δ): 2.0–2.4 (1H, m), 3.66 (2H, br s), 4.12–4.18 (1H, m), 4.54 (1H, s), 4.57–4.60 (1H, m), 6.90–7.60 (10H, m), 7.69–7.71 (1H, m), 7.88–7.91 (1H, m), 8.60–8.68 (1H, m), 8.78 (1H, d, J=2 Hz)

Preparation 44-1

The following compound was prepared in a similar manner to that of Preparation 29-2.

(3RS)-1- (5-acetylfuran-2-yl)methyl-3-tert-butoxycarbonyl-amino-5- (2-fluorophenyl )-2,3-dihydro-1H-1,4-benzodiazepin-2-one $^1H$ NMR ($CDCl_3$, δ): 1.43 (9H, s), 2.31 (3H, s), 5.05 (1H, d, J=16 Hz), 5.38–5.40 (2H, m), 6.34 (1H, m), 6.44 (1H, d, J=13 Hz), 6.95–7.05 (2H, m), 7.1–7.25 (3H, m), 7.44 (1H, m) 7.5–7.6 (2H, m), 7.70 (1H, m)

Preparation 44-2

The following compound was prepared in a similar manner to that of Preparation 36-2.

(3RS)-1-(5-acetylfuran-2-yl)methyl-3-amino-5-(2-fluorophenyl)-2,3-dihydro-1H-1,4-benzodiazepin-2-one $^1H$ NMR ($CDCl_3$, δ): 2.32 (3H, s), 2.35–2.5 (2H, m), 4.56 (1H, s), 5.68 (1H, d, J=16 Hz), 5.36 (1H, d, J=16 Hz), 6.36 (1H, m), 7.00–7.65 (9H, m)

Preparation 45-1

To a suspension of sodium hydride (0.076 g of a 64% dispersion in mineral oil) in N,N-dimethylformamide (2 ml) was added dropwise solution of (3RS)-3-tert-butoxycarbonylamino-5-cyclohexyl-2,3-dihydro-1H-1,4-benzodiazepin-2-one (0.498 g) in N,N-dimethylformamide (7 ml) under cooling in an ice-bath. After completion of the addition, the mixture was stirred at ambient temperature for 2 hours. To the mixture was added a solution of 2-acetyl-3-bromomethylthiophen (1.389 g) in N,N-dimethylformamide (3 ml) under cooling in an ice-bath. The mixture was stirred under the same condition for 30 minutes and then at ambient temperature overnight.

The mixture was concentrated in vacuo. The residue was treated with ethyl acetate, washed with water and dried over anhydrous sodium sulfate. Filtration and evaporation gave a crude product. The crude product was purified by column chromatography on silica gel with an eluent of a mixture of chloroform and methanol (100:1) to give (3RS)-1-(2-acetylthiophen-3-yl)methyl- 3-tert-butoxycarbonylamino-5-cyclohexyl-2,3-dihydro-1H-1,4-benzodiazepin-2-one (0.38 g).

$^1H$ NMR ($CDCl_3$, δ): 0.90–2.10 (19H, m), 2.51 (3H, s), 2.74 (1H, m), 5.22 (1H, d, J=8 Hz), 5.32 (1H, d, J=17 Hz), 5.64 (1H, d, J=17 Hz), 6.30 (1H, d, J=8 Hz), 6.94 (1H, d, J=5 Hz), 7.20–7.60 (5H, m)

Preparation 45-2

To a solution of (3RS)-1-(2-acetylthiophen-3-yl)methyl-3-tert-butoxycarbonylamino-5-cyclohexyl-2,3-dihydro-1H-1,4-benzodiazepin-2-one (0.379 g) in ethyl acetate (10 ml) was treated with hydrogen chloride under stirring. The mixture was extracted with water twice and 1N hydrogen chloride aqueous solution. The extracts were combined, alkalized with sodium bicarbonate and extracted with chloroform three times. The extracts were combined, dried over sodium sulfate and evaporated in vacuo to afford (3RS)-1-(2-acetylthiophen-3-yl)methyl-3-amino-5-cyclohexyl-2,3-dihydro-1H-1,4-benzodiazepin-2-one (0.25 g).

$^1H$ NMR ($CDCl_3$, δ): 0.90–2.20 (10H, m), 2.50 (3H, s), 2.73 (1H, m), 4.39 (1H, s), 5.37 (1H, d, J=17 Hz), 5.66 (1H, d, J=17 Hz), 6.93 (1H, d, J=5 Hz), 7.20–7.50 (5H, m)

Preparation 46-1

The following compound was prepared in a similar manner to that of Preparation 22-4.

(3RS)-1-(3-acetylpyridin-2-yl)methyl-3-tert-butoxycarbonyl-amino-5-cyclohexyl-2,3-dihydro-1H-1,4-benzodiazepin-2-one The mixture was purified by column chromatography on silica gel with an eluent of a mixture of hexane and ethyl acetate (4:1).

$^1H$ NMR ($CDCl_3$, δ): 1.10–1.37 (4H, m), 1.42 (9H, s), 1.57–1.70 (4H, m), 1.86 (1H, d, J=13 Hz), 2.07 (1H1, d, J=13 Hz), 2.65 (3H, s), 2.79 (1H, m), 5.21 (1H, d, J=18 Hz), 5.27 (1H, d, J=8 Hz), 5.49 (1H, d, J=18 Hz), 6.30 (1H, d, J=8 Hz), 7.20–7.40 (4H, m), 7.54 (1H, d, J=8 Hz), 8.06 (1H, d, J=8 Hz), 8.58 (1H, d, J=5 Hz)

Preparation 46-2

The following compound was prepared in a similar manner to that of Preparation 36-2.

(3RS)-1-(3-acetylpyridin-2-yl)methyl-3-amino-5-cyclohexyl-2,3-dihydro-1H-1,4-benzodiazepin-2-one $^1H$ NMR ($CDCl_3$, δ): 1.05–1.42 (4H, m), 1.61–1.73 (4H, m), 1.88 (1H, d, J=13 Hz), 2.04 (1H, d, J=13 Hz), 2.18 (2H, br s), 2.66 (3H, s), 2.79 (1H1, m), 4.34 (1H, s), 5.16 (1H, d, J=18 Hz), 5.52 (1H, d, J=18 Hz), 7.20–7.40 (4H, m), 7.53 (1H, m), 8.05 (1H, m), 8.59 (1H, m)

Preparation 47-1

To a suspension of sodium hydride (0.38 g of a 63.8% dispersion in mineral oil) in N,N-dimethylformamide (20 ml) was added slowly (3RS)-5-cyclohexyl-2,3-dihydro-3-phthalimido-1H-1,4-benzo(1iazepin-2-one (3.57 g) at 0°–5° C. in an ice-water bath under stirring. The mixture was stirred at the same condition for 30 minutes and then at room temperature for 1 hour. The mixture was cooled again in an ice-water bath. A solution of ethyl bromoacetate (1.69 g) in N,N-dimethylformamide (5 ml) was added dropwise to the cooled mixture. The mixture was allowed to warm to room temperature and stirred overnight. After treatment with acetic acid (0.5 g) at room temperature for 30 minutes, the resultant mixture was concentrated in vacuo to dryness. The residue was treated with ethyl acetate (400 ml) and water (100 ml). The organic layer was washed with saturated sodium bicarbonate aqueous solution (100 ml) and a brine (100 ml), and concentrated in vacuo. The residue was dissolved with ethanol (45 ml) and tetrahydrofuran (35 ml). To the solution was added dropwise 1N aqueous sodium hydroxide (37 ml) at room temperature. After stirring for 2 hours at the same condition, the mixture was concentrated in vacuo to remove ethanol and tetrahydrofuran. The residual solution was acidified with 6N aqueous hydrochloric acid and extracted with ethyl acetate (2×150 ml). The extracts were washed with water (50 ml) and dried over magnesium sulfate. Filtration and evaporation gave (3RS)-5-cyclohexyl-2,3-dihydro- 3-phthalimido-1-hydroxycarbonylmethyl-111-1,4-benzodiazepin-2-one (2.92 g) as a yellow crystal. The compound was used in a following reaction step without further purification.

$^1H$ NMR (DMSO-$d_6$, δ): 1.00–1.90 (10H, m), 2.95 (1H, t, J=6 Hz), 4.51 (1H, d, J=16 Hz), 4.66 (1H, d, J=16 Hz), 5.37 (1H, d, J=6 Hz), 7.20–7.82 (8H, m), 12.80 (1H, s)

Preparation 47-2

To a suspension of (3RS)-5-cyclohexyl-2,3-dihydro-3-phthalimido-1-hydroxycarbonylmethyl-1I-1,4-benzodiazepin-2-one (1.90 g) in ethyl acetate (80 ml) was added 1-hydroxy-1H-benzo-triazole monohydrate (0.76 g) and dicyclohexylcarbodiimide (0.94 g) at room temperature. The mixture was stirred at the same condition for 3 hours. To the mixture was added dropwise a solution of 3-azabicyclo[3.2.2]nonane (0.57 g) in ethyl acetate (20 ml). The reaction mixture was stirred at ambient temperature overnight. The resultant precipitate was filtered off by suction. The filtrate was concentrated in vacuo to give a crude product. The product was subjected by column chromatography on silica gel with chloroform and a mixture of chloroform and methanol (10:1) as eluents to afford (3RS)-1-[(3-azabicylo-[3.2:2]non-3-yl)carbonylmethyl-5-cyclohexyl-2,3-dihydro- 3-phtha-Limido-1H-1,4-benzodiazepin-2-one (1.0 g) as a yellow crystal.

$^1$H NMR ($CDCl_3$,δ): 1.00–2.00 (20H, m), 2.84 (1H, m), 3.40–3.80 (4H, m), 4.23 (1H, d, J=16 Hz), 5.04 (1H, d, J=16 Hz), 5.90 (1H, s), 7.04–7.64 (4H, m), 7.68–7.94 (4H, m)

Preparation 47-3

To a solution of (3RS)-1-[(3-azabicylo[3.2.2]non-3-yl)-carbonylmethyl-5-cyclohexyl-2 ,3-dihydro-3-phthalimido-1H-1,4:-benzodiazepin-2-one (1.0 g) in tetrahydrofuran (50 ml) was added hydrazine monohydrate (0.09 g) at ambient temperature. The mixture was stirred at the same condition for 2 hours and then heated under reflux temperature for 2 hours. The reaction mixture was allowed to cool to room temperature. The resultant precipitate was filtered off by suction. The filtrate was concentrated in vacuo. The residue was treated with 2N aqueous hydrochloric acid (20 ml) and washed with ethyl acetate (50 ml). The aqueous layer was separated and alkalized with sodium bicarbonate. The resultant crystal was extracted with ethyl acetate (2×150 ml). The extracts were combined, washed with a brine and dried over sodium sulfate. Filtration and evaporation gave (3RS)-3-amino-1-[(3-azabicylo[3.2.2]non-3-yl)carbonylmethyl-5-cyclohexyl-2,3-dihydro-1H-1,4-benzodiazepin-2-one (0.77 g).

$^1$H NMR ($CDCl_3$, δ): 1.00–2.00 (20H, m), 2.00–2.20 (2H, m), 2.90 (1H, m), 3.40–4.00 (4H, m), 4.23 (1H, d, J=16 Hz), 4.44 (1H, s), 5.04 (1H, d, J=16 Hz), 7.20–7.60 (4H, m)

Preparation 48-1

To a solution of cyclopentyl bromide (2M in diethyl ether, 317 ml.) was added dropwise a solution of 2-amino benzonitrile (25.0 g) in dry diethyl ether (400 ml) at 5°–10° C. under stirring for 2 hours. After completion of the addition, the mixture was allowed to warm to room temperature and then stirred at ambient temperature overnight. The reaction mixture was treated with 5N aqueous hydrochloric acid (150 ml) at 10°–20° C. and then stirred at room temperature for additional 30 minutes. To the mixture was added dropwise 5N sodium hydroxide aqueous solution. The resultant mixture was filtered by suction to remove an insoluble inorganic material. The organic layer was separated from the filtrate. The aqueous layer was extracted with ethyl acetate (2×200 ml). The organic layer and the extracts were combined and washed with a brine (100 ml). Dryness over sodium sulfate and evaporation under reduced pressure gave a crude product. The product was subjected by column chromatography on silica gel with a mixture of n-hexane and ethyl acetate (10:1) as an eluent to give !-cyclopentylcarbonylaniline (37.4 g) as a yellow oil.

$^1$H NMR ($CDCl_3$, δ): 1.60–1.70 (2H, m), 1.70–1.80 (2H, m), 1.80–1.95 (4H, m), 3.72 (1H, tt, J=10 Hz J=10 Hz), 6.26 (2H, s), 6.63–6.68 (2H, m), 7.22–7.26 (1H, m), 7.80 (1H1, d, J=5 Hz)

Preparation 48-2

The following compound was prepared in a similar manner to that of Preparation 34-2.

N-bromomethylcarbonyl-2-cyclopentylcarbonylaniline $^1$H NMR ($CDCl_3$, δ): 1.66–1.72 (2H, m), 1.73–1.79 (2H, m), 1.78–1.97 (4H, m), 3.77 (1H, q, J=8 Hz), 4.01 (2H, s), 7.18 (1H, t, J=9 Hz), 7.53 (1H, t, J=9 Hz), 7.96 (1H, d, J=5 Hz), 8.69 (1H, d, J=5 Hz)

Preparation 48-3

The following compound was prepared in a similar manner to that of Preparation 34-3.

5-cyclopentyl-4-oxy-2,3-dihydro-1H-1,4-benzodiazepin-2-one $^1$H NMR ($CDCl_3$, δ): 1.45–1.64 (2H, br), 1.64–1.90 (4H, br), 1.90–2.05 (2H, br), 3.30 (1H, m), 4.10 (1H, d, J=12 Hz), 4.61 (1H, d, J=12 Hz), 7.21 (1H, d, J=16 Hz), 7.26 (1H, t, J=8 Hz), 7.43 (1H, t, J=8 Hz), 7.51 (1H, d, J=16 Hz)

Preparation 48-4

The following compound was prepared in a similar manner to that of Preparation 34-4.

(3RS)-3-acetoxy-5-cyclopentyl-2,3-dihydro-1H-1,4-benzodiazepin-2-one $^1$H NMR ($CDCl_3$, δ): 1.45–1.60 (2H, br), 1.65–1.85 (4H, br), 1.90–2.20 (2H, br), 2.50 (3H, s), 3.20–3.40 (1H, br, s), 7.09–7.62 (4H, m)

Preparation 48-5

The following compound was prepared in a similar manner to that of Preparation 34-5.

(3RS)-5-cyclopentyl-2,3-dihydro-3-phthalimido-1H-1,4-benzodiazepin-2-one $^1$H NMR (DMSO-$d_6$, δ): 1.12–1.27 (2H, m), 1.47–1.85 (4H, m), 2.02–2.10 (2H, m), 3.46–3.56 (1H, m), 5.52 (1H, s), 7.26 (1H, d, J=8 Hz), 7.33 (1H, t, J=8 Hz), 7.58 (1H, t, J=8 Hz), 7.80 (1H, d, J=8 Hz), 7.89–7.98 (4H, m)

Preparation 48-6

To a solution of 3-azabicyclo[3.2.2]nonane (1.25 g) in dichloromethane (20 ml) and water (0.75 ml) was added dropwise a solution of bromoacetyl bromide (2.02 g) in dichloromethane (10 ml) at, 5°–10° C. The mixture was allowed to warm to room temperature and stirred for 1 hour at the same temperature. The reaction mixture was washed with a saturated sodium bicarbonate aqueous solution (10 ml) and a brine (10 ml). The organic layer was dried over magnesium sulfate. Filtration and evaporation gave N-bromomethylcarbonyl-3-azabicyclo[3.2.2]nonane (1.15 g). The compound was used in a following reaction step without further purification.

$^1$H NMR ($CDCl_3$, δ): 1.60–1.80 (8H, m), 2.02–2.30 (2H, br), 3.60 (2H, m), 3.73 (2H, m), 3.93 (2H, s)

Preparation 48-7

The following compound was prepared in a similar manner to that of Preparation 1-1.

(3RS)-1-(3-azabicyclo[3.2.2]non-3-yl) carbonylmethyl-5-cyclopentyl-2,3-dihydro-3-phthalimido-1H-1,4-benzodiazepin-2-one $^1$H NMR ($CDCl_3$, δ): 1.20–2.20 (18H, m), 3.33 (1H, t, J=8 Hz), 3.44–3.84 (4H, m), 4.25 (1H, d, J=18 Hz), 5.05 (1H, d, J=18 Hz), 5.92 (1H, s), 7.04–7.68 (4H, m), 7.69–7.94 (4H, m)

Preparation 48-8

The following compound was prepared in a similar manner to that of Preparation 47-3.

(3RS)-3-amino-5-(3-azabicyclo[3.2.2]non-3-yl) carbonylmethyl-5-cyclopentyl-1,3-dihydro-1H-1,4-benzodiazepin-2-one $^1$H NMR ($CDCl_3$, δ): 1.25–2.22 (18H, m), 3.20–3.32 (1H, m), 3.44–3.89 (4H, m), 4.25 (1H, d, J=16 Hz), 4.43 (1H, s), 5.00 (1H, d, J=16 Hz), 7.08–7.61 (4H, m), 8.60–8.76 (2H, br)

Preparation 49-1

The following compound was prepared in a similar manner to that of Preparation 5-2.

The crude compound was purified by column chromatography on silica gel with chloroform and a mixture of chloroform and ethyl acetate (5:1) as eluents.

(3RS)-3-amino-5-cyclopentyl-2,3-dihydro-1H-1,4-benzodiazepin-2-one $^1$H NMR ($CDCl_3$, δ): 1.24–2.10 (8H, m), 2.71–3.06 (3H,m), 4.32 (1H, s), 7.09–7.59 (4H, m), 8.76–8.88 (1H, br)

Preparation 49-2

The following compound was prepared in a similar manner to that of Example 47-1.

N-[(3RS)-5-cyclopentyl-2,3-dihydro-2-oxo-1H-1,4-benzodiazepin-3-yl]-N'-(3-methylphenyl)urea $^1$H NMR (DMSO-$d_6$, δ): 1.44–2.09 (8H, m), 2.23 (3H, s), 3.00–3.49 (1H, m), 5.02 (1H, d, J=8 Hz), 6.69 (1H, d, J=8 Hz), 7.07–7.30 (6H, m), 7.53 (1H, t, J=8 Hz), 7.78 (1H, d, J=8 Hz), 8.32 (1H, s), 8.89 (1H, s)

Preparation 50-1

To a suspension of magnesium (6.49 g) and a small amount of iodide in dry diethyl ether (100 ml) was added a solution of cycloheptylbromide (47.30 g) in dry diethyl ether (200 ml) under stirring at reflux temperature for 2 hours. After completion of the addition, the mixture was stirred at the same condition for additional 3 hours. To the mixture was added dropwise a solution of 2-amino benzonitrile (15.70 g) in dry diethyl ether (200 ml) at reilux temperature for 1 hour. The reaction mixture was stirred for additional 2 hours at the same condition and then was allowed to cool to room temperature. To the mixture was added dropwise 3N hydrochloric acid aqueous solution (150 ml) at 5°–10° C. for 2 hours.

The reaction mixture was heated under reflux temperature for 1 hour and then allowed to cool to room temperature. The organic layer was separated from the reaction mixture. The aqueous layer was alkalized with 3N sodium hydroxide aqueous solution (150 ml) and extracted with ethyl acetate (2×200 ml). The organic layer and extracts were combined and washed with a brine (100 ml). Dryness over sodium sulfate and evaporation gave a crude product (30.0 g) as a brown oil. The crude product was subjected by column chromatography on silica gel with chloroform as an eluent to give 2-cyclo-heptylcarbonylaniline (17.4 g) as a yellow oil.

$^1$H NMR ($CDCl_3$, δ): 1.20–2.00 (12H, m), 3.40–3.45 (1H, m), 6.20–6.32 (2H, br), 6.64 (2H, t, J=5.0 Hz), 7.26 (1H, t, J=4.0 z), 7.73 (1H, d, J=9 Hz)

Preparation 50-2

The following compound was prepared in a similar manner to that of Preparation 34-2.

N-bromomethylcarbonyl-2-cycloheptylcarbonylaniline $^1$H NMR ($CDCl_3$, δ): 1.37–2.05 (12H, m), 3.30–3.40 (1H, m), 5.51 (2H, s), 7.20–7.50 (4H, m), 8.70 (1H, s)

Preparation 50-3

The following compound was prepared in a similar manner to that of Preparation 34-3.

5-cycloheptyl-4-oxy-2,3-dihydro-1H-1,4-benzodiazepin-2-one $^1$H NMR (DMSO-$d_6$, δ): 1.46–1.66 (4H, br), 1.66–1.84 (4H, br), 1.84–2.04 (4H, br), 3.21–3.32 (1H, m), 4.10 (1H, d, J =13 Hz), 4.62 (1H, J=13 Hz), 7.19–7.52 (4H, m), 10.81 (1H, s)

Preparation 50-4

The following compound was prepared in a similar manner to that of Preparation 34-4.

(3RS)-3-acetoxy-5-cycloheptyl-2,3-dihydro-1H-1,4-benzodiazepin-2-one $^1$H NMR ($CDCl_3$, δ): 1.31–2.16 (12H, m), 2.30 (3H, s), 2.93–3.03 (1H, m), 5.79 (1H, s), 7.12 (1H, d, J=8 Hz), 7.26 (1H, t, J=8 Hz), 7.48 (1H, t, J=8 Hz), 7.59 (1H1, d, J=8 Hz), 8.74 (1H, s)

Preparation 50-5

The following compound was prepared in a similar manner to that of Preparation 34-5.

(3RS)-5-cycloheptyl-2,3-dihydro-3-phthalimido-1H-1,4-benzodiazepin-2-one $^1$H NMR (DMSO-$d_6$, δ): 1.23–1.96 (12H, m), 3.14–3.24 (1H, m), 5.45 (1H, s), 7.25 (1H, d, J=8 Hz), 7.31 (1H, t, J=8 Hz), 7.58 (1H, t, J=8 Hz), 7.78 (1H, d, J=8 Hz), 7.91–7.97 (4H, m), 10.83 (1H, s)

Preparation 50 -6

The following compound was prepared in a similar manner to that of Preparation 5-2.

The crude compound was purified by column chromatography on silica gel with chloroform and a mixture of chloroform and ethyl acetate (5:1) as eluents.

(3RS)-3-amino-5-cycloheptyl-2,3-dihydro-1H-1,4-benzodiazepin-2-one $^1$H NMR ($CDCl_3$, δ): 1.30–2.10 (12H, m) , 2.30–2.70 (2H, br), 2.85–3.00 (1H, m), 4.30 (1H, s), 7.09–7.58 (4H, m), 9.00 (1H, s)

Preparation 50-7

The following compound was prepared in a similar manner to that of Example 47-1.

N-[(3RS)-5-cycloheptyl-2,3-dihydro-2-oxo-1H-1,4-benzodiazepin-3-yl]-N'-(3-methylphenyl)urea Preparation 51

A mixture of (3RS)-3-amino-1-[(3-azabicyclo[3.2.2]non-3-yl]carbonylmethyl]-2,3-dihydro-5-(2-fluorophenyl)-1H-1,4-benzodiazepin-2-one (1.2 g) and carbonyldiimidazole (895 mg) was stirred at room temperature overnight. Ethyl acetate and water were added to the reaction mixture, and organic layer was separated, washed with water and brine, dried over magnesium sulfate, and evaporated in vacuo. The amorphous powder was washed with isopropyl ether to afford (3RS)-1-(3-azabicyclo[3.2.2]non-3-yl) carbonylmethyl-2,3-dihydro-3-(imidazol-1-yl) carbonylamino-5-(2-fluorophenyl)-1H-1,4-benzodiazepin-2-one (1.43 g).

NMR (DMSO-$d_6$, δ): 1.5–1.8 (8H, br) , 1.99 (2H, br), 3.56–3.58 (4H, br), 4.83 (1H, Jabq, 16.8 Hz, 28.1 Hz), 4.97 (1H, Jabq, 16.8 Hz, 28.1 Hz), 5.53 (1H, d, 7.7 Hz), 7.06 (1H, s), 7.0–7.7 (8H, m), 7.92 (1H, s), 8.45 (1H, s), 9.90 (1H, d, 7.7 Hz) IR (Nujol, $cm^{-1}$): 3300, 1722, 1670, 1638; Mass (FAB): 529 ($M^+$+1); mp: 235.2°–237.2° C.

Preparation 52

A mixture of 6-amino-1H-indazole (2.00 g) and pyridine (2.67 ml) in tetrahydrofuran was stirred at 0° C. and then p-nitrophenyl chloroformate (3.18 g) was added and stirred at the same temperature for 2 hours. The reaction mixture was evaporated and partitioned between ethyl acetate and water. The organic layer was washed with water and brine, dried over sodium sulfate, and evaporated in vacuo. The pale yellow powder was washed with isopropyl ether and diethyl ether, and vacuumed to afford 4-nitrophenyl N-(1H-indazol-6-yl)carbamate (2.67 g).

NMR (DMSO, δ): 6.0–9.1 (8H, m), 11.04 (1H, br s); Mass (APCI): 299 ($M^+$+1)

Preparation 53 4-Nitrophenyl N-(3-aminosulfonylphenyl) carbamate was obtained in a similar manner to that of Preparation 54.

NMR (DMSO-$d_6$, δ): 6.9–8.4 (8H, m), 9.07 (1H, s); IR (Nujol, $cm^{-1}$): 3250, 1750

Preparation 54

A mixture of 3-hydroxyaniline (2.0 g) and pyridine (3.3 ml) in tetrahydrofuran was stirred at 0° C. and then p-nitrophenyl chloroformate (3.88 g) was added, stirred at the same temperature for 5 hours. Ethyl acetate and 1N HCl were added to the reaction mixture, and the organic layer was separated, washed with water, dried over magnesium sulfate, and evaporated in vacuo. The yellow powder was washed with ethyl acetate to afford 4-nitro-phenyl N-(3-hydroxyphenyl)carbamate (554 mg).

NMR (DMSO-$d_6$, δ): 6.4–6.6 (1H, m), 6.9–7.2 (4H, m), 7.5–7.6 (1H, m), 8.1–8.3 (1H, m), 8.3–8.4 (1H, m); IR (Nujol, $cm^{-1}$): 3300, 1730, 1530; Mass (FAB): 275 ($M^+$+1)

Preparation 55-1

A mixture of 2-formyl-5-methylthiophene (12.6 g, 0.1 mol), methyl orthoformate (31.8 g) and a catalytic amount of p-toluene-sulfonic acid in toluene (120 ml) was refluxed for 6 hours. To the cooled reaction mixture was added ethyl acetate and washed with water twice. The organic layer was dried over magnesium sulfate. Removal of the solvent gave a brownish oil, which was purified by distillation under reduced pressure to afford 2-dimethoxymethyl-5-methylthiophene (13.54 g, 78.5% yield) as a yellow oil.

bp: 105°–107° C./20 mmHg; IR (neat, $cm^{-1}$): 1674, 1650(sh), 1480, 1450, 1346, 1310, 1221, 1184, 1160, 1090, 1045, 970, 900, 792, 664; $^1$H NMR ($CDCl_3$, δ) 2.46 (3H, s), 3.35 (6H, s), 5.54 (1H, s), 6.62 (1H, d, J=3.43 Hz), 6.85 (1H, d, J=3.43 Hz)

Preparation 55-2

To a mixture of 2-dimethoxymethyl-5-methylthiophene (3.44 g, 20 mmol) and N-bromosuccinimide (4.63 g, 26 mmol) in carbon tetrachloride (50 ml) was added a catalytic amount of benzoylperoxide. The mixture was refluxed for 1 hour. Undissolved materials were filtered off. The filtrate and the washings were combined and evaporated in vacuo to give 2-methoxycarbonyl-5-bromomethyl-thiophene as a yellow oil (4.65 g}, which was used in a following reaction without further purification.

Preparation 55-3

(3RS)-1-(5-methoxycarbonylthiophen-2-yl)methyl-3-tert-butoxycarbonylamino-5-(2-fluorophenyl)-2,3-dihydro-111-1,4-benzodiazepin-2-one was obtained in a similar manner to that of Preparation 16-2 as an amorphous mass.

APCI-MS (m/z): 524 ($M^+$+1); $^1$H-NMR ($CDCl_3$, δ): 1.48 (9H, s), 3.81 (3H, s), 5.30 (2H, ABq, J=15.7 Hz, 61.5 Hz), 5.38 (1H, d, J=8.7 Hz), 6.46 (1H, d, J=8.7 Hz), 6.85–7.75 (10H, m)

Preparation 55-4

(3RS)-3-amino-1-(5-methoxycarbonylthiophen-2-yl)methyl-5-(2-fluorophenyl)-2,3-dihydro-1H1,4-benzodiazepin-2-one was obtained in a similar manner to that of Preparation 16-5 as an amorphous mass.

APCI-MS (m/z): 424 ($M^+$+1); $^1$H-NMR ($CDCl_3$, δ) 2.70 (2H, br s), 3.50 (3H, s), 4.27 (1H, s), 5.07 (2H, ABq, J=15.8 Hz, 70.5 Hz), 6.6–7.3 (10H, m)

Preparation 56

4-Nitrophenyl N-[3-(3-oxo-2,3-dihydropyridazin-6-yl)phenyl]carbamate was obtained in a similar manner to that of Preparation 54.

NMR (DMSO-$d_6$, δ): 6.91–7.03 (3H, m), 7.35–7.50 (4H, m), 7.84–8.15 (3H, m), 9.02 (1H, s), 13.22 (1H, br s); IR (Nujol, $cm^{-1}$): 3305, 1658, 1600, 1540

Preparation 57

A mixture of 5-(3-nitrobenzoylamino)tetrazole (4.0 g), 10 palladium on carbon (1.0 g) in ethanol (200 ml) was stirred at room temperature in $H_2$ gas at 3 atm. for 4 hours. The reaction mixture was poured into 1N HCl and filtered. 1N sodium hydroxide was added to the filtrate and the pH was adjusted to 5–6 to afford the white powder. 5-(3-Aminobenzoylamino)tetrazole was obtained by filtration, washed with water, and vacuumed to dryness.

NMR (DMSO-$d_6$, δ): 6.79–6.84 (1H, m), 7.13–7.26 (3H, m), 12.1 (1H, s); IR (Nujol, $cm^{-1}$): 3460, 3200, 1675, 1610; Mass (APCI): 205 ($M^+$+1)

Preparation 58

4-Nitrophenyl N-(3-methoxycarbonylphenyl)carbamate was obtained in a similar manner to that of Preparation 54.

IR (Nujol.$cm^{-1}$): 3325, 1754, 1710, 1610, 1550, 1518, 1484, 1420, 1374, 1350, 1325, 1290, 1250, 1205, 1118, 1020, 980, 857, 748, 674; $^1$H-NMR (DMSO-$d_6$, δ): 3.87 (3H, s), 6.93 (2H, d, q, J=7.03 Hz, 3.44 Hz), 7.4–7.77 (3H, m), 8.12 (2H, d, q, J=7.03 Hz, 3.44 Hz), 8.22 (1H, t, J=1.78 Hz), 8.99 (1H, s), 11.05 (1H, s)

Preparation 59

4-Nitrophenyl N-(3-t-butoxycarbonylphenyl)carbamate was obtained in a similar manner to that of Preparation 54.

IR (Nujol, $cm^{-1}$): 3300, 1741, 1698, 1608, 1540, 1520, 1381, 1364, 1348, 1315, 1240, 1200, 1164, 1120, 1010, 930, 844, 752, 690; $^1$H-NMR ($CDCl_3$, δ): 1.60 (9H, s), 7.2 (1H, br s), 7.35–4.47 (3H, m), 7.77–7.80 (2H, m), 7.95 (1H, t, J=2 Hz), 8.29 (2H, d, t, J=9 Hz, 2 Hz)

Preparation 60

4-Nitrophenyl N-(3-methoxycarbonylmethylphenyl)carbamate was obtained in a similar manner to that of Preparation 54.

IR (Nujol, $cm^{-1}$): 3280, 1730, 1708, 1618, 1592, 1535, 1488, 1441, 1353, 1245, 1207, 1135, 1025, 877, 865, 770, 721, 685, 660; $^1$H-NMR ($CDCl_3$, δ): 3.64 (2H, s), 3.71 (3H, s), 7.07–7.47 (7H, m), 8.27 (2H, d, t, J=9.2 Hz, 3.2 Hz)

Preparation 61-1

A mixture of 3-nitrobenzonitrile (3.70 g, 25 mmol), sodium azide (4.88 g, 75 mmol) and triethylamine hydrochloride (10.32 g, 75 mniol) in N-methylpyrrolidone (55 ml) was heated at 130° C. for 2 hours under stirring. The reaction mixture was poured into ice-water, to which was dropwise added 6N hydrochloric acid in order to acidify. The resultant precipitates were collected by filtration, washed with water and dried to afford 5-(3-nitrophenyl)-1H-tetrazole (4.45 g, 93.1%), which was used in a following reaction without further purification.

IR (Nujol, $cm^{-1}$): 3350, 3070, 2800–2300, 1620, 1525, 1374, 1347, 1085, 1021, 960, 870, 820, 740, 725, 710; APCI-MS ($CHCl_3$) (m/z): 192 ($M^+$+1)

Preparation 61-2

5-(3-Nitrophenyl)-1H-tetrazole (4.41 g) was hydrogenated in ethanol (50 ml) over 10% palladium on carbon (0.4 g) under 3 atmospheric pressure of hydrogen at ambient temperature. The reaction mixture was filtered through Celite® (Johns Manville) and washed with ethanol. The filtrate and the washings were combined and evaporated to give 5-(3-aminophenyl)-1H-tetrazole as a crystalline powder, which was triturated in diisopropyl ether and collected by filtration to afford the desired product as a white powder (3.19 g, 85.8%). This was used in a following reaction without further purification.

IR (Nujol, $cm^{-1}$): 3400, 3300, 3200, 2800–2300, 1615, 1590, 1565, 1490, 1375, 1264, 1100, 1021, 1010, 996, 875, 865, 800, 745; APCI-MS (MeOH) (m/z): 162 ($M^+$+1)

Preparation 61-3

4-Nitrophenyl N-[3-(tetrazol-5-yl)phenyl]carbamate was obtained in a similar manner to that of Preparation 54.

Preparation 62-1

5-(3-Nitrophenyl)methyl-1H-tetrazole was obtained in a similar manner to that of Preparation 61-1.

IR (Nujol, $cm^{-1}$): 3100–2300, 1571, 1520, 1410, 1351, 1330, 1270, 1258, 1195, 1100, 1075, 1050, 890, 820(sh), 815, 772, 728; $^1$H-NMR (DMSO-$d_6$, δ): 4.48 (2H, s), 7.64 (1H, t, J=7.8 Hz), 7.76 (1H, d, J=7.8 Hz), 8.15 (1H, d, J=7.8 Hz), 8.25 (1H, s); APCI-MS ($CHCl_3$) (m/z): 206 ($M^+$1+1)

Preparation 62-2

5-(3-Aminobenzyl)-1H-tetrazol was obtained in a similar manner to that of Preparation 61-2.

IR (Nujol, $cm^{-1}$): 3400, 3300, 2750–2300, 1605, 1404, 1375, 1110, 1054, 760; $^1$H-NMR (DMSO-$d_6$, δ): 4.10 (2H, s), 6.35–6.46 (3H, m), 6.95 (1H, t, J=7.83 Hz); APCI-MS (DMF) (m/z): 176 ($M^+$+1)

Preparation 62-3

4-Nitrophenyl N-[3-(tetrazol-5-yl)methylphenyl] carbamate was prepared in a similar manner to that of Preparation 54.

Preparation 63-1

To a mixture of O-benzylglycine p-toluenesulfonic acid salt (6.41 g) and triethylamine (4.04 g) in methylene chloride (100 ml) was added portionwise 3-nitrobenzoyl chloride (3.71 g) under cooling in an ice-bath and stirring. The resultant mixture was stirred for 1 hour under the same condition and for 1 hour further at ambient temperature. From the reaction mixture, methylene chloride was removed in vacuo and to the residue were added water and ethyl acetate with stirring. The separated organic layer was washed with diluted hydrochloric acid, aqueous sodium bicarbonate and water twice respectively. The extract was dried over magnesium sulfate and evaporated in vacuo to give N-(3-nitrobenzoyl)glycine benzyl ester (5.98 g). $^1$H-NMR ($CDCl_3$, δ): 4.31 (2H, d, J=5.2 Hz), 5.24 (2H, s), 6.99 (1H, br, t, J=5.2 Hz), 7.38 (5H, s), 7.64 (1H, t, J=7.9 Hz), 8.15 (1H, d, t, J=7.9 Hz, 2.2 Hz), 8.35 (1H, d, t, J=7.9 Hz, 2.2 Hz), 8.64 (1H, t, J=2.2 Hz); APCI-MS ($CHCl_3$) (m/z): 315 ($M^+$+1)

Preparation 63-2

To a solution of N-(3-nitrobenzoyl)glycine benzyl ester (5.98 g) in 90% aqueous ethanol (150 ml) was added ammonium chloride (3.56 g). To the mixture was added portionwise iron powder (5.31 g) under stirring and refluxing. After the addition was completed, the mixture was refluxed for 2 hours under stirring. The reaction mixture was hot-filtered. The filtrate and the washings were combined and evaporated in vacuo. To the aqueous residue were added water and ethyl acetate under stirring. The separated organic layer was washed with water twice and dried over magnesium sulfate. Removal of the solvent gave N-(3-aminobenzoyl)glycine benzyl ester (4.03 g) as a viscous oil, which was used in a following reaction without further purification.

IR (film, $cm^{-1}$): 3400(sh), 3320, 1730, 1650, 1625, 1520, 1487, 1450, 1400(sh), 1380, 1355, 1320, 1250, 1185, 1078, 1040, 1012, 991, 950, 800, 746, 690; $^1$H-NMR ($CDCl_3$, δ): 3.47 (2H, br), 4.25 (2H, d, J=5.2 Hz), 5.22 (2H, s), 6.70 (1H, br, s), 6.7–6.81 (1H, m), 7.0–7.36 (8H, m), APCI-MS ($CHCl_3$) (m/z): 285 ($M^+$+1)

Preparation 63-3

4-Nitrophenyl N-[3-(benzyloxycarbonylmethylaminocarbonyl)-phenyl] carbamate was obtained in a similar manner to that of Preparation 54.

Preparation 64-1

To a solution of p-toluenesulfonic acid salt of L-alanine benzyl ester (7.03 g, 0.02 mol) and triethylamine (4.55 g, 0.045 mol) in methylene chloride (80 ml) was added dropwise a solution of 3-nitrobenzoyl chloride (3.71 g, 0.02 mol) in methylene chloride (20 ml) under ice-cooling and stirring. After the addition was completed, the mixture was stirred for 0.5 hour under the same condition and for 0.5 hour at ambient temperature. The mixture was washed with diluted hydrochloric acid and water twice successively. After drying over $MgSO_4$, the solvent was removed in vacuo to give N-(3-nitrobenzoyl)-L-alanine benzyl ester (6.54 g, 99.6% yield) as a colorless crystal, which was used in a following reaction without further purification. $^1$H-NMR (CDCl3, δ): 1.56 (3H, d, J=7.2 Hz), 4.86 (1H, q, J=7.2 Hz), 5.24 (2H, dd, J=12.3 Hz, 13.6 Hz), 6.98 (1H, br, d, J=7.0 Hz), 7.37 (5H, s), 7.63 (1H, t, J=8.0 Hz), 8.14 (1H, dd, J=1.2Hz, 8.0 Hz), 8.35 (1H, d, t, J=8.0 Hz, 0.92 Hz), 8.62 (1H, t, J=0.92 Hz); APCI-MS: 329 ($M^+$+1)

Preparation 64-2

To a solution of N-(3-nitrobenzoyl)-L-alanine benzyl ester (5.0 g, 15.2 mmol) and ammonium chloride (8.2 g, 0.152 mol) in 90% aqueous ethanol (150 ml) was added portionwise iron powder (4.25 g, 76.1 mmol) under refluxing and stirring, which were continued for an additional 1 hour. The mixture was hot-filtered through Celite® (Johns Manville) and washed with hot aqueous ethanol. The filtrate was evaporated in vacuo to give a residue, which was extracted with ethyl acetate and the organic extract was washed with brine twice. After drying over $MgSO_4$, the solvent was removed in vacuo to afford a viscous oil, which was crystallized soon on standing to give N-(3-aminobenzoyl)-L-alanine benzyl ester (4.5 g, 99.2% yield).

This was used in a following reaction without further purification. $^1$H-NMR ($CDCl_3$, δ): 1.51 (3H, d, J=7.1 Hz), 3.47 (2H, br), 4.83 (1H, q, J=7.1 Hz), 5.21 (2H, dd, J=12.3 Hz, 13.7 Hz), 6.72 (1H, br, d, J=6.8 Hz), 6.78 (1H, d, t, J=7.6 Hz, 1.5 Hz), 7.05–7.23 (3H, m), 7.36 (5H, s); APCI-MS: 299 ($M^+$+1)

Preparation 64-3

To a solution of N-(3-aminobenzoyl)-L-alanine benzyl ester (3.94 g, 13.21 mmol) and pyridine (1.15 g, 14.53 mmol) in dry tetrahydrofuran (50 ml) was dropwise a solution of 4-nitrophenyl chloroformate (2.88 g, 13.87 mmol) in dry tetrahydrofuran (5 ml) under cooling below 0° C. in an ice-bath and stirring. After the addition was completed, the mixture was stirred for 3 hours under the same condition. Tetrahydrofuran was removed in vacuo and to the residue were added ethyl acetate and water, and stirred vigorously. The separated organic layer was washed with water twice and dried over magnesium sulfate. Removal of the solvent in vacuo gave an amorphous mass of 4-nitrophenyl N-[3-[((1L)-1-benzyloxycarbonylethyl) aminocarbonyl]phenyl]carbamate (6.05 g, 98.8% yield), which was used in a following reaction (Example 107) without further purification.

Preparation 65-1

N-(3-nitrobenzoyl)-L-glutamic acid diethyl ester was obtained in a similar manner to that of Preparation 64-1.

IR (Nujol, $cm^{-1}$): 3330, 1735, 1726, 1638, 1614(sh), 1520, 1460, 1423, 1394, 1373, 1350, 1311, 1204, 1182, 1160, 1120, 1095, 1020, 918, 840, 818, 725; $^1$H-NMR ($CDCl_3$, δ): 1.25 (3H, t, J=7.1 Hz), 1.32 (3H, t, J=7.1 Hz), 2.1–2.7 (4H, m), 4.1–4.3 (4H, m), 4.25–4.83 (1H, m), 7.62 (1H, br, d, J=7.9 Hz), 7.65 (1H, t, J=7.8 Hz), 8.18 (1H, d, t, J=1.5 Hz, 7.8 Hz), 8.35 (1H, d, t, J=1.5 Hz, 7.8 Hz), 8.68 (1H, t, J=1.5 Hz); APCI-MS: 353 ($M^+$+1)

Preparation 65-2

N-(3-aminobenzoyl)-L-glutamic acid diethyl ester was obtained in a similar manner to that of Preparation 61-2. $^1$H-NMR ($CDCl_3$, δ): 1.24 (3H, t, J=7.13 Hz), 1.28 (3H, t, J=7.13 Hz), 2.0–2.55 (4H, m), 3.4–3.55 (2H, br), 4.10 (2H, q, J=7.13 Hz), 4.22 (2H, q, J=7.13 Hz), 4.79 (1H, m), 6.7–8.85 (1H, m), 7.0–7.3 (3H, m); APCI-MS ($CHCl_3$) (m/z): 323 ($M^+$+1)

Preparation 65-3

4-Nitrophenyl N-[3-(1,3-diethoxycarbonylpropylaminocarbonyl)pheny]carbamate was obtained in a similar manner to that of Prepartion 54.

This is used in a following reaction (Example 108) immediately after preparation.

EXAMPLE 1

To a solution of (3RS)-3-amino-2,3-dihydro-5-(2-fluorophenyl)-1-(2-oxo-2H-1-benzopyran-6-yl)methyl-1H-

1,4-benzodiazepin-2-one (214 mg) in dry methylene chloride (20 ml) was added dropwise a solution of 3-methylphenyl isocyanate (73 mg) in dry methylene chloride (10 ml) under nitrogen atmosphere at cooling in an ice-bath. The mixture was stirred under the same temperature for 1 hour and at ambient temperature overnight. The resultant precipitates were collected by filtration to afford a crude product. The crude product was purified by column chromatography on silica gel with eluents of chloroform and a mixture of chloroform and ethyl acetate to afford N-[(3RS)-2,3-dihydro-5-(2-fluorophenyl)-1-(2-oxo-2H-1-benzopyran-6-yl)methyl-2-oxo-1H-1,4-benzodiazepin-3-yl]-N'-(3-methylphenyl)urea as a colorless crystalline solid (200 mg).

mp: 260°–262° C. (dec.); $^1$H-NMR ($CDCl_3$, δ): 2.26 (3H, s), 5.14 (1H, d, J=15.0 Hz), 5.37 (1H, d, J=9.0 Hz), 5.55 (1H, d, J=15.0 Hz), 6.43 (1H, d, J=9.0 Hz), 6.75 (1H, d, J=9.0 Hz), 7.08–7.88 (16H, m), 9.00 (1H, s); IR (KBr) 3341, 1713, 1678, 1647, 1561 $cm^{-1}$; Mass (m/e): 560 ($M^+$+1)

EXAMPLE 2

To a solution of (3RS)-3-amino-1-(benzothiazol-2-yl)-methyl-2,3-dihydro-5-(2-fluorophenyl)-1H-1,4-benzodiazepin-2-one (110 mg) in dry methylene chloride (20 ml) was added dropwise a solution of 3-methylphenyl isocyanate (39 mg) in dry methylene chloride (5 ml) under nitrogen atmosphere at cooling in an ice-bath. The mixture was stirred under the same temperature for 1 hour and at ambient temperature overnight. The resultant precipitaltes were collected by filtration to afford a crude product. The crude product was purified by column chromatography on silica gel with eluents of chloroform and a mixture of chloroform and ethyl acetate (10:1), and by crystallization from a mixture of chloroform and isopropyl ether to afford N-[(3RS)-1-(benzothiazol-2-yl)methyl-2,3-dihydro-5-(2-fluorophenyl)-2-oxo-1H-1,4-benzodiazepin-3-yl]-N'-(3-methylphenyl)urea as a colorless crystalline solid (64 mg).

mp: 216°–217° C.; IR (KBr): 3321, 1688, 1646, 1611, 1560, 1489 $cm^{-1}$; $^1$H-NMR ($CDCl_3$, δ): 2.25 (3H, s), 5.40 (1H, d, J=10 Hz), 5.58 (1H, d, J=17 Hz), 5.74 (1H, d, J=17 Hz), 6.76 (1H, d, J=8 Hz), 7.06–8.00 (16H, m), 8.96 (1H, s); Mass (m/e): 549 ($M^+$+1)

EXAMPLE 3

To a solution of (3RS)-3-amino-2,3-dihydro-5-(2-fluorophenyl)-1-(thiomorpholin-4-yl)carbonylmethyl-1H-1,4-benzodiazepin-2-one (0.11 g) in dry methylene chloride (10 ml) was added dropwise a solution of 3-methylphenyl isocyanate (0.043 g) in dry methylene chloride (5 ml) at ambient temperature. After completion of addition, the mixture was stirred at the same condition overnight. The reaction mixture was concentrated in vacuo to afford a crude product. The product was purified by column chromatography on silica gel with an eluent of a mixture of chloroform and methanol (100:1) to afford N-[(3RS)-2,3-dihydro-5-(2-fluorophenyl)-2-oxo-1-(thiomorpholin-4-yl)carbonylmethyl-1H-1,4-benzodiazepin-3-yl)-N'-(3-methylphenyl)urea as a colorless crystalline solid (0.10 g).

mp: 157°–161° C.; IR (KBr): 3355, 1657, 1612, 1557, 1489, 1451, 1216 $cm^{-1}$; $^1$H-NMR (DMSO-$d_6$, δ): 2.24 (3H, s), 2.50–2.75 (4H, m), 3.70–3.80 (4H, m), 4.70 (1H, d, J=18 Hz), 4.93 (1H, d, J=18 Hz), 5.33 (1H, d, J=9 Hz), 6.75 (1H, d, J=9 Hz), 7.75–7.69 (12H, m), 8.98 (H, s); Mass (m/e): 546 ($M^+$+1)

To a solution of (3RS)-3-amino-2,3-dihydro-5-(2-fluorophenyl)-1-(pyridin-3-yl)methyl-1H-1,4- benzodiazepin-2-one (0.48 g) in dry methylene chloride (30 ml) was added dropwise a solution of 3-methylphenyl isocyanate (0.195 g) in dry methylene chloride (5 ml) under nitrogen atmosphere at cooling in an ice-bath. The mixture was stirred under the same temperature for 1 hour and at ambient temperature overnight. The resultant precipitates were collected by filtration and washed with isopropyl ether to afford N-[(3RS)-2,3-dihydro-5-(2-fluorophenyl)-2-oxo-1-(pyridin-3-yl)methyl-1H-1,4-benzodiazepin-3-yl]-N'-(3-methylphenyl)urea.

mp: 242°–243° C.; IR (KBr): 3318, 1677, 1644, 1614, 1560, 1490, 1449 $cm^{-1}$; $^1$H-NMR (DMSO-$d_6$, δ): 2.25 (3H, s), 5.11 (1H, d, J=15 Hz) 5.38 (1H, d, J=9 Hz), 5.54 (1H, d, J=15 Hz), 6.75 (1H, d, J=9 Hz), 7.00–7.90 (14H, m), 8.20–8.50 (2H, m) 9.00 (1H, s)

EXAMPLE 5

The following compound was prepared in a similar manner to that of Example 3. N-[(3RS)-2,3-dihydro-1-(3,5-dimethylisoxazol-4-yl)methyl-5-(2-fluorophenyl)-2-oxo-1H-1,4-benzodiazepin- 3-yl]-N'-(3-methylphenyl)urea.

mp: 225°–226° C.; IR (KBr): 3346, 1679, 1642, 1613, 1560, 1509, 1490, 1449, 1424, 1200 $cm^{-1}$; $^1$H-NMR (DMSO-$d_6$, δ): 1.82 (3H, s), 2.18 (3H, s), 2.24 (3H, s), 4.85 (1H, d, J=15 Hz), 5.27 (1H, d, J=9 Hz), 5.43 (1H, d, J=15 Hz), 6.77 (1H, d, J=9 Hz), 7.08–7.98 (12H, m), 8.95 (1H, s); Mass (m/e): 511 ($M^+$+1)

EXAMPLE 6

The following compound was obtained in a similar manner to that of Example 3.

N-[(3RS)-2,3-dihydro-5-(2-fluorophenyl)-2-oxo-1-(3-thienyl )methyl-1H-1,4-benzodiazepin-3-yl]-N'-(3-methylphenyl)urea mp: 221°–223° C.; IR (KBr):3313, 1674, 1644, 1613, 1560, 1489, 1217 $cm^{-1}$; $^1$H-NMR ($CDCl_3$, δ): 2.31 (3H, s) 5.03 (1H, d, J=15 Hz), 5.34 (1H, d, J=15 Hz), 5.63 (1H, d, J=8 Hz), 6.74–7.61 (15H, m); Mass (m/e): 499 ($M^+$+1)

EXAMPLE 7

The following compound was obtained in a similar manner to that of Example 3.

N-[(3RS)-2,3-dihydro-5-(2-fluorophenyl)-2-oxo-1-(quinolin-2-yl)methyl-1H-1,4-benzodiazepin-3-yl]-N'-(3-methylphenyl)urea mp: 224°–225° C.; IR (KBr): 3327, 1676, 1646, 1612, 1505, 1489, 1449, 1429 $cm^{-1}$; $^1$H-NMR (DMSO-$d_6$, δ): 2.25 (3H, s), 5.43 (1H, d, J=17 Hz), 5.45 (1H, s), 5.59 (1H, d, J=17 Hz), 6.75 (1H, d, J=9 Hz), 7.0–8.0 (18H, m), 8.27 (1H, d, J=9 Hz), 9.00 (1H, s)

EXAMPLE 8

The following compound was obtained in a similar manner to that of Example 3.

N-[(3RS)-2,3-dihydro-5-(2-fluorophenyl)-1-(2-furyl)-methyl-2-oxo-1H-1,4-benzodiazepin-3-yl]-N'-(3-methylphenyl)urea mp: 202°–206° C.; IR (KBr): 3314, 1680, 1647, 1612, 1558, 1489, 1450, 1215 $cm^{-1}$; $^1$H-NMR (DMSO-$d_6$, δ): 2.19 (3H, s), 5.03 (1H, d, J=16 Hz), 5.25 (1H, d, J=8 Hz), 5.39 (1H, d, J=16 Hz), 6.14 (1H, m), 6.24 (1H, m), 6.70 (1H, d, J=8 Hz), 7.02–7.83 (13H, m), 8.95 (1H, s); Mass (m/e): 483 ($M^+$+1)

EXAMPLE 9

The following compound was obtained in a similar manner to that of Example 3.

N-[(3RS)-2,3-dihydro-1-{2-(1,3-dioxolan-2-yl)ethyl}-5-(2-fluorophenyl)-2-oxo-1H-1,4-benzodiazepin-3-yl]-N'-(3-methyl-phenyl)urea mp: 214°–215° C.; IR (KBr): 3337, 1675, 1649, 1612, 1559, 1488, 1450, 1215 $cm^{-1}$; $^1H$-NMR (DMSO-$d_6$, δ): 1.59–1.73 (2H, m), 2.13 (3H, s), 3.64–3.91 (5H, m), 4.39–4.48 (1H, m), 4.38–4.51 (1H, m), 5.24 (1H, d, J=10 Hz), 6.73 (1H, d, J=10 Hz), 7.08–7.80 (12H, m), 8.99 (1H, s); Mass (m/e): 503 ($M^+$+1)

EXAMPLE 10

The following compound was obtained in a similar manner to that of Example 3.

N-[(3RS)-2,3-dihydro-5-(2-fluorophenyl)-2-oxo-1-(pyridin-2-yl)methyl-1H-1,4-benzodiazepin-3-yl]-N'-(3-methylphenyl)urea mp: 215°–216° C.; IR (KBr): 3330, 1679, 1645, 1612, 1559; 1489, 1450 $cm^{-1}$; $^1H$-NMR (DMSO-$d_6$, δ): 2.20 (3H, s), 5.15 (1H, d, J=16 Hz), 5.31 (1H, d, J=8 Hz), 5.35 (1H, d, J=16 Hz), 6.68 (1H, d, J=8 Hz), 7.0–7.8 (16H, m), 8.37 (1H, s), 8.94 (1H, s) Mass (m/e): 494 ($M^+$+1)

EXAMPLE 11

The following compound was obtained in a similar manner to that of Example 3.

N-[(3RS)-2,3-dihydro-5-(2-fluorophenyl)-2-oxo-1-(pyridin-4-Yl)methyl-lif-1,4-benzodiazepin-3-yl]-N'-(3-methylphenyl)urea mp: 228°–229 ° C.; IR (KBr): 3319, 1681, 1641, 1599, 1565, 1519, 1486, 1450 $cm^{-1}$; $^1H$-NMR (DMSO-$d_6$, δ): 2.24 (3H, s), 5.16 (1H, d, J=16 Hz), 5.40 (1H, d, J=10 Hz), 5.44 (1H, d, J=16 Hz), 6.74 (1H, d, J=10 Hz), 7.0–7.8 (14H, m), 8.40 (2H, d, J=8 Hz), 9.00 (1H, s); Mass (m/e): 493 ($M^+$+1)

EXAMPLE 12

The following compound was obtained in a similar manner to that of Example 2.

N-[(3RS)-1-(benzoxazol-2-yl)methyl-2,3-dihydro-5-(2-fluorophenyl)-2-oxo-1H-1,4-benzodiazepin-3-yl]-N'-(3-methylphenyl)urea mp: 209°–210° C.; IR (KBr): 3385, 1686, 1655, 1613, 1558, 1490 $cm^{-1}$; $^1H$-NMR ($CDCl_3$, δ): 2.26 (3H, s), 5.29 (1H, d, J=17 Hz), 5.47 (1H, d, J=16 Hz), 5.96 (1H, br), 6.65 (1H, s), 6.81 (1H, d, J=6 Hz), 6.90–7.76 (16H, m)

EXAMPLE 13-1

The following compound was obtained in a similar manner to that of Example 2.

N-[(3RS)-1-{3-azabicyclo[3.2.2]non-3-yl) carbonylmethyl}-2,3-dihydro-5-(2-fluorophenyl)-2-oxo-1H-1,4-benzodiazepin-3-yl]-N'-(3-methylphenyl)urea mp: 198°–199° C.; IR (KBr): 2932, 2864, 1686, 1654, 1612, 1557, 1485, 1451 $cm^{-1}$; $^1H$-NMR (DMSO-$d_6$, δ): 1.40–1.85 (8H, m), 1.95–2.15 (2H, m), 2.24 (3H, s), 3.40–3.55 (2H, m), 3.55–3.80 (2H, m), 4.71 (1H, d, J=16 Hz), 5.01 (1H, d, J=16 Hz), 5.33 (1H, d, J=10 Hz), 6.75 (1H, d, J=5 Hz), 7.00–7.80 (12H, m), 8.97 (1H, s); Mass: m/e= 568 ($M^+$+1)

EXAMPLE 13-2

The following compound was obtained in a similar manner to that of Example 1.

N-[(3RS)-1-{(3-azabicyclo[3.2.2]non-3-yl) carbonylmethyl}-2,3-dihydro-5-(2-fluorophenyl'-2-oxo-1H-1,4-benzodiazepin-3-yl]-N'-(3-methylthiophenyl)urea mp : 243°–244.5° C.; IR (Nujol, $cm^{-1}$): 3310, 3170, 1670, 1660(sh), 1645, 1635(sh), 1603, 1550, 1515, 1480, 1373, 1280, 1214, 1174, 770, 720; $^1H$-NMR (DMSO-$d_6$, δ): 1.45–1.8 (8H, br m), 1.9–2.1 (2H, br) 2.42 (3H, s), 3.44–3.78 (4H, m), 4.87 (2H, ABq, J=16.7 Hz, 58.1 Hz), 5.32 (1H, d, J=8.4 Hz), 6.82 (1H, d, J=8.3 Hz), 7.02 (1H, d, J=8.99 Hz), 7.1–7.7 (11H, m), 9.11 (1H, s); LC/MS (m/z): 600 ($M^{+1}$)

EXAMPLE 13-3

The following compound was obtained in a similar manner to that of Example 1.

N-[(3RS)-1-{(3-azabicyclo[3.2.2]non-3-yl) carbonylmethyl}-2,3-dihydro-5-(2-fluorophenyl)-2-oxo-1H-1,4-benzodiazepin-3-yl]-N'-(4-bromophenyl)urea mp: 188°–191° C.; IR (Nujol, $cm^{-1}$): 3390, 3250, 1685, 1664(sh), 1659, 1600, 1540, 1485, 1451, 1392, 1215, 820, 750; $^1H$-NMR (DMSO-$d_6$, δ): 1.45–1.8 (8H, br m), 1.9–2.1 (2H, br) 3.44–3.78 (4H, m), 4.87 (2H, ABq, J=16.7 Hz, 57.9 Hz), 5.32 (1H, d, J=8.4 Hz), 7.2–7.7 (13H, m), 9.20 (1H, s); LC/MS (m/z): 632 ($M^+$), 633 ($M^+$+1), 634 ($M^+$+2), 635 ($M^+$+3)

EXAMPLE 13-4

The following compound was obtained in a similar manner to that of Example 1.

N-[(3RS)-1-{(3-azabicyclo[3.2.2]non-3-yl) carbonylmethyl}-2,3-dihydro-5-(2-fluorophenyl)-2-oxo-1H-1,4-benzodiazepin-3-yl]-N'-(4-chlorophenyl)urea mp: 187°–190.5° C.; IR (Nujol, $cm^{-1}$): 3380, 3230, 1684, 1660, 1655, 1600(sh), 1595, 1540, 1484, 1451, 1372, 1217, 1202, 824, 750; $^1H$-NMR (DMSO-$d_6$, δ): 1.45–1.8 (8H, br m), 1.9–2.1 (2H, br) 3.44–3.78 (4H, m), 4.87 (2H, ABq, J=16.8 Hz, 58.2 Hz), 5.32 (1H, d, J=8.4 Hz), 7.2–7.7 (13H, m), 9.20 (1H, s); LC/MS (m/z): 588 ($M^+$+1), 589 ($M^+$+2), 590 ($M^+$+3), 591 ($M^+$+4)

EXAMPLE 13-5

The following compound was obtained in a similar manner to that of Example 1.

N-[(3RS)-1-{(3-azabicyclo[3.2.2]non-3-yl) carbonylmethyl}-2,3-dihydro-5-(2-fluorophenyl)-2-oxo-1H-1,4-benzodiazepin-3-yl]-N'-(4-chloro-3-trifluoromethyphenyl)urea mp: 244°–246° C.; IR (Nujol, cm $^1$): 3270, 1684, 1650, 1645, 1638(sh), 1606, 1530, 1470, 1413, 1322, 1258, 1224, 1174, 1124, 1029, 825, 756, 745, 715; $^1H$-NMR (DMSO-$d_6$, δ): 1.5–1.8 (8H, br m), 1.9–2.1 (2H, br) 3.44–3.78 (4H, m), 4.88 (2H, ABq, J=16.7 Hz, 56.3 Hz), 5.32 (1H, d, J=8.2 Hz), 7.2–7.73 (11H, m), 8.09 (1H, d, J=2.31 Hz), 9 54 (1H,s) LC/MS (m/z): 656 ($M^+$+1), 657 ($M^+$+2), 658 ($M^+$+3), 659 ($M^+$+4)

EXAMPLE 13-6

The following compound was obtained in a similar manner to that of Example 1.

N-[(3RS)-1-{(3-azabicyclo[3.2.2]non-3-yl) carbonylmethyl}-2,3-dihydro-5-(2-fluorophenyl)-2-oxo-1H-1,4-benzodiazepin-3-yl]-N'-(3-methoxyphenyl)urea mp: 182°–184° C.; IR (Nujol, $cm^{-1}$): 3380, 3250, 1684, 1656, 1604, 1555, 1495, 1455, 1375, 1217, 1154, 745, 720; $^1H$-NMR (DMSO-$d_6$, δ): 1.45–1.8 (8H, br m), 1.9–2.1 (2H, br) 3.44–3.78 (4H, m), 3.70 (3H, s), 4.87 (2H, ABq, J=16.8 Hz, 58. Hz), 5.33 (1H, d, J=8.5 Hz), 6.51 (1H, dd, J=2.2 Hz, 8.1 Hz), 6.82 (1H, d, J=7.9 Hz), 7.1–7.7 (11H, m) 9.07 (1H, s); LC/MS (m/z): 584 ($M^{+1}$)

EXAMPLE 13-7

To a solution of (3RS)-1-{(3-azabicyclo[3.2.2]non-3-yl)-carbonylmethyl}-3-amino-5-(2-fluorophenyl)-2,3-dihydro-1H-1,4-benzodiazepin-2-one (100mg) and 4-nitrophenyl N-(3-trifluoromethylphenyl)carbamate (90.1 mg) in dimethylformamide (2 ml) was added triethylamine (28 mg) under stirring at ambient temperature. The mixture was stirred for 3.5 hours under the same condition. The reaction mixture was poured into water and extracted with ethyl acetate. The extract was washed with water three times and dried over magnesium sulfate. The solvent was removed in vacuo to give an amorphous mass, which was pulverized in diisopropyl ether under vigorous stirring. The resulting powder was collected by filtration and washed with diisopropyl ether to afford N-[(3RS)-1-{(3-azabicyclo[3.2.2]non-3-yl)-carbonylmethyl}-2,3-dihydro-5-(2-fluorophenyl)-2-oxo-1H-1,4-benzodiazepin-3-yl]-N'-(3-trifluoromethylphenyl) urea (124.4 mg).

mp: 226°–227° C.; IR (Nujol, $cm^{-1}$): 3350, 3240, 1693, 1678, 1632, 1604, 1532, 1488, 1450, 1374, 1333, 1242, 1107, 1019, 941, 875, 760; $^1$H-NMR (DMSO-$d_6$, δ): 1.45–1.8 (8H, br m), 1.9–2.1 (2H, br) 3.44–3.76 (4H, m), 4.88 (2H, ABq, J=16.8 Hz, 56.7 Hz), 5.33 (1H, d, J=8.3 Hz), 7.2–7.75 (12H, m), 7.99 (1H, s), 9.44 (1H, s); LC/MS (m/z): 622 ($M^{+1}$)

EXAMPLE 13-8

The following compound was obtained in a similar manner to that of Example 13-7.

N-[(3RS)-1-{(3-azabicyclo[3.2.2]non-3-yl) carbonylmethyl}-2,3-dihydro-5-(2-fluorophenyl)-2-oxo-1H-1,4-benzodiazepin-3-yl]-N'-(indan-5-yl)urea mp: 164°–1669° C.; IR (Nujol, $cm^{-1}$): 3320(sh), 3280, 1683(sh), 1660(sh), 1650, 1600, 1540, 1485, 1450, 1374, 1325, 1265, 1210, 810, 748; $^1$H-NMR (DMSO-$d_6$, δ): 1.45–1.8 (8H, br m), 1.9–2.1 (4H, m), 2.7–2.9 (4H, m), 3.44–3.79 (4H, m), 4.86 (2H, ABq, J=16.8 Hz, 60.0 Hz), 5.32 (1H, d, J=8.5 Hz), 7.05–7.70 (12H, m), 8.91 (1H, s); LC/MS (m/z): 594 ($M^{+1}$)

EXAMPLE 13-9

The following compound was obtained in a similar manner to that of Example 13-7.

N-[(3RS )-1-{(3-azabicyclo [3.2.2]non-3-yl )carbonylmethyl}-2,3-dihydro-5-(2-fluorophenyl)-2-oxo-1H-1,4-benzodiazepin-3-yl]-N'-(2,1,3-benzothiadiazol-4-yl)urea mp: 229°–232.5° C.; IR (Nujol, $cm^{-1}$): 3300, 3250(sh), 3200(sh), 1674, 1650(sh), 1637, 1605, 1659, 1540, 1481, 1456, 1444, 1405, 1372, 1328, 1278, 1214, 1170, 1108, 925, 900, 826, 803, 765(sh), 754, 710; $^1$H-NMR (DMSO-$d_6$, δ): 1.45–1.8 (8H, br m), 1.9–2.1 (2H, br), 3.46–3.76 (4H, m), 4.89 (2H, ABq, J=16.8 Hz, 57.8 Hz), 5.42 (1H, d, J=8.4 Hz), 7.22–7.72 (10H, m), 8.16–8.20 (1H, m), 8.72 (1H, d, J=8.5 Hz), 9.83 (1H, s); LC/MS (m/z): 612 ($M^{+1}$)

EXAMPLE 13-10

The following compound was obtained in a similar manner to that of Example 13-7.

N-[(3RS)-1-{(3-azabicyclo[3.2.2]non-3-yl) carbonylmethyl}-2,3-dihydro-5-(2-fluorophenyl)-2-oxo-1H-1,4-benzodiazepin-3-yl]-N'-(3,5-dimethylphenyl)urea mp: 224.5°–229 ° C.; IR (Nujol, $cm^{-1}$): 3360, 3270, 1681, 1660(sh) 1650, 1610, 1569(sh), 1656, 1480, 1450, 1371, 1325, 1264, 1205, 1098, 999, 838, 784, 749, 724, $^1$H-NMR (DMSO-$d_6$, δ): 1.45–1.8 (8H, br m), 1.9–2.1 (2H, br), 2.20 (6H, s), 3.45–3.79 (4H, m), 4.87 (2H, ABq, J=16.8 Hz, 59.6 Hz), 5.31 (1H, d, J=8.4 Hz), 6.57 (1H, s), 7.0–7.7 (11H, m), 8.89 (1H, s); LC/MS (m/z): 582 ($M^{+1}$)

EXAMPLE 13-11

The following compound was obtained in a similar manner to that of Example 13-7.

N-[(3RS)-1-{(3-azabicyclo[3.2.2]non-3-yl) carbonylmethyl}2,3-dihydro-5-(2-fluorophenyl)-2-oxo-1H-1,4-benzodiazepin-3-yl]-N'-(1,4-benzodioxan-6-yl)urea mp: 162.5°–164 ° C. (dec.); IR (Nujol, $cm^{-1}$):3350, 3300, 1685(sh), 1670(sh), 1650, 1605, 1540, 1497, 1450, 1373, 1326, 1298, 1271, 1210(sh), 1196, 1066, 918, 886, 802, 751; $^1$H-NMR (DMSO-$d_6$, δ): 1.45–1.8 (8H, br m), 1.9–2.1 (2H, br) 3.44–3.76 (4H, m), 4.18 (4H, s), 4.86 (2H, ABq, J=16.8 Hz, 59.3 Hz), 5.31 (1H, d, J=8.5 Hz), 6.6–7.7 (12H, m), 8.87 (1H, s); LC/MS (m/z): 612 ($M^{+1}$)

EXAMPLE 13-12

The following compound was obtained in a similar manner to that of Example 13-7.

N-[(3RS)-1-{(3-azabicyclo[3.2.2]non-3-yl) carbonylmethyl}-2,3-dihydro-5-(2-fluorophenyl)-2-oxo-1H-1,4-benzodiazepin-3-yl]-N'-(3-cyclopropylmethoxyphenyl)urea mp: 220°–221.5° C.; IR (Nujol, $cm^{-1}$): 3390, 3250, 1684, 1655, 1608, 1548, 1490, 1450, 1374, 1260, 1215, 1203, 1180, 1151, 920, 910, 770, 750, 720; $^1$H-NMR (DMSO-$d_6$, δ): 0.25–0.33 (2H, m), 0.49–0.59 (2H, m), 1.1–1.3 (1H, m), 1.45–1.8 (8H, br m), 1.9–2.1 (2H, br m), 3.44–3.76 (6H, m), 4.87 (2H, ABq, J=16.8 Hz, 58.5 Hz), 5.32 (1H, d, J=8.5 Hz), 6.49 (1H, dd, J=1.9 Hz, 7.9 Hz), 6.79 (1H, d, J=7.9 Hz), 7.07–7.7 (11H, m), 9.05 (1H, s); LC/MS (m/z): 624 ($M^{+1}$)

EXAMPLE 13-13

The following compound was obtained in a similar manner to that of Example 13-7.

N-[(3RS)-1-{(3-azabicyclo[3.2.2]non-3-yl) carbonylmethyl}-2,3-dihydro-5-(2-fluorophenyl)-2-oxo-1H-1,4-benzodiazepin-3-yl]-N'-[3-(2-methylthioethoxy) phenyl]urea mp: 187°–189° C.; IR (Nujol, $cm^{-1}$): 3370, 3250(sh), 1684, 1660(sh), 1653, 1605, 1355, 1340(sh), 1490, 1458, 1374, 1260, 1210, 1155, 780, 720; $^1$H-NMR (DMSO-$d_6$, δ): 1.45–1.8 (8H, br m), 2.01 (2H, br m), 2.14 (3H, s), 2.82 (2H, t, J=6.5 Hz), 3.44–3.78 (6H, m), 4.08 (2H, t, J=6.5 Hz), 4.87 (2H, ABq, J=16.8 Hz, 58.1 Hz), 5.33 (1H, d, J=8.4 Hz), 6.52 (1H, dd, J=2.0 Hz, 7.9 Hz), 6.81 (1H, d, J=7.9 Hz), 7.1–7.7 (11H, m), 9.07 (1H, s); LC/MS (m/z): 644 ($M^{+1}$)

EXAMPLE 13-14

The following compound was obtained in a similar manner to that of Example 13-7.

N-[(3RS)-1-{(3-azabicyclo[3.2.2]non-3-yl) carbonylmethyl}-2,3-dihydro-5-(2-fluorophenyl)-2-oxo-1H-1,4-benzodiazepin-3-yl]-N'-(2-oxo-1,2,3,4-tetrahydroquinolin-6-yl)urea mp: 210°–213.5° C.; IR (Nujol, $cm^{-1}$): 3320, 3200(sh), 1685(sh), 1670(sh), 1651, 1608, 1556, 1496, 1448, 1373, 1325, 1212, 1196, 1005, 945, 820, 765(sh), 750; $^1$H-NMR (DMSO-$d_6$, δ): 1.45–1.8 (8H, br m), 1.9–2.1 (2H, br m), 2.39 (2H, t, J=8.1 Hz), 2.81 (2H, t, J=8.1 Hz), 3.44–3.78

(4H, m), 4.86 (2H, ABq, J=16.8 Hz, 59.4 Hz), 5.32 (1H, d, J=8.5 Hz), 6.72 (1H, d, J=8.5 Hz), 7.05–7.7 (11H, m), 8.87 (1H, s), 9.94 (1H, s); LC/MS (m/z): 623 ($M^+$)

EXAMPLE 13-15

The following compound was obtained in a similar manner to that of Example 13-7. Purification was performed by column chromatography on silica gel eluting with a mixture of chloroform and methanol(100:1).

N-[(3RS)-1-{(3-azabicyclo[3.2.2]non-3-yl) carbonylmethyl}-2,3-dihydro-5-(2-fluorophenyl)-2-oxo-1H-1,4-benzodiazepin-3-yl]-N'-[3-(2-methoxyethyl)phenyl] urea mp: 223°–224.5° C.; IR (Nujol, $cm^{-1}$): 3380, 3260, 1685, 1656, 1648(sh), 1610, 1555, 1490, 1455(sh), 1450, 1375, 1328, 1210, 1203, 1120, 1002, 933, 817, 770, 750 $^1$H-NMR (DMSO-$d_6$, δ): 1.45–1.8 (8H, br m), 1.9–2.1 (2H, br m), 2.73 (2H, t, J=6.8 Hz), 3.23 (3H, s), 3.50 (2H, t, J=6.8 Hz), 3.44–3.78 (4H, m), 4.87 (2H, AB1, J=16.7 Hz, 57.7 Hz), 5.33 (1H, d, J=8.5 Hz), 6.80 (1H, d, J=6.9 Hz), 7.09–7.7 (12H, m), 9.00 (1H, s); LC/MS (m/z): 612 ($M^{+1}$)

EXAMPLE 13-16

The following compound was obtained in a similar manner to that of Example 13-7.

N-[(3RS)-1-{(3-azabicyclo[3.2.2]non-3-yl) carbonylmethyl}-2,3-dihydro-5-(2-fluorophenyl)-2-oxo-1H-1,4-benzodiazepin-3-yl]-N'-(4-hydroxy-3-methylphenyl)urea mp: 190°–193.5° C. (dec.); IR (Nujol, $cm^{-1}$): 3350(sh), 3300, 1685(sh), 1650, 1635(sh), 1610, 1540, 1490, 1450, 1372, 1325, 1264, 1210, 1194, 1110, 1005, 810, 750; $^1$H-NMR (DMSO-$d_6$, δ): 1.45–1.8 (8H, br m), 1.9–2.1 (2H, br m), 2.06 (3H, s), 3.45–3.76 (4H, m), 4.86 (2H, ABq, J=16.6 Hz, 59.5 Hz), 5.31 (1H, d, J=8.6 Hz), 6.64(11H, d, J=8.5 Hz), 6.9–7.7 (11H, m), 8.64 (1H, s), 8.89 (1H, br s); LC/MS (m/z): 584 ($M^+$)

EXAMPLE 13-17

The following compound was obtained in a similar manner to that of Example 13-7.

N-[(3RS)-1-{(3-azabicyclo[3.2.2]non-3-yl) carbonylmethyl}-2,3-dihydro-5-(2-fluorophenyl)-2-oxo-1H-1,4-benzodiazepin-3-yl]-N'-(3,4-methylenedioxyphenyl)urea mp: 161°–163.5° C.; IR (Nujol, $cm^{-1}$): 3360, 3270, 1684, 1660(sh), 1650, 1635, 1610, 1558, 1485, 1450, 1374, 1325, 1210, 1181, 1034, 926, 750; $^1$H-NMR (DMSO-$d_6$, δ): 1.45–1.8 (8H, br m), 1.9–2.1 (2H, br m), 3.44–3.78 (4H, m), 4.86 (2H, ABq, J=16.7 Hz, 58.7 Hz), 5.31 (1H, d, J=8.5 Hz), 5.94 (2H, s), 6.66 (1H, dd, J =2 Hz, 8.4 Hz), 6.80 (1H, 8.5 Hz), 7.1–7.7 (1H, m), 8.95 (1H, s); LC/MS (m/z): 598 ($M^{+1}$)

EXAMPLE 13-18

The following compound was obtained in a similar manner to that ofC Example 13-7.

N-[(3RS)-1-{(3-azabicyclo[3.2.2]non-3-yl) carbonylmethyl}-2,3-dihydro-5-(2'-fluorophenyl)-2-oxo-1H-1,4-benzodiazepin-3-yl]-N'-(3-acetylphenyl)urea mp: 215.5°–219.5° C.; IR (Nujol, $cm^{-1}$): 3320, 3250(sh), 1684, 1653, 1645(sh), 1635(sh), 1608, 1548, 1515, 1485, 1450, 1374, 1325, 1276, 1215, 765, 720 $^1$H-NMR (DMSO-$d_6$, δ): 1.45–1.8 (8H, br m), 1.9–2.1 (2H, br m), 3.44–3.75 (4H, m), 4.87 (2H, ABq, J=16.7 Hz, 57.2 Hz), 5.34 (1H, d, J=8.3 Hz), 7.2–7.7 (12H, m), 8.03 (1H, s), 9.29 (1H, s); LC/MS (m/s): 596 ($M^{+1}$)

EXAMPLE 13-19

The following compound was obtained in a similar manner to that of Example 13-7.

N-[(3RS)-1{(3-azabicyclo[3.2.2]non-3-yl) carbonylmethyl-2,3-dihydro-5-(2-fluorophenyl)-2-oxo-1H-1,4-benzodiazepin-3-yl]-N'-[3-(2-mothylthioethoxycarbonyl)phenyl]urea mp:133°–136° C. (dec.); IR (Nujol, $cm^{-1}$):3320, 1710, 1685(sh), 1670(sh), 1650, 1605, 1546, 1483, 1458, 1449, 1374, 1325, 1275, 1104, 1008, 810, 750; $^1$H1-NMR (DMSO-$d_6$, δ): 145–1.8(8H, br m), 1.9–2.1 (2H, br m), 2.13 (3H1, s) 2.83 (2H, t, J=6.611z) 3.44–3.76 (4H, m), 4.42 (2H, t, J=6.6 Hz), 4.88 (2H, ABq, J=16.9 Hz, 56.9 Hz), 5.33 (11H, d, J=8.4 Hz), 7.2–7.7 (12H, m), 8.10 (1H, s), 9.32 (1H, s) LC/MS (m/z): 672 ($M^{+1}$)

EXAMPLE 13-20

The following compound was obtained in a similar manner to that of Example 13–7.

N-[(3RS)-1-{(3-azabicyclo[3.2.2]non-3-yl) carbonylmethyl}-2,3-dihydro-5-(2-fluorophenyl)- 2-oxo-1H-1,4-benzodiazepin-3-yl]-N'-[3-((E)-methoxyiminoinethyl)phenyl]urea mp:197.5°–200.5 ° C. IR (Nujol, $cm^{-1}$): 3375, 3270, 1680, 1655(sh), 1648, 1604, 1580, 1555, 1481, 1458, 1450, 1374, 1204, 1058, 1050, 908, 785; $^1$H-NMR (DMSO-$d_6$, δ): 1.45–1.8 (8H, br m), 1.9–2.1 (2H, br m), 3.44–3.76 (4H, m), 3.87 (3H, s), 4.87 (2H, ABq, J=16.8 Hz, 56.9 Hz), 5.33 (1H, d, J=8.4 Hz), 7.13–7.7 (12H, m), 7.78 (1H, s), 8.16 (1H, s), 9.18 (1H, s); L,C/MS (m/z): 611 ($M^{+1}$)

EXAMPLE 13-21

The following compound was obtained in a similar manner to that of Example 13-7.

N-[(3RS)-1-{(3-azabicyclo[3.2.2]non-3-yl) carbonylmethyl}-2,3-dihydro-5-(2-fluorophenyl)-2-oxo-1H-1,4-benzodiazepin-3-yl]-N'-[3-((E)-2-methoxycarbonylvinyl)phenyl]urea mp: 165°–170 ° C.; IR (Nujol, $cm^{-1}$) 3330, 3280(sh), 1710(sh), 1685(sh), 1650, 1635(sh), 1605, 1545, 1485, 1455(sh), 1450, 1374, 1330, 1270, 1210, 1198, 1165, 1104, 1010, 980, 855, 750, 685 $^1$H-NMR (DMSO-$d_6$, δ): 1.45–1.8 (8H, br m), 1.9–2.1 (2H, br m), 3.44–3.72 (4H, m), 3.71 (3H, S), 4.87 (2H, ABq, J=16.8 Hz, 57.7 Hz), 5.34 (1H, d, J=8.4 Hz), 6.51 (1H, d, J=16.1 Hz), 7.2–7.7 (14H, m), 9.17 (1H, s); L,C/MS (m/z): 638 ($M^{+1}$)

EXAMPLE 13-22

The following compound was obtained in a similar manner to that of Example 13-7.

N-[(3RS)-1-{(3-azabicyclo[3.2.2]non-3-yl) carbonylmethyl}-2,3-dihydro-5-(2-fluorophenyl)-2-oxo-1H-1,4-benzodiazepin-3-yl]-N'-(5-indolyl)urea mp: 183.5°–186° C. (dec.); IR (Nujol, $cm^{-1}$): 3350(sh), 3290, 1690(sh), 1655, 1646, 1610, 1550, 1482, 1458, 1450, 1374, 1324, 1260, 1212, 1100, 1001, 805, 755, 720; $^1$H-NMR (DMSO-$d_6$, δ): 1.45–1.8 (8H, br m), 1.9–2.1 (2H, br m), 3.45–3.76 (4H, m), 4.83 (2H, ABq, J=16.7 Hz, 59.7 Hz), 5.36 (1H, d, J=8.6 Hz), 6.31 (1H, br s), 7.02 (1H, dd, J=2.0 Hz, 8.7 Hz), 7.2–7.7 (12H, m), 8.78 (1H, s), 10.91 (1H, s); LC/MS (m/z): 593 ($M^{+1}$)

EXAMPLE 13-23

To a solution of N-[(3RS)-1-hydroxycarbonylmethyl-5-(2-fluorophenyl)-2,3-dihydro-2-oxo-1H-1,4-benzodiazepin-3-yl]-N'-(3-methylphenyl)urea (0.295 g) and 8-methyl-3,8-diazabicyclo[3.2.1]octane dihydrochloride (0.189 g) in N,N-dimethylformamide (10 ml) was added 1-ethyl-3-(3'-dimethylaminopropyl)carbodiimide hydrochloride (0.150 g), 1-hydroxy-1H-benzotriazole monohydrate (0.120 g) and a solution of triethylamine (0.255 g) in N,N-dimethylformamide (2 ml). The. mixture was stirred overnight at ambient temperature. Then the mixture was heated at 80° C. for 1 hour. The mixture was concentrated in vacuo. The residue was treated with water, alkalized with sodium carbonate and extracted with chloroform. The extract was dried over sodium sulfate and concentrated in vacuo. The residue was purified by column chromatography on silica gel with an eluent of a mixture of chloroform and methanol (50:1) to give N-[(3RS)-5-(2-fluorophenyl)-I-(8-methyl-3,8-diazabicyclo[3.2.1]-oct-3-yl)]carbonylmethyl-2-oxo-1H-1,4-benzodiazepin-3-yl]-N'-(3-methylphenyl)urea (0.300 g) as a colorless crystal.

mp: 159–172° C.; IR (KBr): 3353, 2945, 1663, 1611, 1555, 1489, 1450, 1234 1218 $cm^{-1}$; $^1$H-NMR ($CDCl_3$, δ): 1.56–1.68 (2H, m), 1.9–2.1 (2H, m), 2.26 (3H, s), 2.29 (3H, s), 2.96 (1H, d, J=13 Hz), 3.10–3.20 (2H, m), 3.30–3.50 (2H, m), 4.27 (0.5H, d, J=16 Hz), 4.43 (0.5H, d, J=16 Hz), 4.72 (0.5H, d, J=16 Hz), 4.90 (0.5H, d, J=16 Hz), 5.66 (1H, d, J=8 Hz), 6.81 (1H, d, J=6 Hz), 7.0–7.55 (12H, m), 7.80 (1H, m)

EXAMPLE 14

The following compound was obtained in a similar manner to that of Example 1.

N-[(3RS)-2,3-dihydro-5-(2-fluorophenyl)-1-(tetrahydrofuran-2-yl)methyl-2-oxo-1H-1,4-benzodiazepin-3-yl]-N'- (3-methylphenyl)urea mp: 215°–216° C. (dec.); IR (KBr): 3327, 1677, 1648, 1611, 1487 $cm^{-1}$; $^1$H-NMR (DMSO-$d_6$, δ): 1.09 (1H, m), 1.37 (2H, m), 1.48 (1H, m), 1.65 (1H, m), 2.24 (3H, s), 3.10 (1H, m), 3.70 (1H, t, J=12 Hz), 3.85 (1H, m), 4.30 (1H, m), 5.23 (1H, d, J=8 Hz), 6.74 (1H, d, J=8 Hz), 7.08–7.85 (12H, m), 9.00 (1H, m)

EXAMPLE 15

The following compound was obtained in a similar manner to that of Example 3.

N-[(3RS)-1-(benzimidazol-2-yl)methyl-2,3-dihydro-5-(2-fluorophenyl)-2-oxo-1H-1,4-benzodiazepin-3-yl]-N'-(3-methyl-phenyl)urea mp: 165°–167° C.; IR (KBr) 3371, 1685, 1611, 1551, 1487, 1449 $cm^{-1}$; $^1$H-NMR (DMSO-$d_6$, δ): 2.24 (3H, s), 5.31 (1H, d, J=17 Hz), 5.39 (1H, d, J=17 Hz), 5.43 (1H, d, J=9 Hz), 6.74 (1H, d, J=9 Hz), 7.00–8.00 (16H, m), 8.98 (1H, s), 12.49 (1H, s)

EXAMPLE 16-1

To a solution of (3RS)-3-amino-1-{2-(3-azabicyclo[3.2.2]-non-3-lyl)carbonyloxyethyl}-5-(2-fluorophenyl)-2,3-dihydro-1H-1,4-benzodiazepin-2-one (0.73 g) in THF (14 ml) was added 3-methylphenyl isocyanate (0.21 g) under stirring at ambient temperarture. The mixture was stirred for 0.5 hour under the same condition. The reaction mixture was evaporated in vacuo to afford an amorphous mass, which was triturated in diisopropyl ether to give a white crystalline powder. The collected powder was washed with diisopropyl ether and dried under reduced pressure to afford N-[(3RS)-1-{2-(3-azabicyclo[3.2.2]non-3-yl)carbonyloxyethyl}-5-(2-fluorophenyl)-2,3-dihydro-2-oxo-1H-1,4-benzodiazepin-3-yl]-N'-(3-methylphenyl)urea as a white powder (0.83 g).

mp: 169°–171° C.; IR (Nujol) 3345, 3280, 1683, 1652, 1610, 1552, 1485, 1375, 1268, 1215, 1207, 1121, 1004, 770 (si), 765; $^1$H-NMR ($CDCl_3$, δ): 1.3–1.8 (10H, m), 1.93 (1H, br s), 2.30 (3H, s), 2.96–3.68 (4H, m), 3.90–4.27 (31H, m), 4.68–4.80 (1H, m), 5.59 (1H, d, J=8 Hz), 6.84–7.77 (13H, m); Mass (m/z):598 ($M^+$+1)

EXAMPLE 16-2

The following compound was prepared in a similar manner to that of Example 16-1.

N-[(3RS)-1-[(3-azabicyclo[3.2.2]non-3-yl)carbonylmethyl]-2,3-dihydro-5-(2-fluorophenyl)-2-oxo-1H-1,4-benzodiazepin-3-yl]-N'-(cyclohexyl)urea mp: 128°–130° C.; IR (KBr) 3362, 2930, 2858, 1656, 1613, 1545, 1451, 1329, 1216, 1113, 1019, 758 $cm^{-1}$; $^1$H-NMR ($CDCl_3$, δ): 1.11–2.07 (20H, m), 3.43–3.92 (4H, m), 4.41 (1H, d,, J=16 Hz), 5.00 (1H, d, J=16 Hz), 5.59 (1H, d, J=8 Hz), 6.25 (1H, d, J=8 Hz), 6.99–7.80 (8H, m); Mass (m/z): 559 ($M^+$)

EXAMPLE 17

The following compound was obtained in a similar manner to that of Example 16.

N-[(3RS)-1-(1-adamantyloxycarbonylmethyl)-5-(2-fluorophenyl)-2,3-dihydro-2-oxo-1H-1,4-benzodiazepin-3-yl]-N'-(3-methylphenyl)urea mp: 187°–188.5° C.; IR (Nujol): 3320, 1714, 1678, 1642, 1610, 1560, 1375, 1210 (sh), 1195, 1050, 780, 764, 748 $cm^{-1}$; $^1$H-NMR (DMSO-$d_6$, δ): 1.57 (6H, br s), 2 00 (6H, br s), 2.07 (4H, br s), 2.24 (3H, s), 4.58 (2H, s), 5.30 (1H, d, J=8.5 Hz), 6.7–7.75 (13H, m), 8.94 (1H, s); Mass (m/z): 595 ($M^+$+1)

EXAMPLE 18-1

To a solution of N-[(3RS)-1-carboxymethyl-5-(2-fluorophenyl)-2,3-dihydro-2-oxo-1H-1,4-benzodiazepin-3-yl]-N'-(3-methylphenyl)urea (229 mg) and 1,3,3-trimethyl-6-azabicyclo-[3.2.1]octane (88.7 mg) in N,N-dimethylformamide (5 ml) were added successively 1-hydroxy-benzotriazole (74.3 mg), 1-ethyl-3-(3-diniethylaminopropyl)carbodiimide hydrochloride (105.4 mg) and triethylamine (55.7 mg) under stirring at ambient temperature. The mixture was stirred for 12 hours under the same condition. The reaction mixture was poured into water under stirring and adjusted to pH 8 with a saturated aqueous solution of sodium bicarbonate. The mixture was extracted with ethyl acetate twice and the combined organic extract was washed with water and brine successively and dried over magnesium sulfate. Removal of the solvent in vacuo gave a viscous oil, which was subjected to column chromatography on silica gel eluting with a mixture of chloroform and methanol (30:1). The fractions containing the desired compound were combined and evaporated in vacuo to afford an amorphous mass, which was pulverized in diisopropyl ether, collected by filtration and dried to afford N-[(3RS)-1-(1,3,3-trimethyl-6-azabicyclo[3.2.1]oct-6-yl)cabonylmethyl-5-(2-fluorophenyl)-2,3-dihydro-2-oxo-1H-1,4-benzodiazepin-3-yl]-N'-(3-methylphenyl)urea (0.29 g) as a crystalline powder.

mp: 194°–198° C.; IR (Nujol): 3350, 1685(sh), 1665(sh), 1650, 1605, 1550, 1486, 1373, 1320, 1305, 1205, 770, 748

$cm^{-1}$; $^1$H-NMR (DMSO-$d_6$, δ): 0.87–1.08 (9H, m), 1.2–2.0 (6H, m), 2.24 (3H, s), 2.9–3.0 (1H, m), 3.2–3.5 (2H, m), 4.25–4.75 (3H, m), 5.32 (1H, d, J=8.5 Hz), 6.74 (1H, d, J=6.6 Hz), 7.05–7.7 (12H, m), 8.96 (1H, s); Mass (m/z): 596 ($M^+$+1)

EXAMPLE 18-2

The following compound was obtained in a similar manner to that of Example 18-1.

N-[(3RS)-1-(2-azabicyclo[2.2.1]hept-5-en-2-yl) carbonylmethyl-5-(2-fluorophenyl)-2,3-dihydro-2-oxo-1H-1,4-benzodiazepin-3-yl]-N'-(3-methylphenyl)urea mp: 153°–155° C. (dec.); IR (Nujol): 3300, 1690, 1670, 1635, 1615 (sh), 1560, 1505, 1374, 1325, 1230, 1195, 765, 720 $cm^{-1}$; $^1$H-NMR (DMSO-$d_6$, δ): 1.51 (1H, br s), 1.61 (1H, br s), 2.24 (3H, s), 2.55–2.9 (2H, m), 3.15–3.3 (1H, m), 3.55–3.65 (1H, m), 4.4–5.0 (2H, m), 5.30 (1H, d, J=7.9 Hz), 6.3–6.5 (2H, m), 6.75 (1H, d, J=6.6 Hz), 7.1–7.7 (12H, m), 8.94 (1H, br s); Mass (m/z): 538 ($M^+$+1)

EXAMPLE 18-3

The following compound was obtained in a similar manner to that of

EXAMPLE 18-1.

N-[(3RS)-1-(2-azabicyclo[2.2.1]hept-2-yl) carbonylmethyl-5-(2-fluorophenyl)-2,3-dihydro-2-oxo-1H-1,4-benzodiazepin-3-yl]-N'- (3-methylphenyl)urea mp: 168°–171° C.; IR (Nujol): 3300, 1694, 1677, 1637, 1620, 1594, 1568, 1506, 1480, 1370, 1330, 1235, 770, 755 $cm^{-1}$; $^1$H-NMR (DMSO-$d_6$, δ): 1.3–1.8 (6H, m), 2.24 (3H, s), 2.95–3.5 (3H, m), 4.35–4.75 (3H, m), 5.31 (1H, d, J=8.3 Hz ), 6.75 (1H, d, J=6.5 Hz), J=6.5 Hz), 7.05–7.8 (12H, m), 8.96 (1H, br s); Mass (m/z): 540 ($M^+$+1)

EXAMPLE 18-1

The following compound was obtained in a similar manner to that of Example 18-1.

N-[(3RS)-1-(5-benzyl-2,5-diazabicyclo[2.2.1]hept-2-yl) carbonylmethyl-5-(2-fluorophenyl)-2,3-dihydro-2-oxo-1H-benzodiazepin-3-yl]-N'-(3-methylphenyl)urea mp: 152°–154° C. (dec.); IR (Nujol) 3300, 1685 (sh), 1670 (sh), 1650, 1605, 1545, 1481, 1373, 1322, 1205, 770, 750, 725, 690 $cm^{-1}$; $^1$H-NMR (DMSO-$d_6$, δ): 1.55–2.0 (2H, m), 2.42 (3H, s), 2.75–2.9 (1H, m), 3.1–3.25 (1H, m), 3.4–3.6 (2H, m), 3.65–3.8 (2H, m), 4.5–4.8 (2H, m), 5.32 (1H, d, J=8.5 Hz), 6.75 (1H, d, J=6.5 Hz), 7.05–7.7 (17 Hz, m), 9.98 (1H, br s); Mass (m/z): 631 ($M^+$+1)

EXAMPLE 19

To a solution of (3R)-3-amino-1-{(3-azabicyclo[3.2.2] non-3-yl)carbonylmethyl}-2,3-dihydro-5-(2-fluorophenyl)-1H-1,4-benzodiazepin-2-one (5.80 g) in tetrahydrofuran (50 ml) was added dropwise a solution of 3-methylphenyl isocyanate (1.96 g) in tetrahydrofuran (10 ml) under stirring at ambient temperature. The mixture was stirred overnight at ambient temperature. The resultant mixture was concentrated in vacuo to give a crude product.

The crude product was purified by flash chromatography on silica gel (eluent: ethyl acetate:n-hexane=1:1) to afford N-[(3R)-1-{(3-azabicyclo[3.2.2]non-3-yl)carbonylmethyl}-2,3-dihydro-5-(2-fluorophenyl)-2-oxo-1H-1,4-benzodiazepin-3-yl]-N'-(3-methylphenyl)urea, which was triturated with diisopropyl ether to give a colorless solid (7.40 g).

mp: 156.0° C.; IR (KBr): 3360, 2933, 2864, 1657, 1612, 1553, 1489, 1451, 1388, 1328, 1215 $cm^{-1}$; $^1$H-NMR (DMSO-$d_6$, δ): 1.40–1.85 (8H, m), 1.95–2.15 (2H, m), 2.24 (3H, s), 3.40–3.55 (2H, m), 3.55–3.80 (2H, m), 4.71 (1H, d, J=16 Hz), 5.01 (1H, d, H=16 Hz), 5.33 (1H, d, J=10 Hz), 6.75 (1H, d, J=10 Hz), 7.00–7.80 (12H, m), 8.97 (1H, s); Mass (m/z): 568 ($M^+$+1)

EXAMPLE 20

The following compound was obtained in a similar manner to that of Example 22. Purification was performed by flash chromatography on silica gel (eluent: chloroform).

N-[(3S)-1-{(3-azabicyclo[3.2.2]non-3-yl) carbonylmethyl}-2,3-dihydro-5-(2-fluorophenyl)-2-oxo-1H-1,4-benzodiazepin-3-yl]-N'-(3-metbylphenyl)urea mp: 146°–147° C.; IR (KBr): 3357, 2933, 2864, 1658, 1611, 1553, 1489, 1451, 1329, 1215 $cm^{-1}$; $^1$H-NMR (DMSO-$d_6$, δ): 1.40–1.85 (8H, m), 1.95–2.15 (2H, m), 2.24 (3H, s), 3.40–3.55 (2H, m), 3.55–3.80 (2H, m), 4.71 (1H, d, J=16 Hz), 5.01 (1H, d, H=16 Hz), 5.33 (1H, d, J=10 Hz), 6.75 (1H, d, J=10 Hz), 7.00–7.80 (12H, m), 8.97 (1H, s); Mass (m/z): 568 ($M^+$+1)

EXAMPLE 21

The following compound was obtained in a similar manner to that of Example 18-1.

N-[(3RS)-1-{(3-azabicyclo[3.2.2]non-3-yl) carbonylmethyl}-2,3-dihydro-5-phenyl-2-oxo-1H-1,4-benzodiazepin-3-yl]-N'-(3-methylphenyl)urea mp: 165–170° C. (dec.); IR (Nujol, $cm^{-1}$): 3350, 3200 (sh), 1695, 1665, 1638, 1615, 1592, 1564, 1507, 1480, 1372, 1325, 1267, 1235, 1194, 1020, 766, 720, 698; $^1$H-NMR (DMSO-$d_6$, δ): 1.45–1.8 (8H, br m), 1.9–2.1 (2H, br s), 2.24 (3H, s), 3.44–3.67 (4H, m), 4.89 (2H, ABq, J=16.9 Hz, 29.4 Hz), 5.32 (1H, d, J=8.5 Hz), 6.74 (1H, d, J=6.7 Hz), 7.05–7.72 (13H, m), 8.97 (1H, s); LC/MS (m/z): 550 ($M^{+1}$)

EXAMPLE 22

To a suspension of (3RS)-3-amino-1-[(2-azatricyclo-[4.3.1.1$^{4,8}$]undec-2-yl)carbonylmethyl]-2,3-dihydro-5-(2-fluorophenyl)-1H-1,4-benzodiazepin-2-one (0.265 g) in dichloromethane (5 ml) was added dropwise a solution m-tolyl isocyanate (0.101 g) in dichloromethane (3 ml) under stirring. The mixture was stirred at room temperature overnight. The resultant mixture was concentrated in vacuo to afford a crude product. The crude product was purified by column chromatography on silica gel with a mixture of chloroform and methanol (100:1) as an eluent to afford N-[(3RS)-1-(2-azatricyclo[4.3.1.1$^{4,8}$]undec-2-yl)-carbonylmethyl-2,3-dihydro-5-(2-fluorophenyl)-2-oxo-1H-1,4-benzo-diazepin-3-yl]-N'-(3-methylphenyl)urea as a colorless crystalline solid (0.248 g).

mp: 134°–138° C. IR (KBr): 3373, 2910, 1655, 1612, 1553, 1489, 1450, 1217 $cm^{-1}$; $^1$H NMR (DMSO-$d_6$, δ): 1.40–2.00 (12H, m), 2.27 (3H, s), 4.72 (1H, m), 4.88 (1H, m), 5.34 (1H, m), 6.76 (1H, m), 7.11–7.70 (12H, m), 8.95 (1H, d, J=10 Hz); Mass (m/z): 593 ($M^+$)

EXAMPLE 23

A mixture of N-[(3RS)-2,3-dihydro-5-(2-fluorophenyl)-1-hyldroxycarbonylmethyl-2-oxo-1H-1,4-benzodiazepin-3-yl]-N'-(3-methylphenyl)urea (0.301 g), dicyclohexyl carbodiimide (0.163 g) and 1-hydroxy-1H-benzotriazole monohydrate (0.122 g) in tetrahydrofuran was stirred for 2 hours at ambient temperature. To the mixture was added gradually a suspension of 2-aminoadamantane (0.123 g) in tetrahydrofuran and the reaction mixture was stirred at ambient temperature overnight. The resultant mixture was concentrated in vacuo. The residue was purified by column chromatography on silica gel with a mixture of chloroform and methanol (50:1) to give N-[(3RS)-1-(2-adamantylaminocarbonylmethyl)-2,3-dihydro-5-(2-fluorophenyl)-2-oxo-1H-1,4-benzo -diazepin-3-yl]-N'-(3-methylphenyl)urea (0.396 g).

mp: 245°–246 ° C.; IR (KBr): 3301, 2906, 1693, 1669, 1636, 1541, 1489 $cm^{-1}$; $^1H$ NMR (DMSO-$d_6$, δ): 1.46–2.05 (14H, m), 2.25 (3H, s), 3.85 (1H, m), 4.49 (1H, d, J=19 Hz), 4.66 (1H, d, J=19 Hz), 5.30 (1H, d, J=8 Hz), 6.73 (1H, d, J=8 Hz), 7.08–7.68 (12H, m), 8.04 (1H, d, J=8 Hz), 8.97 (1H, s); Mass (m/z): 594 ($M^+$)

EXAMPLE 24

To a solution of (3RS)-3-amino-2,3-dihydro-5-(2-fluorophenyl)-1-(3-methylpyridin-2-yl)methyl-1H-1,4-benzodiazepin-2-one (0.87 g) in tetrahydrofuran (20 ml) was added dropwise a solution of m-tolyl isocyanate (0.355 g) in tetrahydrofuran (5 ml) at ambient temperature and stirred overnight.

The mixture was concentrated in vacuo and purified by flash column chromatography on silica gel with a mixture of chloroform and methanol as an eluent. The desired fractions were combined and concentrated in vacuo. The residue was triturated by isopropyl ether and collected by suction to give N-[(3RS)-2,3-dihydro-5-(2-fluorophenyl)-1-(3-methylpyridin-2-yl)methyl-2-oxo-1H-1,4-benzodiazepin-3-yl]-N'-(3-methylphenyl)urea (0.42 g).

mp: 216°–217°C.; IR (KBr): 3351, 3058, 1678, 1649, 1611, 1556, 1489, 1450 $cm^{-1}$; $^1H$ NMR (DMSO-$d_6$, δ): 2.25 (3H, s), 2.30 (3H, s), 5.23 (1H, d, J=16 Hz), 5.35 (1H, d, J=16 Hz), 5.37 (1H, d, J=8 Hz), 6.75 (1H, d, J=8 Hz), 7.00–7.80 (14H, m), 8.17 (1H, m), 9.00 (1H, s); Mass (m/z): 507 ($M^+$)

EXAMPLE 25

The following compound was prepared in a similar manner to that of Example 22.

N-[(3RS)-1-(benzothiophen-3-yl)methyl-2,3-dihydro-5-(2-fluorophenyl)-2-oxo-1H-1,4-benzodiazepin-3-yl]-N'-(3-methylphenyl)urea mp: 214°–216° C.; IR (KBr): 3341, 1679, 1644, 1613, 1562, 1486, 1449, 1210, 770 $cm^{-1}$; $^1H$ NMR (DMSO-$d_6$, δ): 2.25 (3H, s), 5.30 (1H, d, 18 Hz), 5.37 (1H, d, J=6 Hz), 5.78 (1H, d, J=18 Hz), 6.72–7.92 (18H, m), 8.98 (1H, s) Mass (m/z): 548 ($M^+$)

EXAMPLE 26

The following compound was prepared in a similar manner to that of Example 22.

N-[(3RS)-2,3-dihydro-5-(2-fluorophenyl)-1-(4-methoxypyridin-2-yl)methyl-2-oxo-1H-1,4-benzodiazepin-3-yl]-N'-(3-methylphenyl)urea mp: 195°–200° C.; IR (KBr): 3318, 1678, 1648, 1599, 1561, 1486, 1450, 1307, 1217 $cm^{-1}$; $^1H$ NMR (DMSO-$d_6$, δ): 2.25 (3H, s), 3.70 (3H, s), 5.16 (1H, d, J=16 Hz), 5.33 (1H, d, J=16 Hz), 5.38 (1H, d, J=7 Hz), 6.72–7.76 (15H, m), 8.23 (1H, d, J=7 Hz), 8.98 (1H, s); Mass (m/z): 523 ($M^+$)

EXAMPLE 27

To a solution of (3RS)-3-amino-1-(4-chloropyridin-2-yl) -methyl-2,3-dihydro-5-(2-fluorophenyl)-1H-1,4-benzodiazepin-2-one (0.117 g) in dichloromethane (8 ml) was added dropwise a solution of m-tolyl isocyanate (0.049 g) in dichloromethane (2 ml). The mixture was stirred at ambient temperature overnight. The resultant precipitates were collected by suction and washed with isopropyl ether to give N-[(3RS)-1-(4-chloropyridin-2-yl)methyl-2,3-dihydro-5-(2-fluorophenyl)-2-oxo-1H-1,4-benzodiazepin-3-yl]-N'-(3-methylphenyl)urea as a colorless crystalline solid (100 mg).

mp: 227°–228° C.; IR (KBr): 3314, 1679, 1644, 1612, 1559, 1487, 1450, 1215 $cm^{-1}$; $^1H$ NMR (DMSO-$d_6$, δ): 2.25 (3H, s), 5.21 (1H, s), 5.40 (2H, dd, J=4 Hz, J=16 Hz), 6.76 (1H, d, J=6 Hz), 7.09–7.76 (14H, m), 8.38 (1H, d, J=4 Hz), 8.98 (1H, s); Mass (m/z): 527 ($M^+$)

EXAMPLE 28

The following compound was prepared in a similar manner to that of Example 22.

N-[(3RS)-1-(benzofuran-2-yl)methyl-2,3-dihydro-5-(2-fluorophenyl)-2-oxo-1H-1,4-benzodiazepin-3-yl]-N'-(3-methylphenyl)urea mp: 213°–214° C.; IR (KBr): 3335, 1682, 1645, 1562, 1451, 1213, 750 $cm^{-1}$; H NMR (DMSO-$d_6$, δ): 2.25 (3H, s), 5.28 (1H, d, J=16 Hz), 5.38 (1H, d, J=8 Hz), 5.65 (1H, d, J=16 Hz), 6.72 (1H, s), 6.75 (1H, d, J=8 Hz), 7.09–7.91 (16H, m), 9.04 (1H, s) Mass (m/z): 532 ($M^+$)

EXAMPLE 29

The following compound was prepared in a similar manner to that of Example 26.

N-[(3RS)-1-(2-acetylthiophen-3-yl)methyl-2,3-dihydro-5-(2-fluorophenyl)-2-oxo-1H-1,4-benzodiazepin-3-yl]-N'-(3-methylphenyl)urea mp: 222°–223° C.; IR (KBr): 3314, 1675, 1647, 1612, 1559, 1487, 1449, 1415, 1214 $cm^{-1}$; $^1H$ NMR (DMSO-$d_6$, δ): 2.24 (3H, s), 3.32 (3H, s), 5.37 (1H, d, J=8 Hz), 5.47 (2H, dd, J=8 Hz), 16 Hz), 6.74 (1H, m), 6.85 (1H, d, J=4 Hz), 7.08–7.78 (14H, m), 8.98 (1H, s); Mass (m/z): 540 ($M^+$)

EXAMPLE 30

The following compound was prepared in a similar manner to that of Example 26.

N-[(3RS)-2,3-dihydro-5-(2-fluorophenyl)-1-(oxypyridin-2-yl)methyl-2-oxo-1H-1 ,4-benzodiazepin-3-yl] -N, -(3-methylphenyl)urea mp:241°–243° C.; IR (KBr): 3306, 1677, 1643, 1614, 1490, 1438, 1218, 763 $cm^{-1}$; $^1H$ NMR (DMSO-$d_6$, δ): 2.25 (3H, s), 5.28 (2H, s), 5.46 (1H, d, J=8 Hz), 6.75 (1H, d, J=8 Hz), 7.14–7.67 (15H, m), 8.29 (1H, d, J=6 Hz), 8.97 (1H, s); Mass (m/z): 509 ($M^+$) 216

EXAMPLE 31

The following compound was prepared in a similar manner to that of Example 26.

N-[(3RS)-2,3-dihydro-5-(2-fluorophenyl)-1-[3-(1-pyrrolidinylcarbonyl)pyridin-2-yl]methyl-2-oxo-1H-1,4-benzodiazepin-3-yl]-N'-(3-methylphenyl)urea mp: 153°–155° C.; IR (KBr): 3349, 1681, 1612, 1556, 1488, 1450, 1216, 755 $cm^{-1}$; $^1H$ NMR (DMSO-$d_6$, δ): 1.72–1-90 (4H, m), 2.19 (3H, s), 3.00–3.50 (4H, m), 5.08 (1H, d, J=16 Hz), 5.22 (1H, d, J=16 Hz), 5.34 (1H, d, J=8 Hz), 6.69 (1H, d, J=8 Hz), 7.04–7.74 (14H, m), 8.29 (1H, d, J=6 Hz), 8.94(1H, s); Mass : (m/z): 590 ($M^+$)

EXAMPLE 32

The following compound was prepared in a similar manner to that of Example 24.

N-[(3RS)-2,3-dihydro-1-(4-methylpyridin-2-yl)methyl-2-oxo-5-phenyl-1H-1,4-benzodiazepin-3-yl]-N'-(3-methylphenyl)urea mp: 212°–213° C.; IR (KBr): 3325, 3080, 2919, 1679, 1650, 1608, 1558, 1489, 1448 $cm^{-1}$; $^1H$ NMR ($CDCl_3$, δ): 2.02 (3H, s), 2.25 (3H, s), 5.10 (1H, d, J=16 Hz), 5.39 (1H, d, J=8 Hz), 5.48 (1H, d, J=16 Hz), 6.75 (1H, d, J=8 Hz), 6.80–8.30 (16H, m), 9.00 (1H, s); Mass (m/z): 489 ($M^+$)

EXAMPLE 33

The following compound was prepared in a similar manner to that of Example 24.

N-[(3RS)-2,3-dihydro-1-(isoquinolin-1-yl)methyl-2-oxo-5-phenyl-1H-1,4-benzodiazepin-3-yl]-N'-(3-methylphenyl) urea mp: 218°–221°C.; IR (KBr): 3335, 3054, 1676, 1650, 1611, 1559, 1490, 1448, $cm^{-1}$; $^1H$ NMR (DMSO-$d_6$, δ): 2.24 (3H, s), 5.44 (1H, d, J=8 Hz), 5.68 (1H, d, J=16 Hz), 6.05 (1H, d, J=16 Hz), 6.75 (1H, d, J=8 Hz), 7.00–8.30 (19H, m), 9.01 (1H, s); Mass (m/z): 525 ($M^+$)

EXAMPLE 34

To a solution of (3Rs)-3-amino-5-cyclohexyl-2,3-dihydro-1-(pyridin-2-yl)methyl-1H-1,4-benzodiazepin-2-one (0.120 g) in dichloromethane (5 ml) was added dropwise a solution m-tolyl isocyanate (49 mg) in dichloromethane (1 ml) at ambient temperature, and stirred overnight. The resultant mixture was concentrated in vacuo and purified by column chromatography on silica gel with chloroform to give a crude product as a colorless form, which was triturated with isopropyl ether and collected by suction to give N-[(3RS)-5-cyclohexy-2,3-dihydro-2-oxo-1-(pyridin-2-yl) methyl-1H-1,4-benzodiazepin-3-yl]-N'-(3-methylphenyl) urea (0.08 g).

mp: 157°–163° C.; IR (KBr): 3334, 2928, 2852, 1678, 1652, 1613, 1596, 1558, 1490, 1448 $cm^{-1}$; $^1H$ NMR (DMSO-$d_6$, δ): 0.60–2.00 (10H, m), 2.19 (3H, s), 2.80 (1H, m), 5.02 (1H, d, J=16 Hz), 5.10 (1H, d, J=7 Hz), 5.28 (1H, d, J=16 Hz), 6.65 (1H, d, J=7 Hz), 7.00–7.80 (11H, m), 8.35 (1H, m), 8.82 (1H, s); Mass (m/z): 481 ($M^+$)

EXAMPLE 35

To a solution of (3RS)-3-amino-2,3-dihydro-5-(2-fluorophenyl)-1-(4-methylpyridin-2-yl)methyl-1H-1,4-benzodiazepin-2-one (0.57 g) in dichloromethane (5 ml) was added dropwise a solution of m-tolyl isocyanate (0.214 g) in dichloromethane (1 ml) at ambient temperature. The mixture was stirred overnight under the same condition. The resultant mixture was concentrated in vacuo to afford a crude product. The crude product was purified by column chromatography on silica gel with an eluent of a mixture of chloroform and methanol (100:1) to afford N-[(3RS)-2,3-dihydro-5-(2-fluorophenyl)-1-(4-methylpyridin-2-yl)-methyl-2-oxo-1H-1,4-benzodiazepin-3-yl]-N'-(3-methylphenyl)urea (0.360 g) as a colorless crystalline solid.

mp: 181°–183° C.; IR (KBr): 3319, 3086, 1686, 1646, 1612, 1559, 1486, 1449, 1380, 1326, 1297, 1216, 1163, 1121, 1032, 1009 $cm^{-1}$; $^1H$ NMR (DMSO-$d_6$, δ): 2.16 (3H, s), 2.28 (3H, s), 5.25 (1H, d, J=16 Hz), 5.36 (1H, d, J=9 Hz), 5.52 (1H, d, J=16 Hz), 6.69 (1H, d, J=9 Hz), 7.00–7.80 (14H, m), 8.56 (1H, d, J=6 Hz), 8.90 (1H, s)

EXAMPLE 36-1

The following compound was prepared in a similar manner to that of Example 35

N-[(3RS)-2,3-dihydro-5-(2-fluorophenyl)-1-(3-methoxycarbonylpyridin-2-yl)methyl-2-oxo-1H-1,4-benzodiazepin-3-yl]-N'-(3-methylphenyl)urea mp: 171°–175° C.; IR (KBr): 3313, 3084, 2586, 1735, 1687, 1646, 1612, 1562, 1492, 1450, 1380, 1299, 1218 $cm^{-1}$; NMR (DMSO-$d_6$, δ): 2.18 (3H, s), 3.84 (3H, s), 5.34 (1H, d, J=9 Hz), 5.53 (1H, d, J=16 Hz), 5.56 (1H, d, J=16 Hz), 6.70 (1H, d, J=9 Hz), 7.00–7.70 (13H, m), 8.21 (1H, d, J=9 Hz), 8.42 (1H, d, J=7 Hz), 8.96 (1H, s); Mass (m/z) (free): 551 ($M^+$)

EXAMPLE 36-2

To a solution of N-[(3RS)-2,3-dihydro-5-(2-fluorophenyl)-1-(3-methoxycarbonylpyridin-2-yl)methyl-2-oxo-1H-1,4-benzodiazepin-3-yl]-N'-(3-methylphenyl)urea (0.35 g) in 1,4-dioxane (13 ml) was added an aqueous solution of potassium hydroxide (0.35 g in 5 ml of water) at room temperature and the mixture was stirred overnight at ambient temperature. The resultant mixture was concentrated in vacuo and the residue was taken up with 10 ml water and washed with isopropyl ether. The aqueous layer was adjusted to pH 7.0 with 10% citric acid aqueous solution and extracted with chloroform. The organic layer was dried over sodium sulfate, filtered and concentrarted in vacuo. The crude compound was purified by column chromatography on silica gel with a mixture of chloroform and methanol to give N-[(3RS)-2,3-dihydro-5-(2-fluorophenyl)-1-(3-hydroxycarbonyl-pyridin-2-yl)methyl-2-oxo-1H-1,4-benzodiazepin-3-yl]-N'-(3-methylphenyl)urea as a yellow form, which was triturated by isopropyl ether and collected by suction (0.08 g).

mp: 227° C.; IR (KBr): 3400, 3205, 3064, 3041, 1704, 1641, 1596, 1578, 1557, 1489, 1456, 1382, 1274, 1257, 1223 $cm^{-1}$; NMR (DMSO-$d_6$, δ): 2.30 (3H, s), 5.88 (1H, d, J=16 Hz), 6.02 (1H, d, J=16 Hz), 6.56 (1H, d, J=9 Hz), 6.84 (1H, d, J=9 Hz), 7.00–8.60 (15H, m), 9.79 (1H, br), 10.98 (1H, s)

EXAMPLE 37

The following compound was prepared in a similar manner to that of Example 35.

N-[(3RS)-1-(3-aminocarbonylpyridin-2-yl)methyl-2,3-dihydro-5-(2-fluorophenyl)-2-oxo-1H-1,4-benzodiazepin-3-yl]-N'-(3-methylphenyl)urea mp: 203° C.; IR (KBr): 3296, 1673, 1643, 1610, 1557, 1487, 1445, 1385, 1321, 1217 $cm^{-1}$; NMR (DMSO-$d_6$, δ): 2.24 (3H, s), 5.37 (1H, d, J=9 Hz), 5.46 (2H, br), 6.74 (1H, d, J=9 Hz), 7.00–7.65 (13H, m), 7.72 (1H, br), 7.91 (1H, d, J=9 Hz), 8.10 (1H, br), 8.34 (1H, d, J=7 Hz), 9.01 (1H, s); Mass (m/z): 536($M^+$)

EXAMPLE 38

The following compound was prepared in a similar manner to that of Example 35.

N-[(3RS)-2,3-dihydro-1-{3-(2-dimethylaminoethylamino-carbonyl)pyridin-2-yl}methyl-5-(2-fluorophenyl)-2-oxo-1-H-1,4-benzodiazepin-3-yl]-N'-(3-methylphenyl)urea mp: 135°–136° C.; IR(KBr): 3339, 3086, 2955, 2882, 2836, 2786, 1660, 1613, 1557, 1489, 1449, 1387, 1325, 1305, 1214, 1160 $cm^{-1}$; $^1H$ NMR (DMSO-$d_6$, δ): 2.14 (6H, s), 2.18 (3H, s), 2.40 (1H, m), 5.30 (1H, d, J=9 Hz), 5.38 (2H, br s), 6.68 (1H, d, J=9 Hz), 7.00–7.60 (12H, m), 7.73 (1H, d, J=9 Hz), 8.27 (1H, d, J=7 Hz), 8.50 (1H, m), 8.92 (1H, s); Mass (m/z): 607 ($M^+$)

EXAMPLE 39

The following compound was prepared in a similar manner to that of Example 35.

N-[(3RS)-1-(4-tert-butylpyridin-2-yl)methyl-2,3-dihydro-5-(2-fluorophenyl)-2-oxo-1H-1,4-benzodiazepin-3-yl]-N'-(3-methylphenyl)urea mp: 142°–144° C.; IR (KBr): 3277, 3065, 2969, 2595, 1685, 1612, 1557, 1510, 1487, 1451, 1380, 1296, 1215 $cm^{-1}$; $^1H$ NHR (DMSO-$d_6$, δ): 1.11 (9H, s), 2.20 (3H, s), 5.26 (1H, d, J=16 Hz), 5.35 (1H, d, J=9 Hz), 5.47 (1H, d, J=16 Hz), 6.68 (1H, d, J=9 Hz), 7.00–7.80 (14H, m), 8.46 (1H, d, J=7 Hz), 8.94 (1H, s); Mass (m/z) (free) 549 ($M^+$)

EXAMPLE 40

The following compound was prepared in a similar manner to that of Example 35.

N-[(3RS)-2,3-dihydro-5-(2-fluorophenyl)-1-(isoquinolin-1-yl)methyl-2-oxo-1H-1,4-benzodiazepin-3-yl]-N'-(3-methylphenyl)urea mp: 145°–147° C.; IR (KBr): 3381, 3073, 3033, 2681, 2617, 2341, 1990, 1686, 1644, 1612, 1558, 1491, 1451, 1328, 1216 $cm^{-1}$; $^1H$ NMR (DMSO-$d_6$, δ): 2.18 (3H, s), 5.42 (1H, d, J=9 Hz), 5.88 (1H, d, J=16 Hz), 6.02 (1H, d, J=16 Hz), 6.68 (1H, d, J=9 Hz), 7.00–8.40 (18H, m), 9.02 (1H, s); Mass (m/z): 543 ($M^+$)

EXAMPLE 41

The following compound was prepared in a similar manner to that of Example 35.

N-[(3RS)-2,3-dihydro-5-(2-fluorophenyl)-2-oxo-1-(5,6,7,8-tetrahydroisoquinolin-1-yl)methyl-1H-1,4-benzodiazepin-3-yl]-N'-(3-methylphenyl)urea mp: 207°–210° C.; IR (KBr): 3359, 3269, 3048, 2936, 1676, 1648, 1612, 1560, 1487, 1450, 1383, 1328, 1294, 1214 $cm^{-1}$; $^1H$ NMR(DMSO-$d_6$, δ): 1.40–1.80 (4H, m), 2.20 (3H, s), 2.40–2.80 (4H, m), 5.10 (1H, d, J=16 Hz), 5.24 (1H, d, J=16 Hz), 5.30 (1H, d, J=9 Hz), 6.68 (1H, d, J=9 Hz), 6.86 (1H, d, J=5 Hz), 7.00–7.60 (11H, m), 7.92 (1H, d, J=5 Hz), 8.28(1H,s), 8.94 (1H, s); Mass (m/z) 547 ($M^+$)

EXAMPLE 42

The following compound was prepared in a similar manner to that of Example 35.

N-[(3RS)-2,3-dihydro-5-(2-fluorophenyl)-2-oxo-1-(3-methylcarbonylpyridin-2-yl)methyl-1H-1,4-benzodiazepin-3-yl]-N'-(3-methylphenyl)urea mp: 218°–222° C.; IR (KBr): 3328, 3068, 3036, 2544, 2340, 1687, 1611, 1558, 1490, 1450, 1360, 1326, 1253, 1215 cm-⁻; $^1H$ NMR (DMSO-$d_6$, δ): 2.18 (3H, s), 2.60 (3H, s), 5.33 (1H, d, J=9 Hz), 5.41 (2H, m), 6.68 (1H, d, J=9 Hz), 7.00–7.60 (13H, m), 8.29 (1H, m), 8.37 (1H, d, J=9 Hz), 8.99 (1H, s); Mass (m/z) (free) 535 ($M^+$)

EXAMPLE 43

The following compound was prepared in a similar manner to that of Example 27.

N-(3RS)-2,3-dihydro-5-(2-fluorophenyl)-2-oxo-1-{2-(pyridin-3-yl)carbonylaminoethyl}-1H-1,4-benzodiazepin-3-yl]-N'-(3-methylphenyl)urea mp: 237°–240° C.; IR (KBr): 3261, 1678, 1645, 1613, 1557, 1492, 1451, 1217, 1203 $cm^{-1}$; $^1H$ NMR (DMSO-$d_6$, δ): 2.24 (3H, s), 3.20–3.50 (1H, br), 3.60 (1H, t, J=7 Hz), 3.99–4.06 (1H, m), 4.30–4.37 (1H, m), 5.28 (1H, d, J=8 Hz), 6.75 (1H, d, J=7 Hz), 7.10–7.36 (7H, m), 7.47–7.56 (4H, m), 7.73 (1H, t, J=8 Hz), 7.83 (1H, d, J=8 Hz), 8.10–8.13 (1H, m), 8.69 (1H, d, J=3 Hz), 8.82 (1H, m), 8.94 (1H, s), 9.00 (1H, s); Mass (m/e): 550 ($M^+$)

EXAMPLE 44

The following compound was prepared in a similar manner to that of Example 27.

N-[(3RS)-1-(5-acetylfuran-2-yl)methyl-2,3-dihydro-5-(2-fluorophenyl)-2-oxo-1H-1,4-benzodiazepin-3-yl]-N'-(3-methylphenyl)urea mp: 234°–235° C.;

IR (KBr): 3305, 1678, 1644, 1614, 1562, 1520, 1489, 1451, 1216 $cm^{-1}$; $^1H$ NMR (DMSO-$d_6$, δ): 2.19 (3H, s), 2.24 (3H, s), 5.18 (1H, d, J=16 Hz), 5.34 (1H, d, J=8 Hz), 5.54 (1H, d, J=16 Hz), 6.41 (1H, d, J=4 Hz), 7.75 (1H, d, J=8 Hz), 7.10–7.40 (9H, m), 7.45 (1H, m), 7.54 (1H, m), 7.69 (1H, m), 7.84 (1H, d, J=8 Hz), 9.00 (1H, s); Mass (m/z): 524 ($M^+$)

EXAMPLE 45

A solution of 3-methylphenyl isocyanate (0.113 g) in methylene chloride (3 ml) was added dropwise to a solution of (3RS)-1-(2-acetylthiophen-3-yl)methyl-3-amino-5-cyclohexyl-2,3-dihydro-1H-1,4-benzodiazepin-2-one (0.252 g) in methylene chloride (8 ml) under stirring. The mixture was stirred overnight at ambient temperature.

The resultant precipitate was collected by filtration and washed with isopropyl ether to afford N-[(3RS)-1-(2-acetylthiophen-3-yl)methyl-5-cyclohexyl-2,3-dihydro-2-oxo-1H-1,4-benzodiazepin-3-yl]-N'-(3-methylphenyl)urea (0.160 g).

mp: 231°–232° C.; IR (KBr): 3329, 2927, 2852, 1661, 1613, 1558, 1490, 1447, 1415, 1216 $cm^{-1}$; $^1H$ NMR (DMSO-$d_6$, δ): 0.90–0.95 (1H, m), 1.05–2.00 (9H, m), 2.23 (3H, s), 2.51 (3H, s), 2.92 (1H, m), 5.17 (1H, d, J=8 Hz), 5.29 (1H, d, 17 Hz), 5.46 (1H, d, J=17 Hz), 5.76 (1H, s), 6.73 (1H, d, J=7 Hz), 6.85 (1H, d, J=5 Hz), 7.05–7.80 (9H, m), 7.82 (1H, d, J=5 Hz), 8.89 (1H, s); Mass (m/z): 528 ($M^+$)

EXAMPLE 46

The following compound was prepared in a similar manner to that of Example 45.

N-[(3RS)-1-(3-acetylpyridin-2-yl)methyl-5-cyclohexyl-2,3-dihydro-2-oxo-1H-1,4-benzodiazepin-3-yl]-N'-(3-methylphenyl)urea mp 241°–243° C.;

IR (KBr): 3322, 2925, 1683, 1647, 1613, 1561, 1491, 1445, 1220 $cm^{-1}$; $^1H$ NMR (DMSO-$d_6$, δ): 0.95–1.60 (6H, m), 1.65 (2H, m), 1.79 (1H, m), 1.94 (1H, m), 2.22 (3H, s), 2.64 (3H, s), 2.94 (1H, m), 5.16 (1H, d, J=8 Hz), 5.27 (1H, d, J=18 Hz), 5.40 (1H, d, J=18 Hz), 6.72 (1H, d, J=6 Hz), 7.06–7.36 (8H, m), 7.75 (1H, m), 8.32 (1H, m), 8.52 (1H, m), 8.87 (1H, s); Mass (m/z): 524 ($M^{+1}$)

EXAMPLE 47-1

To a solution of (3RS)-3-amino-1-[(3-azabicyclo[3.2.2]non-3-yl)carbonylmethyl]-5-cyclohexyl-2,3-dihydro-1H-1,4-benzodiazepin-2-one (0.19 g) in dichloromethane (10 ml) was added m-tolyl isocyanate (0.064 g) at room temperature. The mixture was stirred at ambient temperature overnight. The reaction mixture was concentrated in vacuo. The residue was subjected by column chromatography on silica gel with chloroform and a mixture of chloroform and ethyl acetate (5:1) to give N-[(3RS)-1-[(3-azabicyclo[3.2.2]non-3-yl) carbonylmethyl]-5-cyclohexyl-2,3-dihydro-2-oxo-1H-1,4-benzodiazepin-3-yl]-N'-(3-methylphenyl)urea (0.075 g) as a white amorphous mass.

mp: 133°–135° C.; IR (KBr): 3350, 2925, 2843, 1646, 1610, 1600, 1542, 1480, 1440, 1200, 790 $cm^{-1}$; $^1H$ NMR (DMSO-$d_6$, δ): 1.00–2.10 (20H, m), 2.22 (3H, s), 2.91 (1H, t, J=8 Hz), 3.40–3.80 (4H, m), 4.55 (1H, d, J=16 Hz), 4.90 (1H, d, J=16 Hz), 5.12 (1H, d, J=8 Hz), 6.72 (1H, d, J=8 Hz), 7.07–7.77 (8H, m), 8.89 (1H, s); Mass (m/z): 555 ($M^+$)

EXAMPLE 47-2

The following compound was prepared in a similar manner to that of Example 47-1.

N-[(3RS)-1-[(3-azabicyclo[3.2.2]non-3-yl) carbonylmethyl]-5-cyclohexyl-2,3-dihydro-2-oxo-1H-1,4-benzodiazepin-3-yl]-N'-(cyclohexyl)urea mp: 195°–197° C.; IR (KBr): 3409, 3290, 2927, 2845, 1738, 1690, 1636, 1445, 1200, 1000, 769 $cm^{-1}$; $^1H$ NMR (DMSO-$d_6$, δ): 0.91–2.06 (30H, m), 2.88 (1H, t, J=11 Hz), 3.27–3.80 (4H, m), 4.48 (1H, d, J=18 Hz), 4.88 (1H, d, J=18 Hz), 5.09 (1H, d, J=9 Hz), 6.39 (1H, d, J=9 Hz), 6.85 (1H, d, J=8 Hz), 7.27 (1H, d, J=8 Hz), 7.33 (1H, t, J=8 Hz), 7.55 (1H, t, J=8 Hz), 7.70 (1H, d, J=8 Hz); Mass (m/z): 547 ($M^+$)

EXAMPLE 48

The following compound was prepared in a similar manner to that of Example 47-1.

N-[(3RS)-1-[(3-azabicyclo[3.2.2]non-3-yl) carbonylmethyl]-5-cyclopentyl-2,3-dihydro-2-oxo-1H-1,4-benzodiazepin-3-yl]-N'-(3-methylphenyl)urea mp: 132°–134° C.; IR (KBr): 3368, 2936, 2864, 1681, 1656, 1557, 1490, 1451, 1201, 1014, 774 $cm^{-1}$; $^1H$ NMR ($CDCl_3$, δ): 1.23–2.33 (18H, m), 3.25–3.36 (1H, m), 3.44–3.86 (4H, m), 4.40 (1H, d, J=16 Hz), 4.88 (1H, d, J=16 Hz), 5.48 (1H, d, J=7 Hz), 6.57 (1H, d, J=8 Hz), 6.63 (1H, s), 6.83 (1H, d, J=8 Hz), 7.05–7.32 (4H, m), 7.45 (1H, t, J=8 Hz), 7.58 (1H, d, J=8 Hz); Mass (m/z): 541 ($M^+$)

EXAMPLE 49

To a suspension of sodium hydride (0.015 g of a 63.8% dispersion in mineral oil) in dry N,N-dimethylformamide (20 ml) was added N-[(3RS)-5-cyclopentyl-2,3-dihydro-2-oxo-1H-1,4-benzodiazepin-3-yl]-N'-(3-methylphenyl)urea (0.130 mg) at 5°–10° C. The mixture was stirred for 1 hour at the same temperature and then at room temperature for 1 hour. To the mixture was added sodium iodide (0.052 g) and followed a solution of 2-chloromethyl-3-methylpyridine (0.056 g) in dry N,N-dimethylformamide. The mixture was stirred at ambient temperature overnight. The resultant mixture was concentrated in vacuo to give a brown oil. The oil was dissolved with ethyl acetate (100 ml) and washed with 10% citric acid aqueous solution (50 ml), saturated sodium bicarbonate aqueous solution (50 ml) and a brine (50 ml). The organic layer was dried over magnesium sulfate. Filtration and evaporation gave a crude product. The crude product was subjected by column chromatography on silica gel with chloroform and a mixture of chloroform and ethyl acetate (5:1) as eluents to afford N-[(3RS)-5-cyclopentyl-2,3-dihydro-1-(3-methylpyridin-2-yl)methyl-2-oxo-1H-1,4-benzodiazepin-3-yl]-N'-(3-methylphenyl)-urea (0.065 g).

mp: 198°–199° C.; IR (KBr): 3344, 2949, 1673, 1649, 1559, 1492, 1448, 1208, 782 $cm^{-1}$; $^1H$ NMR (DMSO-$d_6$, δ): 1.13–1.23 (1H, m), 1.46–1.65 (4H, m), 1.78–1.88 (1H, m), 1.98–2.08 (1H, m), 2.22 (3H, s), 2.29 (3H, s), 3.41–3.52 (1H, m), 5.13 (1H, d, J=18 Hz), 5.20 (1H, d, J=8 Hz), 5.32 (1H, d, J=18 Hz), 6.73 (1H, d, J=8 Hz), 7.08–7.17 (3H, m), 7.18 (1H, s), 7.28–7.35 (2H, m), 7.50–7.58 (3H, m), 7.73 (1H, d, J=8 Hz), 8.16 (1H, d, J=4 Hz), 8.88 (1H, s); Mass (m/z): 481 ($M^+$)

EXAMPLE 50

To a solution of N-[(3RS)-5-cycloheptyl-2,3-dihydro-2-oxo-1H-1,4-benzodiazepin-3-yl]-N'-(3-methylphenyl)urea (0.102 g) and N-bromomethylcarbonyl-3-azabicyclo[3.2.2] nonane (0.079 g) in dry N,N-dimethylformamide (10 ml) was added sodium hydride (0.011 g of a 63.8% dispersion in mineral oil) at 5°–10° C. The mixture was stirred at the same temperature for 30 minutes and then at ambient temperature overnight. The resultant mixture was treated with 0.1 g of acetic acid at room temperature for 30 minutes and then concentrated in vacuo. The residue was disolved with ethyl acetate (100 ml) and washed with saturated sodium hydrogen carbonate aqueous solution (20 ml) and a brine (20 ml). The organic layer was dried over magnesium sulfate. Filtration and evaporation gave a crude product. The crude product was purified by column chromatography on silica gel with chloroform and a mixture of chloroform and ethyl acetate (5:1) as eluents to afford N-[(3RS)-1-[(3-azabicyclol3.2.2]non-3-yl)carbonylmethyl]-5-cycloheptyl-2,3-dihydro-2-oxo-1H-1,4-benzodiazepin-3-yl]-N'-(3-methylphenyl)urea (0.090 g).

mp: 132°–135° C.; IR (KBr): 3365, 2927, 2861, 1697, 1653, 1558, 1455, 1200, 1113 $cm^{-1}$; $^1H$ NMR ($CDCl_3$, δ): 1.35–2.20 (22H, m), 2.28 (3H, s), 3.44–3.83 (4H, m), 4.34 (1H, d, J=16 Hz), 4.91 (1H, d, J=16 Hz), 5.43 (1H, d, J=8 Hz), 6.66 (1H, d, J=8 Hz), 6.78–6.82 (2H, m), 7.06–7.32 (5H, m), 7.45 (1H, t, J=8 Hz), 7.56 (1H, d, J=8 Hz)

EXAMPLE 51

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-[3-(N-phenylaminosulfonyl) phenyl]urea was obtained in a similar manner to that of Example 58.

NIMR (DMSO-$d_6$, δ): 1.5–1.7 (8H, br), 2.02 (2H, br), 3.46–3.74 (4H, m), 4.73 (1H, Jabq. 17.0 Hz, 54.5 Hz), 5.01 (1H, Jabq. 17.0 Hz, 54.5 Hz), 5.32 (1H, d, 8.3 Hz), 7.0–7.7 (17H, m), 8.02 (1H, s), 9.36 (1H, s), 10.25 (1H, s); IR (Nujol, $cm^{-1}$): 3300, 1655; Mass (FAB): 709 ($M^+$+1); mp: 180.9°–187.7° C.

EXAMPLE 52

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-(3-aminosulfonylphenyl)urea (200 mg) was stirred in N,N-dimethylformamide (2.0 ml) at room temperature. Sodium hydride (25.6 mg) was added to the reaction mixture at room temperature, stirred for 1 hour. Ethyl acetate and water were added to the reaction mixture and the organic layer was separated, washed with water and brine, and dried over magnesium sulfate, evaporated to dryness, washed with isopropyl ether and vacuumed to afford N-[(3RS)-1-(3-azabicyclo[3.2.2]non-3-yl)carbonylmethyl-2,3-dihydro-5-(2-fluorophenyl)-2-oxo-1H-1,4-benzodiazepin-3-yl]-N'-[3-(N,N-dimethylaminosulfonyl) phenyl]urea.

NMR (DMSO-$d_6$, δ): 1.5–1.7 (8H, br), 1.99 (2H, br), 2.59 (6H, s), 3.45–3.76 (4H, m), 4.74 (1H, Jabq. 16.8 Hz, 52.4 Hz), 5.01 (1H, Jabq. 16.8 Hz, 52.4 Hz), 5.34 (1H, d, 8.4 Hz), 7.2–7.7 (12H, m), 9.46 (1H, s); IR (Nujol, $cm^{-1}$): 3305, 1650; Mass (APCI): 661 ($M^{+}$+1); mp: 180.6°–184.7° C.

EXAMPLE 53

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-(1H-indazol-6-yl)urea was obtained in a similar manner to that of Example 13-7.

NMR (DMSO-$d_6$, δ): 1.59 (8H, br), 1.97 (2H, br), 3.38 (2H, br), 3.71 (2H, br), 4.36 (1H, Jabq, 16.3 Hz, 108.3 Hz), 4.91 (1H, Jabq, 16.3 Hz, 108.3 Hz), 5.71 (1H, d, 7.59 Hz), 6.88–8.24 (12H, m);

Mass (APCI): 594 ($M^{+}$+1); IR (Nujol, $cm^{-1}$): 3270, 1638; mp: 160.0° C. (dec.)

EXAMPLE 54

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-(3-trifluoromethoxyphenyl)urea was obtained in a similar manner to that of Example 58.

MNR (DMSO-$d_6$, δ): 1.5–1.7 (8H, br), 2.01 (2H, br), 3.45–3.77 (4H, m), 4.73 (1H, Jabq, 16.8 Hz, 55.4 Hz), 5.01 (1H, Jabq, 16.8 Hz, 55.4 Hz), 5.32 (1H, d, 8.3 Hz), 6.8–7.7 (12H, m), 9.37 (1H, s); IR (Nujol, $cm^{-1}$): 3300, 1640, 1605; Mass (APCI): 638 ($M^{+}$+1); mp: 156.3°–164.2° C.

EXAMPLE 55

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-methyl-N'-(3-methylphenyl) urea was obtained in a similar manner to that of Example 58.

NMR (DMSO-$d_6$, δ): 1.5–1.7 (8H, br), 1.99 (2H, br), 2.34 (3H, s), 3.19 (3H, s), 3.51–3.63 (4H, m), 4.72 (1H, Jabq, 16.8 Hz, 36.6 Hz), 4.90 (1H, Jabq, 16.8 Hz, 36.6 Hz), 5.27 (1H, d, 8.2 Hz), 6.32 (1H, d, 8.2 Hz), 7.1–7.7 (12H, m); IR (Nujol, $cm^{-1}$): 3400, 1655, 1600; Mass (APCI): 582 ($M^{+}$+1); mp: 207.2°–212.2° C.

EXAMPLE 56

N-[(3RS)-1-(3-azabicyclo[3.2.2]non-3-yl) carbonylmethyl-2,3--dihydro-5-(2-fluorophenyl)-2-oxo-1H-1,4-benzodiazepin-3-yl]-N'-(3-ethoxyphenyl)urea was obtained in a similar manner to that of Example 58.

NMR (DMSO-$d_6$, δ): 1.29 (3H, t, 6.9 Hz), 1.5–1.7 (8H, br), 1.99 (2H, br), 3.46–3.75 (4H, m), 3.95 (2H, q, 6.9 Hz), 4.72 (1H, Jabq, 16.8 Hz, 58.0 Hz), 5.01 (1H, Jabq, 16.8 Hz, 58.0 Hz), 5.32 (1H, d, 8.4Hz), 6.4–7.7 (12H, m), 9.04 (1H, s); IR (Nujol, $cm^{-1}$): 3300, 1635, 1605; Mass (APCI): 598 ($M^{+}$+1); mp: 157.9–166.2° C.

EXAMPLES 57

A mixture of N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-(3-hydroxymethylphenyl)urea and mangan dioxide in acetone was stirred at room temperature for 3 hours. The mangan dioxide was removed by filtration, and the filtrate was evaporated to dryness, and washed with isopropyl ether to afford N-[(3RS)-1-(3-azabicyclo[3.2.2]non-3-yl)carbonylmethyl-2,3-dihydro-5-(2-fluorophenyl)-2-oxo-1H-1,4-benzodiazepin-3-yl]-N'-(3-formylphenyl)urea.

NMR (DMSO-$d_6$, δ): 1.5–1.7 (8H, br), 2.00 (2H, br), 3.44–3.78 (4H, m), 4.73 (1H, Jabq, 16.6 Hz, 56.3 Hz), 5.01 (1H, Jabq, 16.6 Hz, 56.3 Hz), 5.34 (1H, d, 8.4 Hz), 7.2–7.7 (12H, m) 8.01 (1H, s), 9.34 (1H, s), 9.94 (1H, s); IR (Nujol, $cm^{-1}$): 3250, 1700, 1670, 1645, 1600; Mass (APCI): 582 ($M^{+}$+1); mp: 164.4°–182.0° C

EXAMPLE 58

A mixture of [(3RS)-1-(3-azabicyclo[3.2.2]non-3-yl) carbonylmethyl-2,3-dihydro-3-(imidazol-1-yl) carbonylamino-5-(2-fluoro-phenyl)-1H-1,4-benzodiazepin-2-one (500 mg) and 3-aminobenzyl alcohol (128 mg) in dimethylformamide (5.0 ml) was stirred at 100° C. for 5 hours. Ethyl acetate and water were added to the reaction mixture at room temperature, and organic layer was separated, washed with water and brine, dried over magnesium sulfate, and isolated by column chlomatography on silica gel to afford N-[(3RS)-1-(3-azabicyclo[3.2.2]non-3-yl)carbonylmethyl-2,3-dihydro-5-(2-fluorophenyl)-2-oxo-1H-1,4-benzodiazepin-3-yl]-N'- (3-hydroxymethylphenyl) urea.

NMR (DMSO-$d_6$, δ): 1.5–1.7 (8H, br), 1.99 (2H, br), 3.45–3.78 (4H, m), 4.42 (2H, d, 5.8 Hz), 4.72 (1H, Jabq, 16.7 Hz, 57.8 Hz), 5.01 (1H, Jabq, 16.7 Hz, 57.8 Hz), 5.13 (1H, t, 5.8 Hz), 5.33 (1H, d, 8.5 Hz), 6.8–7.7 (12H, m), 9.01 (1H, s); IR (Nujol, $cm^{-1}$): 3300, 1670, 1637, 1610; Mass (APCI): 584 ($M^{+}$+1); mp: 143.2°–160.7° C.

EXAMPLE 59

A mixture of N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-(3-nitrophenyl)urea and 10% Pd on carbon in ethanol was stirred at 1 atm $H_2$ gas for several hours.

The 10% Pd on carbon was removed by filtration, and the filtrate was evaporated to dryness under reduced pressure, and isolated by column chromatography on silica gel to afford N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-(3-aminophenyl)urea.

NMR (DMSO-$d_6$, δ): 1.5–1.7 (8H, br), 1.99 (2H, br), 3.46–3.69 (4H, m), 4.71 (1H, Jabq, 18.6 Hz, 57.9 Hz), 5.00 (1H, Jabq, 18.6 Hz, 57.9 Hz), 5.31 (1H, d, 8.5 Hz), 6.12–6.17 (1H, m), 6.5–7.7 (11H, m), 8.71 (1H, s); IR (Nujol, $cm^{-1}$): 3300, 1650; Mass (APCI): 569 ($M^{+}$+1); mp: >250° C.

EXAMPLE 60

N-[(3RS)-1-(3-azabicyclo[3.2.2]non-3-yl) carbonylmethyl-2,3-dihydro-5-(2-fluorophenyl)-2-oxo-1H-1,4-benzodiozepin- 3-yl]-N'-(2-chlorophenyl)urea was obtained in a similar manner to that of Example 1.

NMR (DMSO-$d_6$, δ): 1.5–1.7 (8H, br), 2.03 (2H, br), 3.45–3.81 (4H, m), 4.72 (1H, Jabq, 16.7 Hz, 59.5 Hz), 5.02 (1H, Jabq, 16.7 Hz, 59.5 Hz), 5.36 (1H, d, 8.3 Hz), 6.9–8.6 (12H, m), 8.70 (1H, s); IR (Nujol, $cm^{1}$): 3350, 1660; Mass (APCI): 588 ($M^{+}$+1); mp: 231.0°–232.9° C.

EXAMPLE 61

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl)-N'-(2-methylphenyl)urea was obtained in a similar manner to that of Example 1.

NMR (DMSO-$d_6$, δ): 1.5–1.8 (8H, br), 2.01 (2H, br), 3.44–3.81 (4H, m), 2.23 (3H, s), 4.71 (1H, Jabq, 16.7 Hz, 62.0 Hz), 5.02 (1H, Jabq, 16.7 Hz, 62.0 Hz), 5.35 (1H, d, 8.4 Hz), 6.8–8.1 (12H, m), 8.27 (1H, s); IR (Nujol, $cm^{-1}$): 3330, 1650; Mass (APCI): 568 ($M^{+}$+1); mp: 166.6°–171.5° C.

EXAMPLE 62

N-[(3RS)-1-(3-azabicyclo[3.2.2]non-3-yl] carbonylmethyl-2,3-dihydro-5-(2-fluorophenyl)-2-oxo-1H-1,4-benzodiazepin-3-yl]-N'-(3-methylphenyl)thiourea was obtained in a similar manner to that of Example 1.

NMR (DMSO-$d_6$, δ): 1.5–1.7 (8H, br), 2.01 (2H, br), 2.30 (3H, s), 3.32–3.78 (4H, m), 4.75 (1H, Jabq. 16.7 Hz, 53.3 Hz), 5.02 (1H, Jabq. 16.7 Hz, 53.3 Hz), 5.99 (1H, d, 7.5 Hz), 6.9–7.7 (12H, m), 8.76 (1H, d, 7.5 Hz); IR (Nujol, $cm^{-1}$): 3300, 1650; Mass (APCI): 584 ($M^+$+1); mp: 129.4°–134.4° C.

EXAMPLE 63

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-(3-aminosulfonylphenyl)urea was obtained in a similar manner to that of Example 13-7.

NMR (DMSO-$d_6$, δ): 1.5–1.8 (8H, br), 2.03 (2H, br), 3.41–3.78 (4H, m), 4.73 (1H, Jabq. 16.8 Hz, 56.5 Hz), 5.01 (1H, Jabq. 16.8 Hz, 56.5 Hz), 5.33 (1H, d, 8.3 Hz), 7.2–7.7 (12H, m), 7.98 (1H, s), 9.35 (1H, s); IR (Nujol, $cm^{-1}$): 3300, 1650; Mass (APCI): 633 ($M^+$+1); mp: 220.8°–226.4° C.

EXAMPLE 64

N-[(3RS)-1-($^3$-azabicyclo[3.2.2]non-3-yl) carbonylmethyl-2,3-dihydro-5-(2-fluorophenyl)-2-oxo-1H-1,4-benzodiazepin-3-yl]-N'-(3-ethylphenyl)urea was obtained in a similar manner to that of Example 1.

NMR (DMSO-$d_6$, δ): 1.15 (3H, t, 7.5 Hz), 1.5–1.8 (8H, br), 2.01 (2H, br), 2.53 (2H, q, 7.5 Hz), 3.44–3.77 (4H, m), 4.72 (1H, Jabq. 16.8 Hz, 57.5 Hz), 5.01 (1H, Jabq. 16.8 Hz, 57.5 Hz), 5.33 (1H, d, 8.5 Hz), 6.7–7.7 (12H, m), 8.99 (1H, s); IR (Nujol, $cm^{-1}$): 3300, 1650; Mass (APCI): 582 ($M^+$+1); mp: 185.2°–192.3° C.

EXAMPLE 65

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-(3-cyanophenyl)urea was obtained in a similar manner to that of Example 1.

NMR (DMS-$d_6$,δ): 1.5–1.8 (8H, br), 2.02 (2H, br), 3.46–3.76 (4H, m), 4.73 (1H, Jabq. 16.8 Hz, 56.2 Hz), 5.01 (1H, Jabq. 16.8 Hz, 56.2 Hz), 5.33 (1H, d, 8.3 Hz), 7.2–7.8 (12H, m), 7.93 (1H, s), 9.41 (1H, s); IR (Nujol, $cm^{-1}$): 3350, 2240, 1650; Mass (APCI): 579 ($M^+$+1); mp: 188.5°–194.9° C.

EXAMPLE 66

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-(3-nitrophenyl)urea was obtained in a similar manner to that of Example 1.

NMR (DMSO-$d_6$, δ): 1.5–1.7 (8H, br), 2.03 (2H, br), 3.47–3.78 (4H, m), 4.74 (1H, Jabq. 16.7 Hz, 55.2 Hz), 5.02 (1H, Jabq. 16.7 Hz, 55.2 Hz), 5.34 (1H, d, 8.3 Hz), 7.2–7.8 (12H, m), 8.50 (1H, s), 9.60 (1H, s); IR (Nujol, $cm^{-1}$): 3300, 1650, 1525; Mass (APCI): 599 ($M^+$+1); mp: 179.6°–187.1° C.

EXAMPLE 67

N-[(3RS)-1-(3-azabicyclo[3.2.2]non-3-yl) carbonylmethyl-2,3-dihydro-5-(2-fluorophenyl)-2-oxo-1H, 1,4-benzodiazepin-3-yl]-N'-(3-fluorophenyl)urea was obtained in a similar manner to that of Example 1.

NMR (DMSO-$d_6$, δ): 1.5–1.8 (8H, br), 2.01 (2H, br), 3.39–3.75 (4H, m), 4.73 (1H, Jabq. 16.7 Hz, 56.4 Hz), 5.01 (1H, Jabq. 16.7 Hz, 56.4 Hz), 5.33 (1H, d, 8.3 Hz), 6.7–7.7 (12H, m), 9.30 (1H, s); IR (Nujol, $cm^{-1}$): 3300, 1650; Mass (APCI): 572 ($M^+$+1); mp: 167.8°–177.2° C.

EXAMPLE 68

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-(3-bromophenyl)urea was obtained in a similar manner to that of Example 1.

NMR (DMSO-$d_6$, δ): 1.5–1.7 (8H, br), 2.01 (2H, br), 3.46–3.75 (4H, m), 4.73 (1H, Jabq. 16.7 Hz, 56.3 Hz), 5.01 (1H, Jabq. 16.7 Hz, 56.3 Hz), 5.31 (1H, d, 8.3 Hz), 7.1–7.8 (12H, m), 9.25 (1H, s); IR (Nujol, $cm^{-1}$): 3300, 1650; Mass (APCI): 634, 632; mp: 172.6°–186.5° C.

EXAMPLE 69

(3RS)-1-(3-azabicyclo[3.2.2]non-3-yl)carbonylmethyl-2,3-dihydro-3-(3-cyanophenyl)caronylamino-5-(2-fluorophenyl)-1H-1,4-benzodiazepin-2-one was obtained in a similar manner to that of Example 71.

NMR (DMSO-$d_6$, δ): 1.5–1.7 (8H, br), 1.99 (2H, br), 3.57 (4H, br m), 4.81 (1H, Jabq. 16.7 Hz, 32.3 Hz), 4.98 (1H, Jabq. 16.7 Hz, 32.3 Hz), 7.2–8.5 (12H, m), 9.93–9.97 (1H, m); IR (Nujol, $cm^{-1}$): 2240, 1650; Mass (APCI): 564 ($M^+$+1); mp: 154.2°–154.8° C.

EXAMPLE 70

(3RS)-1-(3-azabicyclo[3.2.2]non-3-yl)carbonylmethyl-2,3-dihydro-3-(3-methoxycarbonylphenyl)carbonylamino-5-(2-fluorophenyl)-1H-1,4-benzodiazepin-2-one was obtained in a similar manner to that of Example 71.

NMR (DMSO-$d_6$, δ): 1.5–1.7 (8H, br), 1.99 (2H, br), 3.57(4H, br), 3.90 (3H, s), 4.81 (1H, Jabq. 16.8 Hz, 33.1 Hz), 4.98 (1H, Jabq. 16.8 Hz, 33.1H, z), 5.71 (1H, d, 8.0 Hz), 7.2–8.3 (12H, m), 9.91–9.95 (1H, m); IR (Nujol, $cm^{-1}$): 1730, 1655, 1603; Mass (APCI): 597 ($M^+$+1); mp: 165.8°–177.2° C.

EXAMPLE 71

A mixture of (3RS)-3-amino-1-[(3-azabicyclo[3.2.2]non-3-yl)carbonylmethyl]-2,3-dihydro-5-(2-fluorophenyl)-1H-1,4-benzodiazepin-2-one, 3-hydroxybenzoic acid, and WSC-HCl was stirred in $CH_2Cl_2$ at room temperature overnight. Ethyl acetate and iN HCl were added in the reaction mixture and organic layer was separated, and washed with water and brine, and dried over magnesium sulfate, evaporated in vacuo. The colorless powder was washed with isopropyl ether to afford (3RS)-1-(3-azabicyclo[3.2.2]non-3-yl)carbonylmethyl-2,3-dihydro-3-(3-hydroxyphenyl) carbonylamino-5-(2-fluorophenyl)-1H-1,4-benzodiazepin-2-one.

NMR (DMSO-$d_6$, δ): 1.5–1.7 (8H, br), 1.99 (2H, br), 3.56 (4H, br), 4.80 (1H, Jabq. 16.7 Hz, 34.4 Hz), 4.97 (1H, Jabq. 16.7 Hz, 34.4 Hz), 5.67 (1H, d, 8.1 Hz), 6.9–7.7 (12H, m), 9.39 (1H, d, 8.1 Hz), 9.67 (1H, s); IR (Nujol, $cm^{-1}$): 3250, 1660, 1630; Mass (APCI): 555 ($M^+$+1); mp: >250° C.

EXAMPLE 72

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-(3-hydroxyphenyl)urea was obtained in a similar manner to that of Example 13-7.

NMR (DMSO-$d_6$, δ): 1.5–1.8 (8H, br), 1.99 (2H, br), 3.44–3.76 (4H, m), 4.72 (1H, Jabq. 16.8 Hz, 58.0 Hz), 5.01 (1H, Jabq. 16.8 Hz, 58.0 Hz), 5.31 (1H, d, 8.5 Hz), 6.3–7.9 (12H, m), 8.92 (1H, s), 9.26 (1H, s); IR (Nujol, $cm^{-1}$): 3300, 1650; Mass (APCI): 570 ($M^+$+1); mp: 183.9°–185.1° C.

EXAMPLE 73

N-1(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-(3-aminocarbonylphenyl)urea was obtained in a similar manner to that of Example 13-7.

NMR (DMSO-$d_6$, δ): 1.5–1.7 (8H, br), 1.99 (2H, br), 3.46–3.69 (4H, m), 4.72 (1H, Jabq. 16.4 Hz, 57.1 Hz), 5.01 (1H, Jabq. 16.4 Hz, 57.1 Hz), 5.34 (1H, d, 8.3 Hz), 7.2–7.9 (12H, m), 9.1 (1H, s); IR (Nujol, $cm^{-1}$): 3350, 1650; Mass (APCI): 597 ($M^+$+1); mp: 217.2° C. (dec.)

EXAMPLE 74

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-phenylurea was obtained in a similar manner to that of Example 1.

NMR (DMSO-$d_6$, δ): 1.5–1.7 (8H, br), 2.01 (2H, br), 3.45–3.76 (4H, m), 4.72 (1H, Jabq. 16.8 Hz, 58.1 Hz), 5.01 (1H, Jabq. 16.8 Hz, 58.1 Hz), 5.33 (1H, d, 8.5 Hz), 6.8–7.7 (13H, m), 9.06 (1H, s); IR (Nujol, $cm^{-1}$): 3350, 1650; Mass (APCI): 554 ($M^+$+1); mp: 182.2° C. (dec.)

EXAMPLE 75

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-(3-chlorophenyl)urea was obtained in a similar manner to that of Example 1.

NMR ($DMSO_6$, δ): 1.55–1.64 (8H, br), 2.01 (2H, br), 3.40–3.78 (4H, m), 4.73 (1H, Jabq. 16.8 Hz, 56.6 Hz), 5.01 (1H, Jabq. 16.8 Hz, 56.6 Hz), 5.32 (1H, , 8.33 Hz), 6.96–7.70 (12H, m), 9.28 (1H, s); IR (Nujol, $cm^{-1}$): 3300, 1695, 1670, 1630, 1608; Mass (APCI): 588 ($M^+$+1); mp: 160.0° C. (dec.)

EXAMPLE 76

N-[(3RS)-1-(5-methoxycarbonylthiophen-2-yl)methyl-5-(2-fluorophenyl)-2,3-dihydro-2-oxo-1H-1,4-benzodiazepin-3-y]-N'-(3-methylphenyl)urea was obtained in a similar manner to that of Example 1 as a white crystalline powder.

mp: 225°–226° C. IR (Nujol, $cm^{-1}$): 3300, 1705, 1675, 1646, 1610, 1548, 1449, 1372, 1330, 1290, 1273, 1260, 1210, 1093, 765, 748; $^1$H-NMR (DMSO-$d_6$, δ): 2.25 (3H, s), 3.73 (3H, s), 5.33 (1H, d, J=8.4 Hz), 5.48 (2H, ABq, J=15.9 Hz, 64.6 Hz), 6.7–7.85 (15H, m), 8.99 (1H, s); APCI-MS (m/z): 557 ($M^+$+1)

EXAMPLE 77

N-(3RS)-1-(5-carboxythiophen-2-yl)methyl-5-(2-fluorophenyl)-2,3-dihydro-2-oxo-1H-1,4-benzodiazepin-3-yl]-N'-(3-methylphenyl)urea was obtained in a similar manner to that of preparation 18-4 as a white crystalline powder.

mp: 260°–226° C. (dec.) IR (Nujol, $cm^{-1}$): 3300, 2700–2300, 1665, 1640, 1610, 1560, 1535, 1490, 1455, 1447, 1380, 1350, 1278, 1212, 1195, 1108, 1040, 930, 775, 760 (sh), 750, 690; $^1$H-NMR (DMSO-$d_6$, δ): 2.25 (3H, s), 5.32 (1H, d, J=8.3 Hz), 5.46 (2H, ABq, J=15.8 Hz, 63.8 Hz), 6.7–7.85 (15H, m), 8.99 (1H, s), 12.97 (1H, br); APCI-MS (m/z): 543 ($M^+$+1)

EXAMPLE 78

N-{(3RS)-1-[5-(3-azabicyclo[3.2.2]non-3-yl)carbonyl-thiophen-2-yl]methyl-5-(2-fluorophenyl)-2,3-dihydro-2-oxo-1H-1,4-benzodiazepin-3-yl}-N'-(3-methylphenyl)urea was obtained in a similar manner to that of Example 18-1 as a white crystalline powder.

mp: 174°–177° C. IR (Nujol, $cm^{-1}$): 3300, 1670, 1648, 1608, 1560, 1460, 1446, 1374, 1278, 1210, 820, 770 (sh), 760, 725, 660; $^1$H-NMR (DMSO-$d_6$, δ): 1.54 (8H, s), 1.93 (2H, br, s), 2.24 (3H, s), 3.53–3.73 (4H, m), 5.31 (1H, d, J=8.4 Hz), 5.44 (2H, ABq, J=15.8 Hz, 70.3 Hz), 6.7–7.9 (15H, m), 8.97 (1H, s) APCI-MS (m/z): 650 ($M^+$+1)

EXAMPLE 79

N-[(3RS)-1-(3-azabicyclo[3.2.2]non-3-yl) carbonylmethyl- 2,3-dihydro-5-(2-fluorophenyl)-2-oxo-1H-1,4-benzodiazepin-3-yl]-N'-[3-(N-methylcarbamoyl) phenyl]urea was obtained in a similar manner to that of Example 13-7 as a light yellow crystalline powder.

mp: 193.5°–193.8° C.; IR (Nujol, $cm^{-1}$): 3300, 1680(sh), 1670(sh), 1650, 1635, 1550, 1480, 1460 (sh), 1448, 1375, 1325, 1214, 1100, 1010, 936, 808, 750; $^1$H-NMR (DMSO-$d_6$, δ): 1.4–1.8 (8H, m), 1.95–2.1 (2H, br, s), 2.75 (311, d, J=4.3 Hz), 3.4–3.75 (4H, m), 4.81 (2H, ABq, J=16.7 Hz, 58.1Hz), 5.34 (1H, d, J=8.4 Hz), 7.2–7.81 (13H, m), 8.34 (1H, q, J=4.3 Hz), 9.17 (1H, s)

EXAMPLE 80

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-[3-(3-oxo-2,3-dihydropyridazin-6-yl)phenyl]urea was obtained in a similar manner to that of Example 13-7.

NMR (DMSO-$d_6$, δ): 1.5–1.7 (8H, br), 1.99 (2H, br), 3.46–3.69 (4H, m), 4.73 (1H, Jabq. 16.7 Hz, 57.6 Hz), 5.01 (1H, Jabq. 16.7 Hz, 57.6 Hz), 5.34 (1H, d, 8.3 Hz), 6.9–7.9 (14H, m), 9.21 (1H, s); IR (Nujol, $cm^{-1}$): 3300, 1670, 1650, 1600; Mass (APCI): 648 ($M^+$+1); mp: 156.2° C. (dec.)

EXAMPLE 81

N-[(3RS)-1-($^3$-azabicyclo[3.2.2]non-3-yl) carbonylmethyl-2,3-dihydro-5-(2-fluorophenyl)-2-oxo-1H-1,4-benzodiazein-3-yl]-N'-(3-dihydroxyborylphenyl)urea was obtained in a similar manner to that of Example 58.

NMR (DMSO-$d_6$, δ): 1.5–1.8 (8H, br), 2.02 (2H, br), 3.41–3.76 (4H, m), 4.72 (1H, Jabq. 16.7 Hz, 57.8 Hz), 5.01 (1H, Jabq. 16.7 Hz, 57.8 Hz), 5.34 (1H, d, 8.5 Hz), 7.1–7.7 (12H, m), 7.96 (2H, s), 8.93 (1H, s); IR (Nujol, $cm^-$): 3350, 1650; Mass (FAB): 597 ($M^+$); mp: 208.3°–220.2° C.

EXAMPLE 82

Pottasium salt of N-[(3RS)-1-(3-azabicyclol3.2.2]non-3-yl)carbonylmethyl-2,3-dyhidro-5-(2-fluorophenyl)-2-oxo-1H-1,4-benzodiazepin-3-yl]-N'-(3-sulfomethylphenyl)urea was obtained in a similar manner to that of Example 58.

NMR (DMSO-$d_6$, δ): 1.5–1.7 (8H, br), 2.03 (2H, br), 3.47–3.78 (4H, m), 4.74 (1H, Jabq. 16.7 Hz, 55.2 Hz), 5.02 (1H, Jabq. 16.7 Hz, 55.2 Hz), 5.34 (1H, d, 8.3 Hz), 7.2–7.8 (12H, m), 8.50 (1H, s), 9.60 (1H, s); IR (Nujol, $cm^{-1}$): 3300, 1650, 1525; Mass (APCI): 599 ($M^+$+1); mp: 179.6°–187.1° C.

EXAMPLE 83

Pottasium salt of N-[(3RS)-1-(3-azabicyclo[3.2.2]non-3-yl)carbonylmethyl-2,3-dihydro-5-(2-fluorophenyl)-2-oxo- 1H-1,4-benzodiazepin-3-yl]-N'-[3-(1-sulfoethyl)phenyl] urea was obtained in a similar manner to that of Example 58.

NMR (DMSO-$d_6$, δ): 1.43 (3H, d, 7.1 Hz), 1.5–1.7 (8H, br), 1.99 (2H, br), 3.46–3.72 (5H, m), 4.74 (1H, Jabq. 16.8 Hz, 52.2 Hz), 5.00 (1H, Jabq. 16.8 Hz, 52.2 Hz), 5.33 (1H, d, 8.5 Hz), 6.8–7.7 (12H, m), 8.99 (1H, s); IR (Nujol, $cm^{-1}$): 3350, 1650; Mass (FAB): 700 ($M^+$+1); mp: >250° C.

EXAMPLE 84

Potassium salt of N-[(3RS)-1-(3-azabicyclo[3.2.2]non-3-yl)carbonylmethyl-2,3-dihydro-5-(2-fluorophenyl)-2-oxo-1H-1,4-benzodiazepin-3-yl]-N'-(3-sulfophenyl)urea was obtained in a similar manner to that of Example 58. NMR (DMSO-$d_6$, δ): 1.5–1.7 (8H, br), 1.98 (2H, br), 3.45 –3.75 (4H, m), 4.74 (1H, Jabq. 16.7 Hz, 54.0 Hz), 5.01 (1H, Jabq. 16.7 Hz, 54.0 Hz), 5.33 (1H, d, 8.4 Hz), 7.0–7.7 (12H, m), 9.11 (1H, s); IR (Nujol, $cm^{-1}$): 3330, 1650; Mass (FAB): 672 ($M^+$+1); mp: >250° C.

EXAMPLE 85

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-[3-(5-tetrazolylaminocarbonyl) phenyl]urea was obtained in a similar manner to that of Example 58.

NMR (DMSO-$d_6$, δ): 1.5–1.7 (8H, br), 2.01 (2H, br), 3.45–3.78 (4H, m), 4.73 (1H, Jabq. 16.8 Hz, 57.6 Hz), 5.01 (1H, Jabq. 16.8 Hz, 57.6 Hz), 5.35 (1H, d, 8.4 Hz), 7.1–7.7 (12H, m), 9.30 (1H, s), 12.40 (1H, s); IR (Nujol, $cm^{-1}$): 3340, 1660; Mass (FAB): 665 ($M^+$+1); mp: 193.2–195.5° C.

EXAMPLE 86

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-[3-(1-carboxyethyl)phenyl]urea was obtained in a similar manner to that of Example 58.

NMR (DMSO-$d_6$, δ): 1.32 (3H, d, 7.1 Hz), 1.5–1.7 (8H, br), 1.99 (2H, br), 3.45–3.74 (5H, m), 4.73 (1H, Jabq. 16.8 Hz, 54.8 Hz), 5.00 (1H, Jabq. 16.8 Hz, 54.8 Hz), 5.33 (1H, d. 8.4 Hz), 6.8–7.7 (12H, m), 9.06 (1H, s); IR (Nujol, $cm^{-1}$): 3300, 1670,, 1640, 1610; Mass (APCI): 626 ($M^+$+1); mp: 187.2–204.4° C.;

EXAMPLE 87

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-[3-(4,5-dihydro-5-oxo-1,2,4-oxadiazol-3-yl)phenyl]urea was obtai.ned in a similar manner to that of Example 58.

NMR (DMSO-$d_6$, δ): 1.55 (8H, br), 1.99 (2H, br), 3.5–3.7 (4H, m), 4.68–4.95 (2H, br m), 5.35 (1H, d, 8.8 Hz), 7.0–7.6 (12H, m); IR (Nujol, $cm^{-1}$): 3300, 1680, 1605; Mass (FAB): 638 ($M^+$+1); mp: 205.2° C. (dec.)

EXAMPLE 88

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-(3-acetylaminosulfonylphenyl) urea was obtained in a similar manner to that of Example 52.

NMR (DMSO-$d_6$, δ): 1.5–1.7 (8H, br), 1.92 (3H, s), 1.99 (2H, br), 3.45–3.75 (4H, m), 4.74 (1H, Jabq. 16.7 Hz, 54.2 Hz), 5.01 (1H, Jabq. 16.7 Hz, 54.2 Hz), 5.33 (1H, d, 8.3 Hz), 7.0–7.7 (12H, m), 8.11 (1H, s), 9.47 (1H, s), 12.0 (1H, s); IR (Nujol, $cm^{-1}$): 3350, 1720, 1650; Mass (APCI): 675 ($M^+$+1); mp: 193.0–203.4° C.

EXAMPLE 89

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-(3-methanesulfonylaminosulfonylphenyl)urea was obtained in a similar manner to that of Example 52.

NMR (DMSO-$d_6$, δ): 1.5–1.7 (8H, br), 2.01 (2H, br), 2.73 (3H, s), 3.46–3.66 (4H, m), 4.75 (1H, Jabq. 16.8 Hz, 50.9 Hz), 5.01 (1H, Jabq. 16.8 Hz, 50.9 Hz), 5.32 (1H, d, 8.4 Hz), 7.2–7.7 (12H, m), 9.22 (1H, s); IR (Nujol, $cm^{-1}$): 3320, 1630; Mass (FAB): 711 ($M^+$+1); mp: >250° C.

EXAMPLE 90

A mixture of N-[(3RS)-1-(3-azabicyclo[3.2.2]non-3-yl)-carbonylmethyl- 2,3-dihydro-5-(2-fluorophenyl)-2-oxo-1H-1,4-benzodiazepin-3-yl]-N'-(3-formylphenyl)urea, hydroxyamine hydrochloride and triethylamine in tetrahydrofuran was stirred at room temperature overnight. Ethyl acetate and water were added to the reaction mixture, and the organic layer was separated, washed with water and brine, dried over magnesium sulfate, and-evaporated to dryness. The white powder was washed with isopropyl ether to afford N-[(3RS)-1-(3-azabicyclo[3.2.2]non-3-yl) carbonylmethyl-2,3-(dihydro-5-(2-fluorophenyl)-2-oxo-1H-1,4-benzodiazepin-3-yl]-N'-(3-hydroxyiminomethylphenyl)urea.

NMR (DMSO-$d_6$, δ): 1.5–1.7 (8H, br), 2.01 (2H, br), 3.45–3.78 (4H, m), 4.73 (1H, Jabq. 16.7 Hz, 57.6 Hz), 5.01 (1H, Jabq. 16.7 Hz, 57.6 Hz), 5.33 (1H, d, 8.4 Hz), 7.1–7.7 (12H, m), 8.06 (1H, s), 9.14 (1H, s), 11.20 (1H, s); IR (Nujol, $cm^{-1}$): 3270, 1680, 1640, 1600; Mass (APCI): 597 ($M^+$+1); mp: 194.0–197.2° C.

EXAMPLE 91

A mixture of N-[(3RS)-1-(3-azabicyclo[3.2.2]non-3-yl)-carbonylmethyl-2,3-dihydro-5-(2-fluorophenyl)-2-oxo-1H-1,4-benzodiazepin-3-yl]-N'-[3-(ethoxycarbonylmethoxy) phenyl]urea and 0.1N NaOH in tetrahydrofuran was stirred at room temperature for 6 hours. 1N HCl was added to the reaction mixture. Ethyl acetate and water were added to the reaction mixture, and the organic layer was removed, washed with water and brine, and dried over magnesium sulfate. The solution was evaporated to dryness and washed with isopropyl ether and diethyl ether to afford N-[(3RS)-1-(3-azabicyclo[3.2.2]non-3-yl)carbonylmethyl-2,3-dihydro-5-(2-fluorophenyl)-2-oxo-1H-1,4-benzodiazepin-3-yl]-N'-(3-carboxymethoxyphenyl)urea.

NMR (DMSO-$d_6$, δ): 1.5–1.7 (8H, br), 1.99 (2H, br), 3.4–3.8 (4H, brm), 4.59 (2H, s), 4.72 (1H, Jabq. 16.8 Hz, 56.6 Hz), 5.01 (1H, Jabq. 16.8 Hz, 56.6 Hz), 5.32 (1H, d, 8.4 Hz), 6.4–7.7 (12H, m), 9.08 (1H, s); IR (Nujol, $cm^{-1}$): 3300, 1750, 1650, 1605; Mass (APCI): 628 ($M^+$+1); up: 227.2° C. (dec.)

EXAMPLE 92

A mixture of N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-(3-hydroxyphenyl)urea, potassium carbonate and ethyl bromoacetate in dimethylformamide was stirred at room temperature for 4 hours. Ethyl acetate and water were added to the reaction mixture. The organic layer was separated, washed with water and brine, and dried over magnesium sulfate. The organic solvent was evaporated to dryness, and washed with isopropyl ether and vacuumed to afford N-[(3RS)-1-(3- azabicyclo[3.2.2]non-3-yl)carbonylmethyl-2,3-dihydro-5-(2-fluorophenyl)-2-oxo-1H-1,4-benzodiazepin-3-yl]-N'-[3-(ethoxycarbonylmethoxy)phenyl]urea.

NMR (DMSO-$d_6$, δ): 1.19 (3H, t, 7.1 Hz), 1.5–1.7 (8H, m), 2.01 (2H, br), 3.46–3.78 (4H, m), 4.15 (2H, q, 7.1 Hz), 4.70 (2H, s), 4.73 (1H, Jabq, 16.8 Hz, 57.4 Hz), 5.01 (1H, Jabq, 16.8 Hz, 57.4 Hz), 5.32 (1H, d, 8.5 Hz), 6.4–7.7 (12H, m), 9.08 (1H, s); IR (Nujol, $cm^{-1}$): 3300, 1750, 1650, 1603; Mass (APCI): 656 ($M^+$31); mp: 156.2°–158.2° C.

EXAMPLE 93

A mixture of N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-(3-cyanophenyl)urea, hydroxyamie hydrochloride and triethylamine in dimethylsulfoxide was stirred at 70° C. overnight. Ethyl acetate and water weretadded to the reaction mixture and the organic layer was separated, washed with water and brion, dried over magnesium sulfate, and evaporated to dryness. The crude powder was purified by column chromatography on silica gel to afford N-[(3RS)-1-(3-azabicyclol[3.2.2]non-3-yl)carbonylmethyl-2,3-dihydro-5-(2-fluorophenyl)-2-oxo-1H-1,4-benzodiazepin-3-yl]-N'-{3-[1-amino-1-hydroxyiminomethyl]-phenyl}urea.

NMR (DMSO-$d_6$, δ): 1.5–1.8 (8H, br), 2.00 (2H, br), 3.44–3.78 (4H, m), 4.72 (1H, Jabq, 16.8 Hz, 58.0 Hz), 5.01 (1H, Jabq, 16.8 Hz, 58.0 Hz), 5.33 (1H, d, 8.4 Hz), 5.71 (2H, br s), 7.0–7.7 (12H, m), 9.08 (1H, s), 9.57 (1H, s); IR (Nujol, $cm^{-1}$): 3300, 1650; Mass (APCI): 612 ($M^+$+1); mp: 203.3°–209.9° C.

EXAMPLE 94

N-[1-(3-azabicyclo[3.2.2]non-3-yl)carbonylmethyl-2,3-dihydro-5-(2-fluorophenyl)-2-oxo-1H-1,4-benzodiazepin-3-yl]-N'-(3-methoxycarbonylphenyl)urea was obtained in a similar manner to that of Example 13-7.

IR (Nujol, $cm^{-1}$): 3340, 3250, 1718, 1691, 1675, 1638, 1604, 1531, 1485, 1375, 1326, 1295, 1230, 1105, 1020, 760, 750; $^1$H-NMR (DMSO-$d_6$, δ): 1.45–1.8 (8H, m), 1.95–2.1 (2H, m), 3.45–3.9 (4H, m), 3.83 (3H, s), 4.88 (2H, ABq, J=16.8 Hz, 57.1 Hz), 5.33 (1H, d, J=8.3 Hz), 7.2–7.7 (12H, m), 8.15 (1H, s), 9.31 (1H, s); APCI-MS (DMF) (m/z): 612 ($M^+$+1)

EXAMPLE 95

A mixture of N-[1-(3-azabicyclo[3.2.2]non-3-yl) carbonylmethyl-2,3-dihydro-5-(2-fluorophenyl)-2-oxo-1H-1,4-benzodiazepin-3-yl]-N'-(3-methoxycarbonylphenyl) urea (312.5 mg) and 0.1N sodium hydroxide (7.7 ml, 1.5 eq. mol) in tetrahydrofuran (20 ml) was refluxed under stirring for 7 hours. After removal of the tetrahydrofuran, the residual aqueous mixture was extracted with ethyl acetate. After the separated aqueous layer was washed with ethyl acetate, it was acidified with diluted hydrochloric acid. The resultant precipitates were collected by filtration, washed with water and dried under reduced pressure to afford N-[1-(3-azabicyclo[3.2.2]non-3-yl)carbonylmethyl-2,3-dihydro-5-(2-fluorophenyl)-2-oxo-1H-1,4-benzodiazepin-3-yl]-N'-(3-carboxyphenyl)urea (0.19 g, 62.2%) as a white crystalline powder.

mp: 200.5°–205.5° C. (dec.) IR (Nujol, $cm^{-1}$): 3350, 1700, 1685, 1670, 1645, 1605, 1550, 1374, 1320, 1270, 1214, 754; $^1$H-NMR (DMSO-$d_6$, δ) 1.45–1.85 (8H, m), 1.95–2.1 (2H, m), 3.4–3.8 (4H, m), 4.88 (2H, ABq, J=16.8 Hz, 57.4 Hz), 5.34 (1H, d, J=8.4 Hz), 7.2–7.7 (12H, m), 8.06 (1H, s), 9.26 (1H, s), 12.89 (1H, s); APCI-MS (DMF) (m/z): 599 ($M^+$+2), 598 ($M^+$+1)

EXAMPLE 96-1

N-[(3R)-1-(3-azabicyclo[3.2.2]non-3-yl)carbonylmethyl-2,3-dihydro-5-(2-fluorophenyl)-2-oxo-1H-1,4-benzodiazepin-3-yl]-N'-(3-t-butoxycarbonylphenyl)urea was obtained in a similar manner to that of Example 13-7.

EXAMPLE 96-2

To a solution of the amorphous mass obtained above (Example 96-1) (0.26 g) in methylene chloride (4 ml) was added trifluoroacetic acid (1.0 ml) under ice-bath cooling and stirring. The mixture was stirred under the same condition for 0.5 h and at ambient temperature for 0.5 h. After removal of methylene chloride in vacuo, to the residue was added water and extracted with ethyl acetate. The extract was washed with water twice and dried over magnesium sulfate. Removal of the solvent in vacuo gave an orange oil (0.40 g), which was subjected to column chromatography on silica gel eluting with a mixture of chloroform and methanol (20:1). The fractions containing the desired product were combined and evaporated to afford N-[(3R)-1-(3-azabicyclo[3.2.2]non-3-yl)carbonylmethyl-2,3-dihydro-5-(2-fluorophenyl)-2-oxo-1H-1,4-benzodiazepin-3-yl]-N'-(3-carboxyphenyl)urea (0.25 g) as an amorphous mass, which was triturated in diisopropyl ether to afford a cyrstalline powder and collected by filtration (174.2 mg, 84.5% yield).

mp: 231°–232.5° C. (dec.) $[\alpha]_D^{28}$=32.1° (c=1.0, DMF); IR (Nujol, $cm^{-1}$): 3360, 3270, 3150, 1680, 1652, 1608, 1545, 1374, 1321, 1261, 1230, 1210, 1102, 1000, 940, 752; $^1$H-NMR (DMSO-$d_6$, δ): 1.45–1.85 (8H, m), 4.88 (2H, ABq, J=16.8 Hz, 57.4 Hz), 5.34 (1H, d, J=8.4 Hz), 7.2–7.7 (12H, m), 8.06 (1H, s), 9.26 (1H, s), 12.89 (1H, s); APCI-MS (DMF) (m/z): 598 ($M^+$+1)

EXAMPLE 97-1

N-[(3S)-1-[(3-azabicyclo[3.2.2]non-3-yl) carbonylmethyl-2,3-dihydro-5-(2-fluorophenyl)-2-oxo-1H-1,4-benzodiazepin-3-yl]-N'-(3-t--butoxycarbonylphenyl) urea was obtained in a similar manner to that of Example 103.

EXAMPLE 97-2

N-[(3S)-1-(3-azabicyclo[3.2.2]non-3-yl)carbonylmethyl-2,3-dihydro-5-(2-fluorophenyl)-2-oxo-1H-1,4-benzodiazepin-3-yl]-N-(3-carboxyphenyl)urea was obtained in a similar manner to that of Example 96-2.

mp: 230°–232° C. (dec.); $[\alpha]_D^{28}$=–31.5° (c=1.0, DMF); IR (Nujol, $cm^{-1}$): 3360, 3300, 3150, 1680, 1652, 1608, 1544, 1374, 1325, 1260, 1230 (sh), 1210, 1105, 1000, 942, 752; $^1$H-NMR (DMSO-$d_6$, δ): 145–1.85 (8H, m), 1.95 -2.1 (2H, m), 3.4–3.8 (4H, m), 4.88 (211, ABq, J=16.8 Hz, 57.4 Hz), 5.34 (1H, d, J=8.4 Hz), 7.2–7.7 (12H, m), 8.06 (1H, s), 9.26 (1H, s), 12.90 (1H, s); APCI-MS (DMF)(m/z): 598 ($M^+$+1)

EXAMPLE 98-1

N-[1-(3-azabicyclo[3.2.2]non-3-yl)carbonylmethyl-2,3-dihydro-5-(2-fluorophenyl)-2-oxo-1H-1,4-benzodiazepin-3-yl]-N'-[3-(methoxycarbonylmethyl)phenyl]urea was obtained in a similar manner to that of Example 13-7.

EXAMPLE 98-2

N-[1-(3-azabicyclo[3.2.2]non-3-yl)carbonylmethyl-2,3-dihydro-5-(2-fluorophenyl)-2-oxo-1H-1,4-benzodiazepin- 3-yl]-N'-[3-(carboxymethyl)phenylurea was obtained in a similar manner to that of Example 95.

mp: 170°–175° C. (dec.) $^1$H-NMR (DMSO-$d_6$, δ): 1.45–1.8 (8H, m), 1.95–2.1 (2H, m), 3.4–3.8 (6H, m), 4.87 (2H, ABq, J=16.7 Hz, 56.1 Hz), 5.32 (1H, d, J=8.4 Hz), 6.82 (1H, d, J=7.2 Hz), 7.1–7.7 (12H, m), 9.05 (1H, s); APCI-MS (DMF)(m/z): 612 ($M^+$+1); IR (Nujol, $cm^{-1}$): 3300, 1700, 1680, 1650, 1615, 1555, 1540, 1480, 1372, 1325, 1265, 1210, 1010, 810, 760

EXAMPLE 99

A mixture of N-[1-(3-azabicyclo[3.2.2]non-3-yl) carbonyl-methyl-2,3-dihydro-5-(2-fluorophenyl)-2-oxo-1H-1,4-benzodiazepin-3-yl]-N'-(3-cyanophenyl)urea (491.6 mg), sodium azide (331.4 mg, 6 eq. mol) and triethylamine hydrochloride (772.2 mg, 6.6 eq. mol) in N-methylpyrrolidone (10 ml) was heated at 120° C. under stirring for 8.5 hours. The reaction mixture was poured into water and acidified with 6N hydrochloric acid. The mixture was extracted with ethyl acetate twice and the extract was washed with water and dried over magnesium sulfate. Removal of the solvent gave an oil (0.36 g), which was subjected to column chromatography on silica gel eluting with a mixture of chloroform and methanol (20:1). The fractions containing the desired product were combined and evaporated to give N-[1-(3-azabicyclo[3.2.2]non-3-yl) carbonylmethyl-2,3-dihydro-5-(2-fluorophenyl)-2-oxo-1H-1,4-benzodiazepin-3-yl]-N'-[3-(tetrazol-5-yl)phenyl]urea (0.13 g, 24.6%) as an oil, which crystallized on standing.

mp: 215°–218° C. (dec.); IR (Nujol, $cm^{-1}$): 3350, 1655, 1620, 1372, 1212, 745; $^1$H-NMR (DMS0-$d_6$, δ): 1.45–1.8 (8H, m), 1.95–2.1 (2H, m), 3.2–3.85 (4H, m), 4.88 (2H, ABq, J=16.8 Hz, 57.3 Hz), 5.36 (1H, d, J=8.3 Hz), 7.2–7.7 (13H, m), 8.21 (1H, s), 9.34 (1H, s)

EXAMPLE 100

N-[(3R)-1-(3-azabicyclo[3.2.2]non-3-yl)carbonylmethyl-2,3-dihydro-5-(2-fluorophenyl)-2-oxo-1H-1,4-benzodiazepin-3-yl]-N'-[3-(tetrazol-5-yl)phenyl]urea was obtained in a similar manner to that of Example 13-7.

mp: 207°–210° C. (dec.); $[\alpha]_D^{25}$=27.8° (c=1.0, DMF); IR (Nujol, $cm^{-1}$): 3300, 2750–2300, 1680 (sh), 1650, 1610 (sh), 1545, 1374, 1325, 1210, 1100, 1010, 750; $^1$H-NMR (DMSO-$d_6$,δ) 1.45–1.8 (8H, m), 1.95–2.1 (2H, m), 3.2–3.8 (4H, m), 4.88 (2H, ABq, J=16.8 Hz, 57.3 Hz), 5.36 (1H, d, J=8.3 Hz), 7.2–7.7 (13H, m), 8.20 (1H, s), 9.33 (1H, s); APCI-MS (DMF)(m/z): 6.22 ($M^+$+1)

EXAMPLE 101

N-[(3S)-1-(3-azabicyclo[3.2.2]non-3-yl)carbonylmethyl-2,3-dihydro-5-(2-fluorophenyl)-2-oxo-1H-1,4-benzodiazepin-3-yl]-N'-[3-[(tetrazol-5-yl)phenyl]urea was obtained in a similar manner to that of Example 103.

mp: 208°–211° C. (dec.); $[\alpha]^D_{25}$=27.5° (c=1.0, DMF); IR (Nujol, $cm^{-1}$): 3300, 2750–2,300, 1680 (sh), 1650, 1610 (sh), 1567, 1535, 1480, 1375, 1325, 1212, 1100, 1010, 750; $^1$H-NMR (DMSO-$d_6$, δ): 1.45–1.8 (8H, m), 1.95–2.1 (2H, m), 3.2–3.8 (4H, m), 4.88 (2H, ABq, J=16.8 Hz, 57.3 Hz), 5.36 (1H, d, J=8.3 Hz), 7.2–7.7 (13H, m), 8.20 (1H, s), 9.33 (1H, s); APCI-MS (DMF)(m/z): 622 ($M^+$+1)

EXAMPLE 102

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-[3-(tetrazol-5-yl)methylphenyl] urea was obtained in a similar manner to that of Example 13-7.

mp: 192°–196° C. (dec.); IR (Nujol, $cm^{-1}$): 3375, 3325, 1690 (sh), 1650, 1615, 1550, 1490, 1375, 1320, 1210, 1100, 1050, 1000, 808, 760; $^1$H-NMR (DMSO-$d_6$, δ) 1.45–1.8 (8H, m), 1.95–2.1 (2H, m), 3.45–4.8 (4H, m), 4.22 (2H, s), 4.86 (2H, ABq, J=16.7 Hz, 56.8 Hz), 5.31 (1H, d, J=8.4Hz), 6.82 (1H, d, J=7.1 Hz), 7.15–7.70 (13H, m), 9.08 (1H, s); APCI-MS (DMF)(m/z): 636 ($M^+$+1)

EXAMPLE 103

To a solution of N-tert-butoxycarbonyl-L-tryptophane salt of (3S)-3-amino-1-[(3-azabicyclo[3.2.2]non-3-yl) carbonylmethyl]-2,3-dihydro-5-(2-fluorophenyl)-1H-1,4-benzodiazepin-2-one (369.6 mg, 0.5 mmol) and triethylamine (126.5 mg, 1.25 mmol) in dimelthylformamide (5 ml) was added 4-nitrophenyl [3-(tetrazol-5-yl) methylphenyl]carbamate (204.2 mg, 0.6 mmol) under stirring at ambient temperature. The mixture was stirred for 4 hours under the same condition. The reaction mixture was poured into water and acidified with 1N-HCl. The mixture was extracted with ethyl acetate twice. The organic extract was washed with water and brine successively. After drying over $MgSO_4$, the solvent was removed in vacuo to give an oil (0.58 g), which was subjected to column chromatography on silica gel eluting with a mixture of chloroform and methanol (50:1) to afford N-[(3S)-1-(3-azabicyclo[3.2.2] non-3-yl)carbonylmethyl-2,3-dihydro-5-(2-fluorophenyl)-2-oxo-1H-1,4-benzodiazepin-3-yl]-N'-[3-(tetrazol-5-yl) methylphenyl]urea (212.2 mg) as an amorphous mass. This was triturated in diisopropyl ether to give a colorless powder (193.0 mg, 60.7% yield).

mp: 178.5°–185° C. (dec.); $[\alpha]_D^{23}$=38.57° (c=0.56, DMF); $^1$H-NMR (DMSO-$d_6$, δ): 1.45–1.8 (8H, m), 2.01 (2H, m), 3.45–3.75 (4H, m), 4.22 (2H, s), 4.86 (2H, d,d, J=16.7 Hz, 56.8 Hz), 5.31 (1H, d, J=8.4 Hz), 6.82 (1H, d, J=7.1 Hz), 7.15–7.70 (13H, m), 9.08 (1H, s); APCI-MS (DMF): 636 ($M^+$+1)

EXAMPLE 104

N-[(3R)-1-(3-azabicyclo[3.2.2]non-3-yl)carbonylmethyl-2,3-dihydro-5-(2-fluorophenyl)-2-oxo-1H-1,4-benzodiazepin-3-yl]-N'-]3-(tetrazol-5-yl)methylphenyl]urea was obtained in a similar manner to that of Example 103.

mp: 170°–174° C. (dec.); $[\alpha]_D^{23}$=37.14° (c=0.56, DMF); $^1$H-NMR (DMSO-$d_6$, δ): 1.45–1.8 (8H, m), 2.01 (2H, m), 3.45–3.75 (4H, m), 4.23 (2H, s), 4.87 (2H, d,d, J=16.7 Hz, 56.8Hz), 5.31 (1H, d, J=8.4 Hz), 6.82 (1H, d, J=7.1 Hz), 7.15–7.70 (13H, m), 9.08 (1H, s); APCI-MS (DMF): 636 ($M^+$+1)

EXAMPLE 105

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-]3--(benzyloxycarbonylmethylaminocarbonyl)phenyl]urea was obtained in a similar manner to that of Example13-7. $^1$H-NMR (DMSO-$d_6$, δ): 1.45–1.8 (8H, m), 1.95–2.1 (2H, br, s), 3.4–3.8 (4H, m), 4.05 (2H, d, J=5.7 Hz), 4.87 (2H, ABq, J=16.6 Hz, 57.4 Hz), 5.16 (2H, s), 5.34 (1H, d, J=8.4 Hz), 7.2–7.7 (17H, m), 7.87 (1H, s), 8.90 (1H, t, J=5.7 Hz), 9.21 (1H, s)

EXAMPLE 106

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl-N'-[3-

(carboxymethylaminocarbonyl)phenyl]urea was obtained in a similar manner to that of Example 95.

mp: 199°–204° C. (dec.); IR (Nujol, $cm^{-1}$): 3325, 2800–2300, 1690 (sh), 1655, 1638, 1545, 1485, 1378, 1325, 1214, 1010, 808, 750; $^1$-H-NMR (DMSO-$d_6$, δ) 1.45–1.8 (8H, m), 1.95–2.1 (2H, br, s), 3.4–3.8 (4H, m), 3.89 (2H, d, J=5.7 Hz), 4.88 (2H, ABq, J=16.7 Hz, 57.3 Hz), 5.34 (1H, d, J=8.4 Hz), 7.2–7.7.(12H, m), 7.85 (1H, s), 8.75 (1H, t, J=5.7 Hz), 9.21 (1H, s), 12.59 (1H, br, s) APCI-MS (DMF) (m/z): 655 ($M^+$+1)

EXAMPLE 107-1

N-[1-(3-azabicyclo13.2.2]non-3-yl)carbonylmethyl-2,3-dihydro-5-(2-fluorophenyl)-2-oxo-1H-1,4-benzodiazepin-3-yl]-N'-[3-[(1L)1-benzyloxycarbonylethyl)aminocarbonyl] -phenyl]urea was obtained in a similar manner to that of Example 103.

EXAMPLE 107-2

The amorphous mass obtained above (Example 107-1) and 1N-aqueous sodium hydroxide solution (2 eq. mol) in tetrahydrofuran were stirred at ambient temperature for 3 hours. Tetrahydrofuran was removed in vacuo and to the residual aqueous mixture was added additional water. The aqueous mixture was acidified with diluted aqueous hydrochloric acid and extracted with ethyl acetate twice. The combined organic extract was washed with water and dried over magnesium sulfate. Removal of the solvent gave a crystalline powder, which was subjected to column chromatography on silica gel eluting with a mixture of chloroform and methanol (10:1). The desired fractions were combined and evaporated to dryness to afford a mixture of diastereoisomers of N-[1-(3-azabicyclo[3.2.2]non-3-yl) carbonylmethyl-2,3-dihydro-5-(2-fluorophenyl)-2-oxo-1H-1,4-benzodiazepin-3-yl]-N'-[3-[(1L)-1-carboxyethyl) aminocarbonyl]phenyl]urea (452.0 mg, 67.6% yeild) as a crystalline powder.

mp: 265°–268° C. (dec.); $^1$H-NMR (DMSO-$d_6$, δ): 1.33 (3H, d, J=7.0 Hz), 1.45–1.8 (8H, m), 1.95–2.1 (2H, m), 3.4–3.8 (4H, m), 4.17 (1H, J=7 Hz), 4.85 (2H, d, d, J=16.7 Hz, 56.5 Hz), 5.34 (1H, d, 8.4 Hz), 7.2–7.1 (12H, m), 7.82 (1H, s), 7.96 (1H, d, J=8.4 Hz), 9.50 (1H, d, J=9.6Hz); APCI-MS: 669 ($M^+$+1)

EXAMPLE 108

A diastereomeric mixture of N-[(3RS)-1-(3-azabicyclo-[3.2.2]non-3-yl)carbonylmethyl-2,3-dihydro-5-(2-fluorophenyl)-2-oxo-1H-1,4-benzodiazepin-3-yl]-N'-[3-((1L)-1,3-diethoxy-carbonylpropylaminocarbonyl)phenyl] urea was obtained in a similar manner to that of Example 13-7. $^1$H-NMR ($CDCl_3$, δ) 1.14–1.31 (6H, m), 1.5–2.5 (14H, m), 3.35–4.25 (8H, m), 4.6–4.8 (1H, m), 4.72 & 4.78 (2H, each ABq, J=16.2 Hz, 156 Hz), 5.72 & 5.75 (1H, each d, J=8.7 Hz), 6.9–8.0 (15H, m) FAB-MS ($CHCl_3$)(m/z): 783.4 ($M^+$+1)

EXAMPLE 109

N-[(3RS)-1-(3-azabicyclo[3.2.2]non-3-yl) carbonylmethyl-2,3-dihydro-5-(2-fluorophenyl)-2-oxo-1H-1,4-benzodiazepin-3-yl]-N'-]3-(1,3-dicarboxypropylaminocarbonyl)phenyl]urea was obtained in a similar manner to that of Example 95.

mp: 220°–223.5° C. (dec.); $^1$H-NMR (DMSO-$d_6$, δ): 1.45–1.8 (8H, m), 1.9–2.1 (4H, m), 2.25–2.35 (2H, m), 3.4–3.7 (4H, m), 4.29 (1H, br, q), 4.87 (2H, ABq, J=16.6 Hz, 55.4 Hz), 5.34 (1H, d, J=8.4 Hz), 7.2–7.66 (12H, m), 7.79 (1H, s), 8.16 (1H, br, d, J=8.4 Hz), 9.26 (1H, s); FAB-MS (DMF)(m/z): 727.6 ($M^+$+1)

EXAMPLE 110

A mixture of N-[(3RS)-1-(3-azabicyclo[3.2.2]non-3-yl)-carbonylmethyl-2,3-dihydro-5-(2-fluorophenyl)-2-oxo-1H-1,4-benzodiazepin-3-yl]-N'-(3-aminophenyl)urea (200 mg) and acetic anhydride (2.0 ml) in dichloromethane (2.0 ml) was stirred at room temperature for four days. The reaction mixture was evaporated to afford a yellow crude powder. The powder was washed with isopropyl ether to afford N-[(3RS)-1-(3-azabicyclo[3.2.2]-non-3-yl)carbonylmethyl-2,3-dihydro-5-(2-fluorophenyl)-2-oxo-1H-1,4-benzodiazepin-3-yl]-N'-[3-(N-acetylamino)phenyl]urea (212 mg).

mp: 207.4°–215.4° C.; NMR (DMSO-$d_6$, δ): 1.5–1.8 (8H, br), 2.02 (5H, br s), 3.4–3.8 (4H, m), 4.72 (1H, dd, 16.7 Hz, 57.3 Hz), 5.01 (1H, dd, 16.7 Hz, 57.3 Hz), 5.32 (1H, d, 8.5 Hz), 7.1–7.7 (12H, m) 9.06 (1H, s), 9.87 (1H, s); Mass (APCI): 6H($M^+$+1); IR (Nujol, $cm^{-1}$) 3330, 1660, 1618

We claim:

1. A compound of the formula:

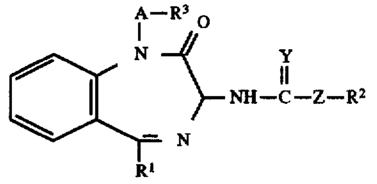

(I)

wherein $R^1$ is aryl or $C_3$–$C_8$ cycloalkyl, each of which may have one or more suitable substituent(s), $R^2$ is $C_3$–$C_8$ cycloalkyl, aryl, indanyl or a heterobicyclic group other than 2-indolyl, each of which may have one or more suitable substituent(s), A is lower alkylene, $R^3$ is a heterocyclic group selected from the group consisting of tetrahydrofuryl, dioxolanyl, furyl, thienyl, isoxazolyl, pyridyl, benzimidazolyl, benzothiazolyl,benzoxazolyl, benzopyranyl, quinolyl, isoquinolyl, tetrahydroisoquinolyl, benzothienyl and benzofuryl, each of which may have one or more suitable substituent(s); or a group of the formula: —X—$R^4$

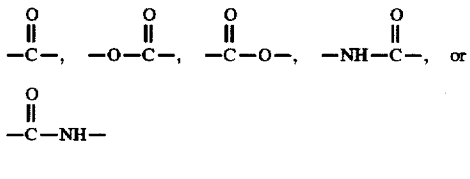

and $R^4$ is thiomorpholinyl; pyridyl; a bridged heterocyclic group containing at least one nitrogen atom, which may have one or more suitable substituent(s); or a bridged cyclic-hydrocarbon group), Y is O or S, and —Z— is direct single bond between carbon and $R^2$, or

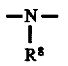

(in which $R^8$ is hydrogen or lower alkyl), or a pharmaceutically acceptable salt thereof.

2. A compound of claim 1, wherein $R^1$ is aryl which may have one or more halogen (s); cyclohexyl; cyclopentyl; or cycloheptyl;

$R^2$ is cyclohexyl; indanyl; or aryl or heterobicyclic group other than 2-indolyl, each of which may have one or more substituent(s) selected from the group consisting of lower alkyl; lower alkylthio; halogen; trihalo(lower)alkyl; lower alkoxy; cyclo(lower)alkyl (lower)alkoxy; lower alkylthio(lower)alkoxy; lower alkoxy(lower)alkyl; hydroxy; lower alkanoyl; lower alkylthio(lower)alkoxycarbonyl; lower alkoxyimino (lower)alkyl; lower alkoxycarbonyl(lower)alkenyl; oxo; amino; lower alkanoylamino; lower alkoxycarbonyl; lower alkoxycarbonyl(lower)alkyl; cyano; nitro; hydroxy(lower)alkyl; trihalo(lower)alkoxy; carbamoyl which may be substituted with one or two substituent(s) selected from the group consisting of lower alkyl, tetrazolyl, mono or di carboxy(lower) alkyl, mono or di (lower-alkoxycarbonyl)(lower) alkyl and phenyl(lower)alkoxycarbonyl(lower)alkyl; dihydroxyboryl; sulfo(lower)alkyl; sulfo; sulfamoyl whcih may have one or more substituent(s) selected from the group consisting of lower alkanoyl, lower alkanesulfonyl, phenyl and lower alkyl; oxo-dihydropyridazinyl; oxo-dihydrooxadiazolyl; tetrazolyl; tetrazolyl(lower)alkyl; carboxy; carboxy (lower)alkyl; carboxy(lower)alkoxy; hydroxyimino (lower)alkyl; 1-amino-1-(hydroxyimino)methyl; and lower alkoxy-carbonyl(lower)alkoxy;

A is lower alkylene;

$R^3$ is a heterocyclic group selected from the group consisting of tetrahydrofuryl, dioxolanyl, furyl, thienyl, isoxazolyl, pyridyl, benzimidazolyl, benzothiazolyl, benzoxazolyl, benzopyranyl, quinolyl, isoquinolyl, tetrahydroisoquinolyl, benzothienyl and benzofuryl, each of which may have one or more substituent(s) selected from the group consisting of lower alkyl, oxo, lower alkoxy, lower alkanoyl, halogen, pyrrolidinylcarbonyl, oxy, lower alkoxycarbonyl, carboxy, carbamoyl, moro or di {(lower)alkyl}-amino(lower)alkylcarbamoyl and bridged N-containing heterocyclic carbonyl; or a group of the formula: —X—$R^4$

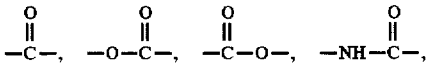

or

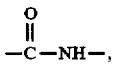

and $R^4$ is thiomorpholinyl; pyridyl; a bridged heterocyclic group containing at least one nitrogen atom, which may have one or more substituent(s) selected from the group consisting of lower alkyl and phenyl(lower)alkyl;

or a bridged cyclic-hydrocarbon group);

Y is O or S, and

—Z— is direct single bond between carbon and $R^2$, or

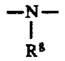

(in which $R^8$ is hydrogen or lower alkyl), or a pharmaceutically acceptable salt thereof.

3. A compound of claim 1, wherein $R^1$ is phenyl which may have one or more halogen(s); cyclohexyl; cyclopentyl; or cycloheptyl;

$R^2$ is cyclohexyl; indanyl; or phenyl, benzothiadiazolyl, benzodioxanyl, indazolyl, tetrahydroquinolyl, methylenedioxyphenyl or indolyl other than 2-indolyl, each of which may have one or more substituent(s) selected from the group consisting of lower alkyl; lower alkylthio; halogen; trihalo(lower)alkyl; lower alkoxy; cyclo(lower)alkyl (lower)alkoxy; lower alkylthio(lower)alkoxy; lower alkoxy(lower)alkyl; hydroxy; lower alkanoyl; lower alkylthio(lower)alkoxycarbonyl; lower alkoxyimino (lower)alkyl; lower alkoxycarbonyl(lower)alkenyl; oxo; amino; lower alkanoylamino; lower alkoxycarbonyl; lower alkoxycarbonyl(lower)alkyl; cyano; nitro; hydroxy(lower)alkyl; trihalo(lower)alkoxy; carbamoyl which may be substituted with one or two substituents selected from the group consisting of lower alkyl, tetrazolyl, mono or di carboxy(lower) alkyl, mono or di (lower alkoxycarbonyl)(lower) alkyl and phenyl(lower)alkoxycarbonyl(lower)alkyl; dihydroxyboryl; sulfo(lower)alkyl; sulfo; sulfamoyl whcih may have one or more substituent(s) selected from the group consisting of lower alkanoyl, lower alkanesulfonyl, phenyl and lower alkyl; oxo-dihydropyridazinyl; oxo-dihydrooxadiazolyl; tetrazolyl; tetrazolyl(lower)alkyl; carboxy; carboxy (lower)alkyl; carboxy(lower)alkoxy; hydroxyimino (lower)alkyl; 1-amino-1-(hydroxyimino)methyl; and lower alkoxycarbonyl(lower)alkoxy;

A is methylene or ethylene;

$R^3$ is a heterocyclic group selected from the group consisting of tetrahydrofuryl, dioxolanyl, furyl, thienyl, isoxazolyl, pyridyl, benzimidazolyl, benzothiazolyl, benzoxazolyl, benzopyranyl, quinolyl, isoquinolyl, tetrahydroisoquinolyl, benzothienyl and benzofuryl, each of which may have one or more substituent(s) selected from the group consisting of lower alkyl, oxo, lower alkoxy, lower alkanoyl, halogen, pyrrolidinylcarbonyl, oxy, lower alkoxycarbonyl, carboxy, carbamoyl, moro or di {(lower)alkyl}-amino(lower)alkylcarbamoyl and bridged N-containing heterocyclic carbonyl; or a group of the formula: —X—$R^4$

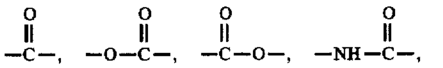

or

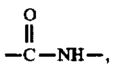

and $R^4$ is thiomorpholinyl; pyridyl; 3-azabicyclo [3.2.2]non-3-yl, 6-azabicyclo[3.2.1]oct-6-yl, 2-azabicyclo[2.2.1]hept-5-en-2-yl, 2-azabicyclo [2.2.1]hept-2-yl, 2,5-diazabicyclo[2.2.1]hept-2-yl, 3,8-diazabicyclo[3.2.1]oct-3-yl or 2-azatricyclo [4.3.1.1$^{4,8}$]undec-2-yl, each of which may have one or more substituent(s) selected from the group consisting of lower alkyl and phenyl(lower)alkyl; or adamantyl);

Y is O or S, and

—Z— is direct single bond between carbon and $R^2$, or

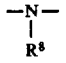

(in which $R^8$ is hydrogen or methyl), or a pharmaceutically acceptable salt thereof.

4. A compound of claim 1, wherein $R^1$ is phenyl which may have one or more fluorine(s); cyclohexyl; cyclopentyl; or cycloheptyl;

$R^2$ is cyclohexyl; indanyl; or phenyl, benzothiadiazolyl, benzodioxanyl, indazolyl, tetrahydroquinolyl, methylenedioxyphenyl or indolyl, each of which may have one or more substituent(s) selected from the group consisting of methyl, ethyl, methylthio, fluorine, chlorine, bromine, trifluoromethyl, methoxy, cyclopropylmethoxy, methylthioethoxy, methoxyethyl, hydroxy, acetyl, methylthioethoxycarbonyl, methoxyiminomethyl, methoxycarbonylvinyl, phenylsulfamoyl, dimethylsulfamoyl, trifluoromethoxy, ethoxy, formyl, hydroxymethyl, amino, acetylamino, carbamoyl, methylcarbamoyl, oxo-dihydropyridazinyl, dihydroxyboryl, sulfomethyl, sulfo, sulfoethyl, terazolylcarbamoyl, carboxyethyl, oxo-dihydrooxadiazolyl, acetylsulfamoyl, methanesulfonylsulfamoyl, hydroxyiminomethyl, carboxymethoxy, ethoxycarbonylmethoxy, 1-amino-1-(hydroxyimino)methyl, methoxycarbonyl, carboxy, methoxycarbonylmethyl, carboxymethyl, tetrazolyl, tetrazolylmethyl, benzyloxycarbonylmethylcarbamoyl, carboxymethylcarbamoyl, benzyloxycarbonylethylcarbamoyl, carboxyethylcarbamoyl, di(ethoxycarbonyl)propylcarbamoyl, di(carboxy)propylcarbamoyl, sulfamoyl, cyano, nitro, and t-butoxycarbonyl;

A is methylene or ethylene;

$R^3$ is a heterocyclic group selected from the group consisting of tetrahydrofuryl, dioxolanyl, furyl, thienyl, isoxazolyl, pyridyl, benzimidazolyl, benzothiazolyl, benzoxazolyl, benzopyranyl, quinolyl, isoquinolyl, tetrahydroisoquinolyl, benzothienyl and benzofuryl, each of which may have one or more substituent(s) selected from the group consisting of methyl, methoxy, chlorine, oxy, methoxycarbonyl, oxo, pyrrolidinylcarbonyl, carboxy, aminocarbonyl, acetyl, (3-azabicyclol[3.2.2]non-3-yl)carbonyl, dimethylaminoethylaminocarbonyl and t-butyl; or a group of the formula: —X—$R^4$

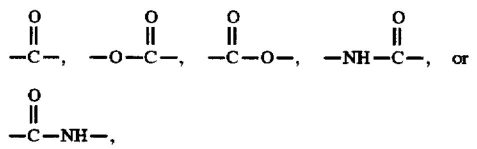

and $R^4$ is thiomorpholinyl; pyridyl; 3-azabicyclo[3.2.2]non-3-yl, 6-azabicyclo[3.2.1]oct-6-yl, 2-azabicyclo[2.2.1]hept-5-en-2-yl, 2-azabicyclo[2.2.1]hept-2-yl, 2,5-diazabicyclo[2.2.1]hept-2-yl, 3,8-diazabicyclo[3.2.1]oct-3-yl or 2-azatricyclo[4.3.1.1$^{4,8}$]undec-2-yl, each of which may have one or more substituent(s) selected from the group consisting of benzyl and methyl; or adamantyl);

Y is O or S, and

—Z— is direct single bond between carbon and $R^2$, or

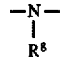

(in which $R^8$ is hydrogen or methyl), or a pharmaceutically acceptable salt thereof.

5. A process for preparing a compound of the formula;

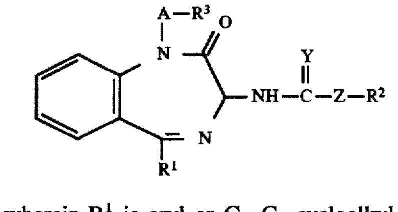

(I)

wherein $R^1$ is aryl or $C_3$–$C_8$ cycloalkyl, each of which may have one or more suitable substituent(s), $R^2$ is $C_3$–$C_8$ cycloalkyl, aryl, indanyl or a heterobicyclic group other than 2-indolyl, each of which may have one or more suitable substituent(s), A is lower alkylene, and $R^3$ is a heterocyclic group selected from the group consisting of tetrahydrofuryl, dioxolanyl, furyl, thienyl, isoxazolyl, pyridyl, benzimidazolyl, benzothiazolyl, benzoxazolyl, benzopyranyl, quinolyl, isoquinolyl, tetrahydroisoquinolyl, benzothienyl and benzofuryl, each of which may have one or more suitable substituent(s); or a group of the formula: —X—$R^4$

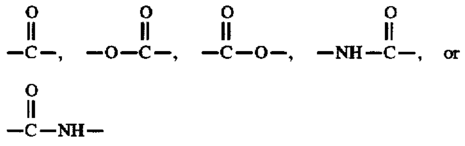

and $R^4$ is thiomorpholinyl; pyridyl; a bridged heterocyclic group containing at least one nitrogen atom, which may have one or more suitable substituent(s); or a bridged cyclic-hydrocarbon group), Y is O or S, and —Z— is direct single bond between carbon and $R^2$, or

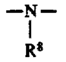

(in which $R^8$ is hydrogen or lower alkyl), or a salt thereof, which comprises, (1) reacting a compound of the formula (II):

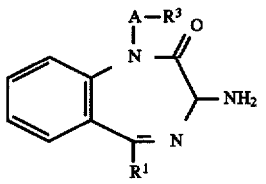

(II)

wherein $R^1$, $R^3$ and A are each as defined above, or its reactive derivatives at the amino group or a salt thereof with a compound of the formula (III):

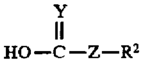

(III)

wherein $R^2$, Y and Z are each as defined above, or its reactive derivative or a salt thereof to give a compound of the formula (I):

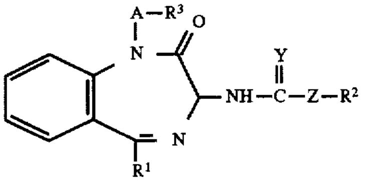

(I)

wherein $R^1$, $R^2$, $R_3$, A, Y and Z are each as defined above, or a salt thereof, (2) reacting a compound of the formula (IV):

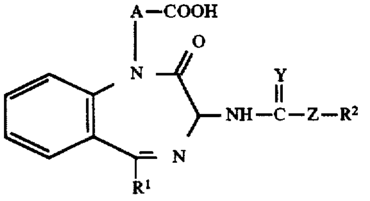

(IV)

wherein $R^1$, $R^2$, Y, Z, and A are each as defined above, or its reactive derivative at the carboxy group or a salt thereof with a compound of the formula (V):

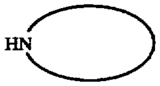

(V)

wherein

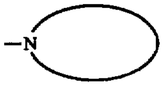

is a bridged heterocyclic group containing at least one nitrogen atom, which may have one or more suitable substituent(s) or its reactive derivative at the imino group or salt thereof to give a compound of the formula (Ia):

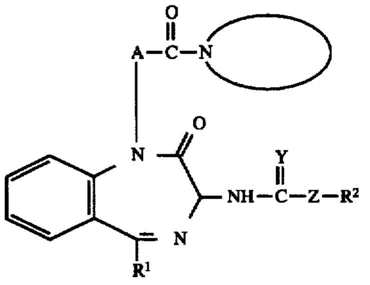

(Ia)

wherein $R^1$, $R^2$, Y, Z, A and

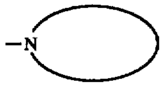

are each as defined above, or a salt thereof, or (3) reacting a compound of the formula (IV):

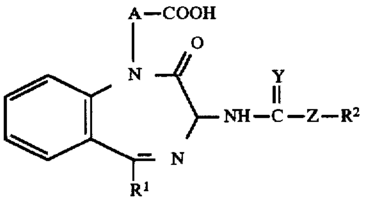

(IV)

wherein $R^1$, $R^2$, Y, Z and A are each as defined above, or its reactive derivative at the carboxy group or a salt thereof with a compound of the formula (XIII):

$H_2N—R^7$ (XIII)

wherein $R^7$ is a bridged cyclic-hydrocarbon group, or its reactive derivative at the amino group or a salt thereof to give a compound of the formula (Ib):

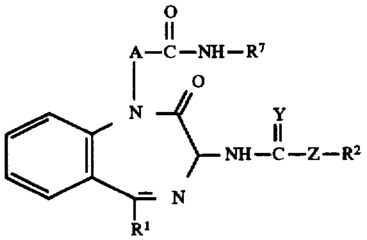

(Ib)

wherein $R^1$, $R^2$, Y, Z, A and $R^7$ are each as defined above, or a salt thereof.

6. A pharmaceutical composition which comprises, as an active ingredient, a compound of claim 1 or a pharmaceutically acceptable salt thereof in admixture with pharmaceutically acceptable carriers.

7. A method for treating or preventing cholecystokinin-mediated diseases which comprises administering a compound of claim 1 or a pharmaceutically acceptable salt thereof to human or animals.

8. A process for preparing a pharmaceutical composition which comprises admixing a compound of claim 1 or a pharmaceutically acceptable salt thereof with a pharmaceutically acceptable carrier.

* * * * *